US009650601B2

(12) United States Patent
Nitzel et al.

(10) Patent No.: US 9,650,601 B2
(45) **Date of Patent: *May 16, 2017**

(54) PCV/MYCOPLASMA HYOPNEUMONIAE/PRRS COMBINATION VACCINE

(71) Applicant: Zoetis Services LLC, Florham Park, NJ (US)

(72) Inventors: Gregory P. Nitzel, Paw Paw, MI (US); Jeffrey E. Galvin, Lincoln, NE (US); John Keith Garrett, North Wilkesboro, NC (US); James R. Kulawik, II, Lincoln, NE (US); Tracy L. Ricker, Portage, MI (US); Megan Marie Smutzer, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/712,454

(22) Filed: May 14, 2015

(65) Prior Publication Data

US 2015/0284678 A1 Oct. 8, 2015

Related U.S. Application Data

(62) Division of application No. 13/850,331, filed on Mar. 26, 2013, now Pat. No. 9,125,886.

(60) Provisional application No. 61/620,189, filed on Apr. 4, 2012.

(51) Int. Cl.

| | |
|---|---|
| ***C12N 1/36*** | (2006.01) |
| ***A61K 39/02*** | (2006.01) |
| ***A61K 39/12*** | (2006.01) |
| ***A61K 39/295*** | (2006.01) |
| *A61K 39/00* | (2006.01) |

(52) U.S. Cl.

CPC ............ *C12N 1/36* (2013.01); *A61K 39/0208* (2013.01); *A61K 39/0241* (2013.01); *A61K 39/12* (2013.01); *A61K 39/295* (2013.01); *A61K 2039/521* (2013.01); *A61K 2039/5252* (2013.01); *A61K 2039/552* (2013.01); *A61K 2039/55566* (2013.01); *A61K 2039/70* (2013.01); *C12N 2750/10034* (2013.01); *C12N 2770/10034* (2013.01)

(58) Field of Classification Search

None

See application file for complete search history.

(56) References Cited

U.S. PATENT DOCUMENTS 4,606,918 A 8/1986 Allison et al.
4,681,870 A 7/1987 Balint et al.
5,080,896 A 1/1992 Visser et al.
5,240,706 A 8/1993 Faulds et al.
5,252,328 A 10/1993 Faulds et al.
5,338,543 A 8/1994 Fitzgerald et al.
5,534,256 A 7/1996 Potter et al.
5,565,205 A * 10/1996 Petersen ............ A61K 39/0241 424/264.1
5,620,691 A 4/1997 Wensvoort et al.
5,695,766 A 12/1997 Paul et al.
5,695,769 A 12/1997 Frantz et al.
5,788,962 A 8/1998 Wise et al.
5,846,735 A 12/1998 Stapleton et al.
6,110,467 A 8/2000 Paul et al.
6,113,916 A 9/2000 Bhogal et al.
6,162,435 A 12/2000 Minion et al.
6,193,971 B1 2/2001 Hofmann et al.
6,251,397 B1 6/2001 Paul et al.
6,251,404 B1 6/2001 Paul et al.
6,268,199 B1 7/2001 Meulenberg et al.
6,342,231 B1 1/2002 Burkhardt et al.
6,380,376 B1 4/2002 Paul et al.
6,500,662 B1 12/2002 Calvert et al.
6,585,981 B1 7/2003 Pijoan
6,592,873 B1 7/2003 Paul et al.
6,753,417 B2 6/2004 Hansen et al.
6,773,908 B1 8/2004 Paul et al.
6,846,477 B2 1/2005 Keich et al.
6,977,078 B2 12/2005 Paul et al.
7,018,638 B2 3/2006 Chu et al.
7,056,492 B2 6/2006 Goudie et al.
7,074,894 B2 7/2006 Walker et al.

(Continued)

FOREIGN PATENT DOCUMENTS

EP 0283840 A2 3/1988
EP 0283085 A1 9/1988

(Continued)

OTHER PUBLICATIONS

Collins et al. "Isolation of Swine Infertility and Respiratory Syndrome Virus (Isolate ATCC VR-2332) in North America and Experimental Reproduction of the Disease in Gnotobiotic Pigs" Journal of Veterinary Diagnostic Investigation 1992, 4:117-126.
Kwang, J et al. "Cloning, Expression, and Sequence Analysis of the ORF4 Gene of the Porcine Reproductive and Respiratory Syndrome Virus MN-1b" Journal of Veterinary Diagnostic Investigation 1994, 6:293-296.
Mardassi, H. et al. "Molecular Analysis of the ORFs 3 to 7 of Porcine Reproductive and Respiratory Syndrome Virus, Quebec Reference Strain" Archives of Virology 1995, 140:1405-1418.
Meng, X.-J. et al. "Molecular Cloning and Nucleotide Sequencing of the 3'-Terminal Genomic RNA of the Porcine Reproductive and Respiratory Syndrome Virus" Journal of General Virology 1994, 75:1795-1801.
Wensvoort, G. et al. "Mystery Swine Disease in the Netherlands: the isolation of Lelystad Virus" The Veterinary Quarterly 1991, 13:121-130.
Kim et al. "Identification and Mapping of an Immunogenic Region of Mycoplasma Hyponeumoniae p65 Surface Lipoprotein Expressed in *Escherichia coli* from a Cloned Genomic Fragment" Infection and Immunity 1990, 58:2637-2643.

(Continued)

*Primary Examiner* — Shanon A Foley
(74) *Attorney, Agent, or Firm* — Gloria K. Szakiel

(57) ABSTRACT

This invention provides a trivalent immunogenic composition including a soluble portion of a *Mycoplasma hyopneumoniae* (M.hyo) whole cell preparation; a porcine circovirus type 2 (PCV2) antigen; and a PRRS virus antigen, wherein the soluble portion of the M.hyo preparation is substantially free of both (i) IgG and (ii) immunocomplexes comprised of antigen bound to immunoglobulin.

14 Claims, 13 Drawing Sheets

(56) References Cited

U.S. PATENT DOCUMENTS

| | | | | |
|---|---|---|---|---|
| 7,169,394 | B2 | 1/2007 | Chu et al. | |
| 7,223,854 | B2 | 5/2007 | Paul et al. | |
| 7,264,802 | B2 | 9/2007 | Paul et al. | |
| 7,264,957 | B2 | 9/2007 | Paul et al. | |
| 7,279,166 | B2 | 10/2007 | Meng et al. | |
| 7,419,806 | B2 | 9/2008 | Minion et al. | |
| 7,517,976 | B2 | 4/2009 | Paul et al. | |
| 7,575,752 | B2 | 8/2009 | Meng et al. | |
| 7,622,124 | B2 | 11/2009 | Chu et al. | |
| 7,959,927 | B2 | 6/2011 | Chu et al. | |
| 8,008,001 | B2 | 8/2011 | Roerink et al. | |
| 8,187,588 | B2 | 5/2012 | Chu et al. | |
| 8,444,989 | B1 | 5/2013 | Ohnesorge et al. | |
| 2002/0114817 | A1 | 8/2002 | Liem et al. | |
| 2003/0092897 | A1 | 5/2003 | Walker et al. | |
| 2005/0079185 | A1 | 4/2005 | Parisot et al. | |
| 2006/0286123 | A1 | 12/2006 | Fetzer et al. | |
| 2009/0092636 | A1 | 4/2009 | Roof et al. | |
| 2009/0117152 | A1 * | 5/2009 | Chu .................. | A61K 39/0241 424/201.1 |
| 2009/0317423 | A1 | 12/2009 | Roof et al. | |
| 2012/0052514 | A1 | 3/2012 | Allen et al. | |
| 2013/0183338 | A1 | 7/2013 | Jacobs et al. | |
| 2013/0266603 | A1 | 10/2013 | Nitzel et al. | |

FOREIGN PATENT DOCUMENTS

| | | | |
|---|---|---|---|
| EP | 0315153 | A2 | 5/1989 |
| EP | 0595436 | A2 | 5/1994 |
| EP | 0325191 | B1 | 9/1995 |
| EP | 2 275 132 | A2 | 1/2011 |
| GB | 2282811 | | 4/1995 |
| WO | WO 91/03157 | | 3/1991 |
| WO | WO 91/18627 | | 12/1991 |
| WO | WO 92/21375 | | 12/1992 |
| WO | WO 93/03760 | | 3/1993 |
| WO | WO 93/07898 | | 4/1993 |
| WO | WO 93/10216 | | 5/1993 |
| WO | WO 93/14196 | | 7/1993 |
| WO | WO 95/30437 | | 11/1995 |
| WO | WO 96/28472 | A1 | 9/1996 |
| WO | WO 96/40268 | | 12/1996 |
| WO | WO 02/10343 | A2 | 2/2002 |
| WO | WO 02/49666 | A2 | 6/2002 |
| WO | 03003941 | A2 | 1/2003 |
| WO | WO 03/049703 | A2 | 6/2003 |
| WO | WO 2004058142 | A2 | 7/2004 |
| WO | WO 2007/116032 | A1 | 10/2007 |
| WO | WO 2009/126356 | A2 | 10/2009 |
| WO | WO 2011/141443 | A1 | 11/2011 |
| WO | WO 2012/063212 | A1 | 5/2012 |

OTHER PUBLICATIONS

Futo et al. "Molecular Cloning of a 46-Kilodalton Surface Antigen (P46) Gene from Mycoplasma Hyopneumoniae: Direct Evidence of CGG Codon Usage for Arginine" Journal of Bacteriology 1995, 177:1915-1917.

Zhang et al. "Identification and Characterization of a Mycoplasma Hyopneumoniae Adhesin" Infection and Immunity 1995, 63: 1013-1029.

King et al. "Characterization of the Gene Encoding Mhp1 from Mycoplasma Hyopneumoniae and Examination of Mhp1's Vaccine Potential" Vaccine 1997, 15:25-35.

Okada et al. "Protective Effect of Vaccination with Culture Supemate of M.Hyopneumoniae Against Experimental Infection in Pigs" Journal of Veterinary Medicine 2000, 47:527-533.

Scarman et al. "Identification of Novel Species-Specific Antigens of Mycoplasma Hyopneumoniae by Preparative SDS-PAGE ELISA Profiling" Microbiology 1997, 143:663-673.

Strait et al. "Efficacy of a Mycoplasma Hyponeumoniae Bacterin in Pigs Challenged With Two Contemporary Pathogenic Isolates of M Hyopneumoniae" Journal of Swine Health and Production 2008, 16:200-206.

Alexander et al. "Adjuvants and their Modes of Action" Livestock Production Science 1995, 42;153-162.

Hunter et al. "The Adjuvant Activity of Nonionic Block Polymer Surfactants" The Journal of Immunologists 1981, 127:1244-1250.

Allison "Squalene and Squalane Emulsions as Adjuvants" Methods 1999, 19:87-93.

Goodwin et al. "Enzootic Pneumonia of Pigs: Immunization Attempts Inoculating Mycoplasma Suipneumoniae Antigen by Various Routes and with Different Adjuvants" British Veterinary Journal 1973, 129:456-464.

George et al. "Route-Related Variation in the Immunogenicity of Killed *Salmonella enteritidis* Vaccine: Role of Antigen Presenting Cells" Microbiol Immunol 1989, 33:479-488.

Byars et al. "Adjuvant Formulation for use in Vaccines to Elicit Both Cell-Mediated and Humoral Immunity" Vaccine 1987, 5:223-228.

Martinon et al. "Efficacy of a 'One Shot' Schedule of a Mycoplasma Hyopneumoniae Bacterin (Hyoresp)" Proceedings of the 15$^{th}$ IPVS Congress, Birmingham, England, Jul. 5-9, 1998, p. 284.

Reynaud et al. "Clinical Field Trial With Mycoplasma Hyopneumoniae Bacterin (Hyoresp)" Proceedings of the 15$^{th}$ IPVS Congress, Birmingham, England, Jul. 5-9, 1998, p. 150.

Charlier et al. "Comparative Efficacy of Stellamune Mycoplasma and Hyoresp in Pigs Against an Experimental Challenge with Mycoplasma Hyopneumoniae" The 16$^{th}$ International Pig Veterinary Society Congress, Melbourne, Australia Sep. 17-20, 2000 p. 501.

Djordjevic et al. "Serum and mucosal antibody responses and protection in pigs vaccinated against mycoplasma hyopneumoniae with vaccines containing a denatured membrane antigen pool and adjuvant", Australian Veterinary Journal, vol. 75 No. 7, pp. 504-511, Jul. 1, 1997.

Chen et al. "Evaluation of immune response to recombinant potential protective antigens of mycoplasma hyopneumoniae delivered as cocktail DNA and/or recombinant protein vaccines in mine", Vaccine, vol. 26 No. 34, pp. 4372-4378, Aug. 12, 2008.

Drexler et al. "Efficacy of combined porcine reproductive and respiratory syndrome virus and mycoplasma hyopneumoniae vaccination in piglets", Veterinary Record, vol. 166 No. 3, pp. 70-74, Jan. 16, 2010.

Grau-Roma et al. "Recent advances in the epidemiology, diagnosis and control of diseases caused by porcine circovirus type 2", Veterinary Journal, vol. 187 No. 1, pp. 23-32, Jan. 1, 2011.

Okada et al. "Cytological and immunological changes in bronchoaiveolar lavage fluid and histological observation of lung lesions in pigs immunized with mycoplasma hyopneumoniae inactivated vaccine prepared from broth culture supernate", Vaccine, vol. 18 No. 25, pp. 2825-2831, Jun. 1, 2000.

Okada M.et al. "Evaluation of mycoplasma hyopneumoniae inactivated vaccine in pigs under field conditions", J. Vet. Med. Science, vol. 61 No. 10, pp. 1131-1135, Jun. 25, 1999.

Genzow Marika et al. "Concurrent vaccination of piglets with Ingel vac® PRRS MLV and with Ingelvac® M. hyo", Tieraerztliche Umschau, vol. 61 No. 12, pp. 649-652, Dec. 1, 2006.

Xin-Gang et el. "Baculovirus as a PRRSV and PCV2 bivalent vaccine vector: Baculovirus virions displaying simultaneously GP5 glycoprotein of PRRSV and capsid protein of PCV2", Journal of Virological Methods, vol. 179 No. 2, pp. 359-366, Nov. 28, 2011.

Ross "Characteristics of a protective activity of mycoplasma hyopneumoniae vaccine" American Journal of Veterinary Research, vol. 45 No. 10, pp. 1899-1905, Oct. 1984.

Sheldrake et al. "Evaluation of an enzyme-linked immunosorbent assay for the detection of Mycoplasma hyopneumoniae antibody in porcine serum" Australian Veterinary Journal vol. 69, No. 10, Oct. 1992.

Fort Dodge Australia (2000) TechNote—Technical Update TF S04-00 (1) "Suvaxyn M. Hyo—How it works".

Zanh et al. (Journal of General Virology 2005; 86: 677-685).

Redgeld et al. (Nature Medictne 2002; 8 (7): 694-701).

Declaration of Gregory P. Nitzel From U.S. Appl. No. 13/850,318.

* cited by examiner

| Contrast | Mitigated Fraction | 95% confidence interval |
|---|---|---|
| T01 vs T02 | 41.2 | -5.9 to 76.5 |
| T01 vs T03 | 64.7 | 29.4 to 100 |
| T01 vs T04 | 76.5 | 41.2 to 100 |
| T01 vs T05 | 73.3 | 33.3 to 100 |
| T01 vs T06 | 62.5 | 25 to 100 |
| T01 vs T07 | 87.5 | 62.5 to 100 |
| T01 vs T08 | 88.2 | 64.7 to 100 |

Figure 10

| Preliminary Viricidal Activity | Difference from Water | | | |
|---|---|---|---|---|
| | 100% rehyd. | 90/10 | 90/10 | |
| | Lyophilized Titer | Liq. (DMEM) 90/10 | Liq. (Ultra) 90/10 | Avg Viricidal Activity |
| 20% SLCD | 0.8 | 0.7 | 2.0 | 1.3 |
| 0.2% Carbopol | 0.3 | -0.3 | 0.2 | -0.1 |
| 10% SP-Oil | 0.2 | 0.0 | 0.0 | 0.0 |
| 10% SP-Oil/0.2% Carbopol | 0.3 | -0.2 | 0.0 | -0.1 |
| 20% SLCD/10% SP-Oil | 1.0 | 0.3 | 0.7 | 0.5 |
| 20% SLCD/10% SP-Oil/0.2% Carbopol | 0.2 | 0.0 | 0.5 | 0.3 |
| 5% Amphigen (from 40% stock) | 1.0 | 0.7 | 1.5 | 1.1 |
| 2.5% Amphigen (from 40% stock) | NA | -0.2 | NA | -0.2 |
| 5% Amphigen (from 20% stock) | NA | 0.8 | NA | 0.8 |
| 2.5% Amphigen (from 20% stock) | NA | 0.2 | NA | 0.2 |
| 5% Amphigen (from 40% stock) | NA | 1.3 | NA | 1.3 |
| 2.5% Amphigen (from 40% stock) | NA | 0.8 | NA | 0.8 |
| | Indicates potential viricidal activity | | | |

| | 0 | 7 | 13 | 20 | 28 | 35 | 42 |
|---|---|---|---|---|---|---|---|
| T01 | 1 | 1 | 1 | 1 | 177259 | 47745.8 | 3536.02 |
| T02 | 1 | 1 | 1 | 1 | 231.12 | 15.13 | 1 |
| T03 | 1 | 1 | 1 | 1 | 28.72 | 17.78 | 1 |

| | day -1 | day 7 | day 13 | day 20 | day 28 | day 35 | day 42 |
|---|---|---|---|---|---|---|---|
| T01 | 0.073 | 0.039 | 0.007 | 0.043 | 0.007 | 0.311 | 0.441 |
| T02 | 0.076 | 0.038 | 0.009 | 0.029 | 0.292 | 0.504 | 0.588 |
| T03 | 0.059 | 0.037 | 0.019 | 0.038 | 0.352 | 0.632 | 0.665 |

PCV/MYCOPLASMA HYOPNEUMONIAE/PRRS COMBINATION VACCINE

CROSS-REFERENCE TO RELATED APPLICATIONS

This application is a divisional of U.S. application Ser. No. 13/850,331, filed Mar. 26, 2013, which claims the benefit of U.S. Provisional Application No. 61/620,189, filed Apr. 4, 2012, the contents each of which are incorporated herein by reference in their entirety.

FIELD OF THE INVENTION

The present invention relates to porcine circovirus, *Mycoplasma hyopneumoniae* (*M. hyopneumoniae* or M.hyo), and Porcine reproductive and respiratory syndrome (PRRS) virus. More particularly, the invention relates to a trivalent immunogenic composition including a soluble portion of an M.hyo whole cell preparation, a PCV2 antigen, and a PRRS virus antigen and its use in a vaccine for protecting pigs against at least enzootic pneumonia and Post-weaning Multisystemic Wasting Syndrome (PMWS).

BACKGROUND OF THE INVENTION

Enzootic pneumonia in swine, also called mycoplasmal pneumonia, is caused by M.hyo. The disease is a chronic, non-fatal disease affecting pigs of all ages. Infected pigs show only mild symptoms of coughs and fever, but the disease has significant economic impact due to reduced feed efficiency and reduced weight gain. Enzootic pneumonia is transmitted from pig to pig through the nasal passages by airborne organisms expelled from the lungs of infected pigs. The primary infection by M.hyo may be followed by secondary infection by other *mycoplasma* species (*Mycoplasma hyorhinis* and *Mycoplasma flocculare*) as well as other bacterial pathogens.

M.hyo is a small, prokaryotic microbe capable of a free living existence, although it is often found in association with eukaryotic cells because it has absolute requirements for exogenous sterols and fatty acids. These requirements generally necessitate growth in serum-containing media. M.hyo is bounded by a cell membrane, but not a cell wall.

The physical association of mycoplasmas with the host cell surface is the basis for the development and persistence of enzootic pneumonia. M.hyo infects the respiratory tract of swine, colonizing the trachea, bronchi, and bronchioles. The *mycoplasma* produces a ciliostatic factor which causes the cilia lining the respiratory passages to stop beating. Eventually, the cilia degenerate, leaving the pig prone to infection by secondary pathogens. Characteristic lesions of purple to gray areas of consolidation are observed in infected animals. Surveys of slaughtered animals revealed lesions in 30 to 80% of swine. Results from 37 herds in 13 states indicated that 99% of the herds had hogs with pneumonia lesions typical of enzootic pneumonia. Therefore, the need for effective preventative and treatment measures are great.

Antibiotics such as tiamulin, trimethoprim, tetracyclines and lincomycin have some benefit, but are expensive and require prolonged use. Additionally, antibiotics have not been shown to effectively eliminate spread or reinfection of M.hyo. Prevention by maintaining pathogen-free herds is sometimes possible but reintroduction of M.hyo often occurs. Due to the serious economic consequences of swine pneumonia, vaccines against M.hyo have been sought. Vaccines containing preparations of mycoplasmal organisms grown in serum-containing medium have been marketed, but raise concerns regarding adverse reactions induced by serum components (such as immunocomplexes or non-immunogenic specific proteins) present in the immunizing material. Other attempts to provide M.hyo vaccines have been successful, but the disease remains widespread.

M.hyo and porcine circovirus type 2 (PCV2) are the two most prevalent pathogens that are encountered in the pig industry. Swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia. M.hyo is associated with enzootic pneumonia and has also been implicated as one of the major co-factors in the development of Porcine Circovirus Associated Disease (PCVAD).

Porcine reproductive and respiratory syndrome (PRRS) is caused by an arterivirus, which has a particular affinity for the macrophages particularly those found in the lung (alveolar macrophages). These macrophages ingest and remove invading bacteria and viruses, but not in the case of the PRRS virus (PRRSV). In the case of the PRRS virus, it multiplies inside the macrophages producing more virus and kills the macrophages. Once PRRSV has entered a herd, it tends to remain present and active indefinitely. Up to 40% of the macrophages are destroyed, which allows bacteria and other viruses to proliferate and do damage. A common example of this is the noticeable increase in severity of enzootic pneumonia in grower/finisher units when they become infected with PRRSV. More than half of weaning-age PRRS virus-negative pigs become infected before going to market.

What is needed is a PCV2/M.hyo/PRRS trivalent vaccine against PCV2, *mycoplasma*, and PRRSV infection in swine. It would be highly desirable to provide a single dose trivalent vaccine. Preferably, the PCV2/M.hyo component of the vaccine would be provided as a ready-to-use in one bottle liquid composition which can be easily combined with the PRRSV component such that all antigens can be administered to the pig simultaneously.

SUMMARY OF THE INVENTION

The present invention provides a trivalent immunogenic composition including a soluble portion of a *Mycoplasma hyopneumoniae* (M.hyo) whole cell preparation; a porcine circovirus type 2 (PCV2) antigen; and a porcine reproductive and respiratory syndrome (PRRS) virus antigen, wherein the soluble portion of the M hyo preparation is substantially free of both (i) IgG and (ii) immunocomplexes comprised of antigen bound to immunoglobulin. In one aspect, the soluble portion of the M.hyo whole cell preparation has been treated with protein-A or protein-G prior to being added to the immunogenic composition. In a further aspect, the soluble portion of the M.hyo preparation and the PCV2 antigen are in the form of a ready-to-use liquid composition.

In one embodiment, the PRRS virus antigen is a genetically modified live virus. In another embodiment, the genetically modified live PRRS virus is in the form of a lyophilized composition.

In one embodiment, the soluble portion of the M.hyo preparation includes at least one M.hyo protein antigen. In another embodiment, the soluble portion of the M.hyo preparation includes two or more M.hyo protein antigens.

In one embodiment, the PCV2 antigen is in the form of a chimeric type-1-type 2 circovirus, the chimeric virus including an inactivated recombinant porcine circovirus type 1 expressing the porcine circovirus type 2 ORF2 protein. In another embodiment, the PCV2 antigen is in the form of a recombinant ORF2 protein. In still another embodiment, the recombinant ORF2 protein is expressed from a baculovirus vector.

In some embodiments, the trivalent composition of the present invention elicits a protective immune response against M.hyo, PCV2, and PRRS virus. In other embodiments, the immunogenic composition of the present invention further includes at least one additional antigen. In one embodiment, the at least one additional antigen is protective against a microorganism that can cause disease in pigs.

In one embodiment, the microorganism includes bacteria, viruses, or protozoans. In another embodiment, the microorganism is selected from, but is not limited to, the following: porcine parvovirus (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplama hyorhinis, Mycoplasma hyosynoviae, leptospira bacteria, Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmissable Gastroenteritis, or combinations thereof.

In some embodiments, the composition of the present invention further includes an adjuvant. In one embodiment, the adjuvant is selected from, but is not limited to, the following: an oil-in-water adjuvant, a polymer and water adjuvant, a water-in-oil adjuvant, an aluminum hydroxide adjuvant, a vitamin E adjuvant and combinations thereof. In another embodiment, the composition of the present invention further includes a pharmaceutically acceptable carrier.

In certain embodiments, the composition of the present invention elicits a protective immune response against M.hyo, PCV2 and PRRS virus when administered as a single dose administration.

The present invention also provides a method of immunizing a pig against M.hyo, PCV2, and PRRS virus. This method includes administering to the pig a trivalent immunogenic composition including a soluble portion of a *Mycoplasma hyopneumoniae* (M.hyo) whole cell preparation; a porcine circovirus type 2 (PCV2) antigen; and a PRRS virus antigen, wherein the soluble portion of the M. hyo preparation is substantially free of both (i) IgG and (ii) immunocomplexes comprised of antigen bound to immunoglobulin.

In one embodiment of the method of the present invention, the trivalent composition is administered intramuscularly, intradermally, transdermally, or subcutaneously. In another embodiment of the method of this invention, the trivalent composition is administered in a single dose.

In a further embodiment, the composition is administered to pigs having maternally derived antibodies against at least one of M.hyo, PCV2, and PRRS virus. In a still further embodiment, the composition is administered to pigs having maternally derived antibodies against M.hyo, PCV2, and PRRS virus.

In one embodiment, the composition is administered to pigs at 3 weeks of age or older.

The present invention also provides a method for preparing an immunogenic composition according to the present invention. This method includes i) culturing M.hyo in a suitable media over periods ranging from 18-144 hours; ii) subsequently inactivating the M. hyo culture; iii) harvesting the inactivated culture fluid, wherein the inactivated culture fluid comprises an M.hyo whole cell preparation comprising both a soluble liquid fraction and insoluble cellular material; iv) separating the soluble liquid fraction from the insoluble cellular material; v) substantially removing both IgG and antigen/immunoglobulin immunocomplexes from the separated soluble liquid fraction to form a soluble portion of the M.hyo whole cell preparation; and vi) subsequently combining the soluble portion of the M.hyo whole cell preparation with a PCV2 antigen and a PRRS virus antigen. In one embodiment, step vi) includes combining a ready-to-use liquid composition comprising both the PCV2 antigen and the M.hyo soluble portion with a lyophilized PRRS virus antigen.

In one embodiment, a kit according to the present invention includes a first bottle (or other suitable receptable) comprising a composition including both a PCV2 antigen and the soluble portion of a *Mycoplasma hyopneumoniae* (M.hyo) whole cell preparation, wherein the soluble portion of the M.hyo preparation is substantially free of both (i) IgG and (ii) antigen/immunoglobulin immunocomplexes; and a second bottle comprising PRRS virus antigen. In one embodiment, the composition in the first bottle is provided as a ready-to-use liquid composition. In a further embodiment, the PRRS virus antigen component of the kit is in the form of a lyophilized composition. In another embodiment, the kit includes an instruction manual with directions to combine the contents from the first bottle with the contents of the second bottle. In yet another embodiment, the instruction manual further includes directions to administer the combined contents of the first and second bottles to a pig.

BRIEF DESCRIPTION OF THE DRAWINGS

FIG. 10 is a table showing the adjuvant evaluation for virucidal activity against PRRS virus.

BRIEF DESCRIPTION OF THE SEQUENCES

Figure 1:
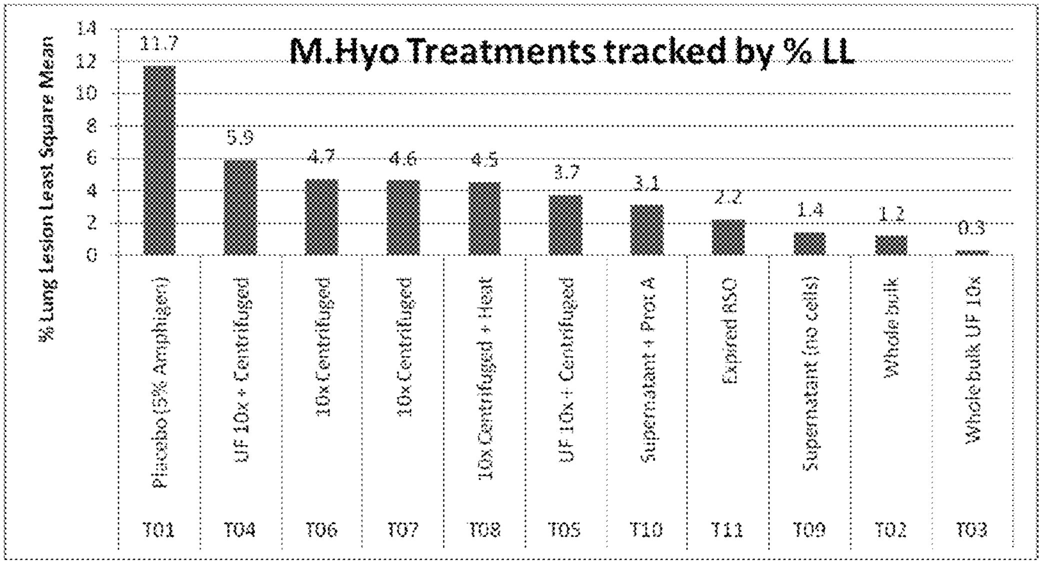
FIG. 1 is a graph showing the efficacy of M.hyo monovalent vaccines prepared with M.hyo antigens from different treatments (T02-T10 described in Example 3) vs. a placebo (T01). The results are presented as % Lung Lesion Least Square Mean values.

SEQ ID NO: 1 is one embodiment of a nucleotide sequence encoding p46 from the P-5722 strain of M.hyo;

SEQ ID NO: 2 is one embodiment of an amino acid sequence corresponding to p46 from the P-5722 strain of M.hyo;

SEQ ID NO: 3 is one embodiment of a nucleotide sequence encoding p97 from the P-5722 strain of M.hyo;

SEQ ID NO: 4 is one embodiment of an amino acid sequence corresponding to p97 from the P-5722 strain of M.hyo;

SEQ ID NO: 5 is one embodiment of a genomic sequence encoding a chimeric PCV1-2 virus;

SEQ ID NO: 6 is one embodiment of a nucleotide sequence corresponding to ORF2 of a porcine circovirus;

SEQ ID NO: 7 is one embodiment of an amino acid sequence corresponding to the ORF2 polypeptide of a porcine circovirus;

SEQ ID NO: 8 is one embodiment of a genomic sequence encoding a chimeric PCV1-2 virus;

SEQ ID NO: 9 is one embodiment of a nucleotide sequence corresponding to ORF2 of a porcine circovirus;

SEQ ID NO: 10 is one embodiment of an amino acid sequence corresponding to the ORF2 polypeptide of a porcine circovirus;

SEQ ID NO: 11 is one embodiment of an amino acid sequence corresponding to the ORF2 polypeptide of a porcine circovirus;

SEQ ID NO: 12 is one embodiment of a nucleotide sequence encoding the amino acid sequence of SEQ ID NO: 11;

SEQ ID NO: 13 is one embodiment of an amino acid sequence corresponding to the ORF2 polypeptide of a porcine circovirus;

SEQ ID NO: 14 is one embodiment of a nucleotide sequence encoding the amino acid sequence of SEQ ID NO: 13;

SEQ ID NO: 15 is one embodiment of an amino acid sequence corresponding to the ORF2 polypeptide of a porcine circovirus;

SEQ ID NO: 16 is one embodiment of a genomic sequence of a non-virulent form of the North American PRRS virus isolate designated P129; and SEQ ID NO: 17 is one embodiment of a nucleotide sequence corresponding to ORF2 to ORF5 of the PRRSV isolate designated ISU-55.

SEQ ID NO: 18 is one embodiment of a nucleotide sequence corresponding to ORF6 and ORF7 of the PRRSV isolate designated ISU-55.

DETAILED DESCRIPTION OF THE INVENTION

The present invention provides a trivalent immunogenic composition including a soluble portion of a *Mycoplasma hyopneumoniae* (M. hyo) whole cell preparation; a porcine circovirus type 2 (PCV2) antigen, and a porcine reproductive and respiratory syndrome (PRRS) virus antigen, wherein the soluble portion of the M. hyo preparation is substantially free of both (i) IgG and (ii) immunocomplexes comprised of antigen bound to immunoglobulin. In one embodiment, the trivalent composition elicits a protective immune response in a pig against PCV2, M.hyo, and PRRS virus.

Applicants have surprisingly discovered that the insoluble fraction of the M.hyo whole cell preparation is non-immunogenic. In contrast, the IgG-free M.hyo soluble preparation is immunogenic and can be effectively combined with antigens from other pathogens, such as PCV2 and PRRSV, without analytical or immunological interference between the antigens. This makes the M.hyo soluble preparation an effective platform for the multivalent vaccines of this invention. Applicants have also surprisingly discovered that removing the immunoglobulin and the insoluble cell debris from the M.hyo preparation enhances the safety of the immunogenic composition.

As used in the specification and claims, the singular form "a", "an" and "the" include plural references unless the context clearly dictates otherwise. For example, the term "a protein antigen" includes a plurality of protein antigens, including mixtures thereof.

As used herein, the term "comprising" is intended to mean that the compositions and methods include the recited elements, but do not exclude other elements.

As defined herein, a soluble portion of an M.hyo whole cell preparation refers to a soluble liquid fraction of an M.hyo whole cell preparation after separation of the insoluble material and substantial removal of IgG and antigen-bound immunocomplexes. The M.hyo soluble portion may alternatively be referred to herein as the supernatant fraction, culture supernatant and the like. It includes M.hyo-expressed soluble proteins (M.hyo protein antigens) that have been separated or isolated from insoluble proteins, whole bacteria, and other insoluble M.hyo cellular material by conventional means, such as centrifugation, filtration, or precipitation. In addition to including M.hyo-specific soluble proteins, the soluble portion of the M.hyo whole cell preparation also includes heterologous proteins, such as those contained in the culture medium used for M.hyo fermentation.

The term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten).

As defined herein, an "immunogenic or immunological composition", refers to a composition of matter that comprises at least one antigen which elicits an immunological response in the host of a cellular and or antibody-mediated immune response to the composition or vaccine of interest.

The term "immune response" as used herein refers to a response elicited in an animal. An immune response may refer to cellular immunity (CMI); humoral immunity or may involve both. The present invention also contemplates a response limited to a part of the immune system. Usually, an "immunological response" includes, but is not limited to, one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "immunogenicity" means capable of producing an immune response in a host animal against an antigen or antigens. This immune response forms the basis of the protective immunity elicited by a vaccine against a specific infectious organism.

An "adjuvant" as used herein means a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right and are believed to function synergistically.

As used herein, the term "multivalent" means a vaccine containing more than one antigen whether from the same species (i.e., different isolates of *Mycoplasma hyopneumoniae*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

The term "pig" or "piglet" as used herein means an animal of porcine origin, while "sow" refers to a female of reproductive age and capability. A "gilt" is a female pig who has never been pregnant.

As used herein, the term "virulent" means an isolate that retains its ability to be infectious in an animal host.

"Inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal or formalin), sonication, radiation, heat or any other convention means sufficient to prevent replication or growth of the organism while maintaining its immunogenicity.

The term "variant" as used herein refers to a polypeptide or a nucleic acid sequence encoding a polypeptide, that has one or more conservative amino acid variations or other minor modifications such that the corresponding polypeptide has substantially equivalent function when compared to the wild-type polypeptide.

"Conservative variation" denotes the replacement of an amino acid residue by another biologically similar residue, or the replacement of a nucleotide in a nucleic acid sequence such that the encoded amino acid residue does not change or is another biologically similar residue. Examples of conservative variations include the substitution of one hydrophobic residue, such as isoleucine, valine, leucine or methionine for another hydrophobic residue, or the substitution of one polar residue, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

"North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRSV (Mardassi, H. et al., 1995, Arch. Virol. 140:1405-1418); and North American PRRS virus isolate VR 2385 (Meng, X.-J et al., 1994, J. Gen. Virol. 75:1795-1801). Additional examples of North American PRRS virus strains are described herein. Genetic characteristics refer to genomic nucleotide sequence similarity and amino acid sequence similarity shared by North American PRRS virus strains. Chinese PRRS virus strains generally evidence about 80-93% nucleotide sequence similarity with North American strains.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus". Further examples of European PRRS virus strains are described herein.

A genetically modified virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

An "Infectious clone" is an isolated or cloned genome of the disease agent (e.g. viruses) that can be specifically and purposefully modified in the laboratory and then used to re-create the live genetically modified organism. A live genetically modified virus produced from the infectious clone can be employed in a live viral vaccine. Alternatively, inactivated virus vaccines can be prepared by treating the live virus derived from the infectious clone with inactivating agents such as formalin or hydrophobic solvents, acids, etc., by irradiation with ultraviolet light or X-rays, by heating, etc.

All currently available M.hyo and M.hyo combination vaccines are made from killed whole cell *mycoplasma* preparations (bacterins). In contrast, the present invention employs a soluble portion of a *Mycoplasma hyopneumoniae* (M.hyo) whole cell preparation for combination with the PCV2 and PRRSV antigens, wherein the soluble portion of the M.hyo preparation is substantially free of both (i) IgG and (ii) immunocomplexes comprised of antigen bound to immunoglobulin.

M.hyo has absolute requirements for exogenous sterols and fatty acids. These requirements generally necessitate growth of M.hyo in serum-containing media, such as porcine serum. Separation of the insoluble material from the soluble portion of the M.hyo whole cell preparation (e.g., by centrifugation, filtration, or precipitation) does not remove the porcine IgG or immune complexes. In one embodiment of the present invention, the M.hyo soluble portion is treated with protein-A or protein-G in order to substantially remove the IgG and immune complexes contained in the culture supernatant. In this embodiment, it is understood that protein A treatment occurs post-M.hyo fermentation. This is alternatively referred to herein as downstream protein A treatment. In another embodiment, upstream protein A treatment of the growth media (i.e., before M.hyo fermentation) can be employed. Protein A binds to the Fc portion of IgG. Protein G binds preferentially to the Fc portion of IgG, but can also bind to the Fab region. Methods for purifying/removing total IgG from crude protein mixtures, such as tissue culture supernatant, serum and ascites fluid are known in the art.

In some embodiments, the soluble portion of the M.hyo preparation includes at least one M.hyo protein antigen. In other embodiments, the soluble portion of the M.hyo preparation includes two or more M.hyo protein antigens.

In one embodiment, the M.hyo supernatant fraction includes one or more of the following M.hyo specific protein antigens: M.hyo proteins of approximately 46 kD (p46), 64 kD (p64) and 97 kD (p97) molecular weights. In another embodiment, the supernatant fraction at least includes the p46, p64 and p97 M.hyo protein antigens. The M.hyo protein of approximately 64 kD (p64) may be alternatively referred to herein as the p65 surface antigen from M.hyo described by Kim et al. [Infect. Immun. 58(8):2637-2643 (1990)], as well as in U.S. Pat. No. 5,788,962.

Futo et al. described the cloning and characterization of a 46 kD surface protein from M.hyo, which can be employed in the compositions of this invention [J. Bact 177: 1915-1917 (1995)]. In one embodiment, the M.hyo culture supernatant includes the p46 whose corresponding nucleotide and amino acid sequences from the P-5722 strain are set forth in SEQ ID NOs: 1 and 2, respectively. It is further contemplated that variants of such p46 sequences can be employed in the compositions of the present invention, as described below.

Zhang et al. described and characterized a p97 adhesin protein of M.hyo [Infect. Immun. 63: 1013-1019, 1995]. Additionally, King et al. described a 124 kD protein termed Mhp1 from the P-5722 strain of M.hyo and presented data suggesting that Mhp1 and p97 are the same protein [Vaccine 15:25-35 (1997)]. Such p97 proteins can be employed in the compositions of this invention. In one embodiment, the M.hyo culture supernatant includes the p97 whose corresponding nucleotide and amino acid sequences from the P-5722 strain are set forth in SEQ ID NOs: 3 and 4, respectively. It is further contemplated that variants of such p97 sequences can be employed in the compositions of the present invention, as described below.

The M.hyo culture supernatant may include further M.hyo specific protein antigens such as, but not limited to, proteins of approximately 41 kD (p41), 42 kD (p42), 89 kD (p89), and 65 kD (p65). See, Okada et al., 2000, J. Vet. Med. B 47:527-533 and Kim et al., 1990, Infect. Immun. 58(8): 2637-2643. In addition, the M.hyo culture supernatant can include M.hyo specific protein antigens of approximately 102 kD (p102) and 216 kD (p216). See, U.S. Pat. Nos. 6,162,435 and 7,419,806 to Minnion et al.

Any M.hyo strain may be used as a starting material to produce the soluble portion of the M.hyo preparation of the compositions of the present invention. Suitable strains of M.hyo may be obtained from commercial or academic sources, including depositories such as the American Type Culture Collection (ATCC) (Manassas, Va.) and the NRRL Culture Collection (Agricultural Research Service, U.S. Department of Agriculture, Peoria, Ill.). The ATCC alone lists the following six strains of M.hyo for sale: M.hyo ATCC 25095, M.hyo ATCC 25617, M.hyo ATCC 25934, M.hyo ATCC 27714, M.hyo ATCC 27715, and M.hyo ATCC 25934D. A preferred strain of M.hyo for use in the embodiments of this invention is identified as strain P-5722-3, ATCC #55052, deposited on May 30, 1990 pursuant to the accessibility rules required by the U.S. Patent and Trademark Office. In view of the widespread dissemination of the disease, strains may also be obtained by recovering M.hyo from lung secretions or tissue from swine infected with known strains causing mycoplasmal pneumonia in swine.

It is understood by those of skill in the art that variants of the M.hyo sequences can be employed in the compositions of the present invention. Such variants could vary by as much as 10-20% in sequence identity and still retain the antigenic characteristics that render it useful in immunogenic compositions. Preferably, the M.hyo variants have at least 80%, preferably at least 85%, more preferably at least 90%, even more preferably at least 95% sequence identify with the full-length genomic sequence of the wild-type M.hyo strain. The antigenic characteristics of an immunological composition can be, for example, estimated by the challenge experiment as provided in the Examples. Moreover, the antigenic characteristic of a modified M.hyo antigen is still retained when the modified antigen confers at least 70%, preferably 80%, more preferably 90% of the protective immunity as compared to the wild-type M.hyo protein.

In one embodiment, M.hyo soluble p46 antigen is included in the compositions of the invention at a final concentration of about 1.5 μg/ml to about 10 μg/ml, preferably at about 2 μg/ml to about 6 μg/ml. It is noted that p46 is the protein used for the M.hyo potency test (see example section below). In another embodiment, the M.hyo antigen can be included in the compositions at a final amount of about 5.5% to about 35% of the M.hyo whole culture protein A-treated supernatant.

The M.hyo soluble preparation is both safe and efficacious against M.hyo and is suitable for single dose administration. In addition, Applicants have surprisingly discovered that the M.hyo soluble preparation can be effectively combined with antigens from other pathogens, including PCV2 and PRRS virus, without immunological interference between the antigens. This makes the M.hyo soluble preparation an effective platform for multivalent vaccines, including the PCV2/M.hyo/PRRS combination vaccine of this invention. The PCV2 and PRRS virus antigens may be given concurrently with the M.hyo composition (i.e., as three separate single vaccines), but preferably the M.hyo soluble preparation and the PCV2 antigen are combined together in the form of a ready-to-use liquid composition. This ready-to-use PCV2/M.hyo liquid composition can then be combined with the PRRS virus antigen such that all antigens can be administered simultaneously to the pig. In some embodiments, the PRRS virus antigen is in a lyophilized state and the PCV2/M.hyo liquid composition can be used to re-hydrate the lyophilized PRRS virus antigen, thereby forming the trivalent composition.

In one embodiment, the immunogenic PCV2/M.hyo/PRRS compositions of the present invention include at least one additional antigen. In one embodiment, the at least one additional antigen is protective against a microorganism that can cause disease in pigs.

In some embodiments, the at least one additional antigen component is protective against bacteria, viruses, or protozoans that are known to infect pigs. Examples of such microorganisms include, but are not limited to, the following: porcine parvovirus (PPV), *Haemophilus parasuis, Pasteurella multocida, Streptococcum suis, Staphylococcus hyicus, Actinobacilllus pleuropneumoniae, Bordetella bronchiseptica, Salmonella choleraesuis, Salmonella enteritidis, Erysipelothrix rhusiopathiae, Mycoplama hyorhinis, Mycoplasma hyosynoviae, leptospira bacteria, Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmissable Gastroenteritis, or combinations thereof.

In one embodiment, a PCV2/M.hyo component of the trivalent vaccine according to the present invention is provided as a ready-to-use in one bottle liquid composition. Such a ready-to-use composition requires no mixing of separate PCV2 and M.hyo monovalent vaccines, so there is no risk of contamination or additional labor associated with mixing and no requirement to use the mixture within a few hours. Also, a one-bottle PCV2/M.hyo component cuts waste and refrigerator storage space in half.

In some embodiments, the PCV2 antigen component of an PCV2/M.hyo/PRRS combination vaccine is in the form of a chimeric type-1-type 2 circovirus. The chimeric virus includes an inactivated recombinant porcine circovirus type 1 expressing the porcine circovirus type 2 ORF2 protein. Chimeric porcine circoviruses and methods for their preparation are described in WO 03/049703 A2, and also in U.S. Pat. Nos. 7,279,166 and 7,575,752, which are incorporated herein by reference in their entirety.

In one embodiment, the full-length DNA sequence of the genome of the chimeric PCV1-2 virus corresponds to SEQ ID NO: 5. or variants thereof, as described below. In another embodiment, the immunogenic ORF2 capsid gene of the chimeric PCV1-2 virus corresponds to SEQ ID NO: 6. In a further embodiment, the amino acid sequence of the immunogenic ORF2 protein expressed by the chimeric PCV1-2 virus corresponds to SEQ ID NO: 7.

In yet another embodiment, the full-length DNA sequence of the genome of the chimeric PCV1-2 virus corresponds to SEQ ID NO: 8. In one embodiment, the immunogenic ORF2 capsid gene of the chimeric PCV1-2 virus corresponds to SEQ ID NO: 9. In a further embodiment, the amino acid sequence of the immunogenic ORF2 protein expressed by the chimeric PCV1-2 virus corresponds to SEQ ID NO: 10.

However, the PCV2 ORF2 DNA and protein of the chimeric PCV1-2 virus are not limited to the sequences described above sincePCV2 ORF2 DNA and protein is a highly conserved domain within PCV2 isolates.

In some embodiments, the PCV2 antigen component of an M.hyo/PCV2/PRRS combination vaccine is in the form of a recombinant ORF2 protein. In one embodiment, the recombinant ORF2 protein is expressed from a baculovirus vector. Alternatively, other known expression vectors can be used, such as including, but not limited to, parapox vectors.

In one embodiment, the recombinant PCV2 ORF2 protein is that of SEQ ID NO: 11, which is encoded by SEQ ID NO: 12 (GenBank Accession No. AF086834). In another embodiment, the recombinant ORF2 protein is that of SEQ ID NO: 13, which is encoded by SEQ ID NO: 14. In yet another embodiment, the recombinant ORF2 protein corresponds to SEQ ID NO: 15. In still another embodiment, the recombinant PCV2 ORF2 protein corresponds to SEQ ID NO: 7. In a still further embodiment, the recombinant PCV2 ORF2 protein corresponds to SEQ ID NO: 10.

However, the present invention is not limited to the particular ORF2 DNA and protein sequences described above. Since PCV2 ORF2 DNA and protein is a highly conserved domain within PCV2 isolates, any PCV2 ORF2 is highly likely to be effective as the source of the PCV2 ORF2 DNA and/or polypeptide as used in the chimeric PCV1-2 virus or in the recombinant PCV2 protein.

An example of a suitable PCV2 isolate from which the PCV2 ORF2 DNA and protein sequences can be derived is PCV2 isolate number 40895 (deposited in the ATCC on Dec. 7, 2001 and assigned ATCC Patent Deposit Designation PTA-3914). The genomic (nucleotide) sequence of the PCV2 isolate number 40895 is available under GenBank accession number AF264042. Other examples of suitable PCV2 isolates from which the PCV2 ORF2 DNA and protein sequences can be derived include, but are not limited to, the following: Imp.999, Imp.1010-Stoon, Imp.1011-48121, and Imp.1011-48285. The GenBank accession numbers of the genomic sequences corresponding to these PCV2 isolates are AF055391, AF055392, AF055393 and AF055394, respectively.

In some forms, immunogenic portions of PCV2 ORF2 protein are used as the antigenic component in the composition. For example, truncated and/or substituted forms or fragments of PCV2 ORF2 protein may be employed in the compositions of the present invention.

It is understood by those of skill in the art that variants of the PCV2 sequences can be employed in the compositions of the present invention. Such variants could vary by as much as 10-20% in sequence identity and still retain the antigenic characteristics that render it useful in immunogenic compositions. Preferably, the PCV2 variants have at least 80%, preferably at least 85%, more preferably at least 90%, even more preferably at least 95% sequence identify with the full-length genomic sequence of the wild-type PCV2 isolate. The antigenic characteristics of an immunological composition can be, for example, estimated by the challenge experiment as provided in the Examples. Moreover, the antigenic characteristic of a modified PCV2 antigen is still retained when the modified antigen confers at least 70%, preferably 80%, more preferably 90% of the protective immunity as compared to the wild-type PCV2 ORF2 protein.

The PCV2 antigen component is provided in the immunogenic composition at an antigen inclusion level effective for inducing the desired immune response, namely reducing the incidence of or lessening the severity of clinical signs resulting from PCV2 infection.

In one embodiment, a chimeric PCV1-2 virus is included in the trivalent compositions of the invention at a level of at least $1.0 \leq RP \leq 5.0$, wherein RP is the Relative Potency unit determined by ELISA antigen quantification (in vitro potency test) compared to a reference vaccine. In another embodiment, a chimeric PCV1-2 virus is included in the composition of the invention at a final concentration of about 0.5% to about 5% of 20-times (20×) concentrated bulk PCV1-2 antigen.

In another embodiment, the PCV2 ORF2 recombinant protein is included in the trivalent compositions of the invention at a level of at least 0.2 μg antigen/ml of the final immunogenic composition (μg/ml). In a further embodiment, the PCV2 ORF2 recombinant protein inclusion level is from about 0.2 to about 400 μg/ml. In yet another embodiment, the PCV2 ORF2 recombinant protein inclusion level is from about 0.3 to about 200 μg/ml. In a still further embodiment, the PCV2 ORF2 recombinant protein inclusion level is from about 0.35 to about 100 μg/ml. In still another embodiment, the PCV2 ORF2 recombinant protein inclusion level is from about 0.4 to about 50 μg/ml.

In one embodiment, a trivalent immunogenic composition of the present invention includes the inventive combination of at least one M.hyo soluble antigen (e.g., two or more), a porcine circovirus type 2 (PCV2) antigen, and a PRRS virus antigen. In another embodiment, the composition elicits a protective immune response in a pig against M.hyo, PCV2 and PRRS virus.

In one embodiment, a PCV2/M.hyo/PRRS combination vaccine is provided as a single-dose, 2-bottle vaccine. For example, in some embodiments, a PCV2/M.hyo combination is provided as a stable liquid composition in a first bottle and a PRRS virus is provided in a lyophilized state in a second bottle. In some embodiments, additional porcine antigens can be added to either the first or the second bottle.

In one embodiment, the PRRS virus component is provided as a lyophilized, genetically modified live virus. Prior to administration, the PCV2/M.hyo liquid from a first bottle can be used to re-hydrate the PRRS virus in a second bottle so that all three antigens can be administered to the animal in a single-dose. It is noted that although PCV2/M.hyo/PRRS combination vaccines currently exist, they are provided as a single-dose, 3-bottle vaccine which requires the simultaneous administration of three separate vaccines (e.g., Ingelvac CircoFLEX®, Ingelvac MycoFLEX® and Ingelvac®PRRS MLV).

The PRRS etiological agent was isolated for the first time in The Netherlands, and named as Lelystad virus. This virus was described in WO 92/21375 (Stichting Centraal Diegeneeskundig Instituut). An isolate of the European PRRS virus was deposited in the Institut Pasteur of Paris, number 1-1102. The North American type was isolated almost simultaneously with the isolation of the European type virus, and is described in WO-93/03760 (Collins et al.) An isolate of the North American type virus was deposited in the American Type Culture Collection (ATCC), number VR-2332.

Different strains have been isolated from both the European and North American virus types. WO 93/07898 (Akzo) describes a European strain, and vaccines derived from it, deposited in CNCM (Institut Pasteur), number 1-1140. Also, WO 93/14196 (Rhone-Merieux) describes a new strain isolated in France, deposited in CNCM (Institut Pasteur), number 1-1153. Furthermore, EP0595436 B1 (Solvay) describes a new North American type strain, more virulent than the one initially described, and vaccines thereof. This strain has been deposited in ATCC, but the deposit number is not detailed in the patent application. In addition, ES2074950 BA (Cyanamid Iberica) and its counterpart GB2282811 B2 describe a so-called "Spanish strain", that is different from other European and North American strains. This "Spanish strain" has been deposited in European Animal Cell Culture Collection (EACCC), number V93070108.

Suitable PRRS virus antigens for use in the PCV2/M.hyo/PRRS compositions of the present invention include North American PRRS virus isolates, Chinese PRRS virus strains, and European PRRS virus strains, as well as genetically modified versions of such isolates/strains. In one embodiment, the PRRS virus antigen component employed in the compositions according to the present invention is a North American PRRS virus.

In some embodiments, the PRRS virus antigen component employed in the compositions of this invention is the North American PRRS virus isolate designated P129 or a live, genetically modified version thereof. Preferably, the genetically modified PRRS virus is unable to produce a pathogenic infection yet is able to elicit an effective immunoprotective response against infection by the wild-type PRRS virus.

A genetically modified PRRS virus for use in the compositions of the invention can be produced from an infectious clone. The preparation of an infectious cDNA clone of the North American PRRS virus isolate designated P129 is described in U.S. Pat. No. 6,500,662 which is hereby incorporated fully by reference. The sequence of P129 cDNA is disclosed in Genbank Accession Number AF494042 and in U.S. Pat. No. 6,500,662.

In one embodiment, the nucleotide sequence of a non-virulent form of P129 for use in the compositions of the present invention is represented by SEQ ID NO: 16. However, the present invention is not limited to this sequence. This sequence and the sequences of other non-virulent forms of P129 are described in International Application No. PCT/IB2011/055003, filed Nov. 9, 2011, the contents of which (including any US National Stage filings based on this International Application) are incorporated herein by reference in their entirety. Preferably, the PRRS virus is modified to prevent downregulation of interferon-mediated function.

In other embodiments, the PRRS virus antigen component employed in the compositions of the invention is the PRRS virus isolate designated ISU-55. The ISU-55 isolate was deposited in the American Type Culture Collection (ATCC), under the accession number VR2430. The nucleotide sequence of the ORF2 to ORF5 genes of the ISU-55 isolate is represented by SEQ ID NO:17. The nucleotide sequence of the ORF6 and ORF7 genes of the ISU-55 isolate is represented by SEQ ID NO: 18.

Another suitable North American PRRS virus isolate which can be used in the compositions is ISU-12, which was deposited in the ATCC under the accession numbers VR2385 [3×plaque purified] and VR2386 [non-plaque purified]. Still other suitable North American PRRS virus isolates which can be employed in the compositions of this invention are the following: ISU-51, ISU-3927, ISU-1894, ISU-22 and ISU-79, which were deposited in the ATCC under the accession numbers VR2498, VR2431, VR2475, VR2429 and VR2474, respectively. Genetically modified versions of any of these ISU isolates can be employed in the compositions of this invention. These ISU isolates and the ISU-55 isolate are described in detail in the following U.S. patents to Paul, et al: U.S. Pat. Nos. 5,695,766, 6,110,467, 6,251,397, 6,251,404, 6,380,376, 6,592,873, 6,773,908, 6,977,078, 7,223,854, 7,264,802, 7,264,957, and 7,517,976, all of which are incorporated herein by reference in their entirety.

In still other embodiments, the PRRS virus antigen component employed in the compositions according to the present invention is the North American type deposited in the American Type Culture Collection (ATCC), number VR-2332 or a genetically modified version thereof. For example, the PRRS virus can be a modified live virus based on the isolate identified as ATCC VR2332, which is employed in INGELVAC® PRRS ATP and INGELVAC® PRRS MLV, from Boehringer Ingelheim Vetmedica, Inc.

In still other embodiments, the PRRS virus antigen component employed in the compositions of the present invention is a European PRRS virus isolate or Lelystad virus or a genetically modified version thereof. An example of a suitable PRRS virus strain is identified as deposit No. 1-1102, described above. Nucleotide and amino acid sequences corresponding to the 1-1102 deposit are described in U.S. Pat. No. 5,620,691 to Wensvoort et al, which is hereby fully incorporated herein by reference. The preparation of an infectious clone of a European PRRS virus isolate or Lelystad virus is described in U.S. Pat. No. 6,268,199 which is hereby fully incorporated herein by reference. Other examples of suitable PRRS virus isolates include, but are not limited to, those described above. Also, live, genetically modified versions of the PRRS virus isolates can be employed in the compositions of the present invention. An infectious clone can be used to re-create such live genetically modified organisms.

It is understood by those of skill in the art that variants of the PRRS virus sequences can be employed in the compositions of the present invention. Such variants could vary by as much as 10-20% in sequence identity and still retain the antigenic characteristics that render it useful in immunogenic compositions. Preferably, the PRRS virus variants have at least 80%, preferably at least 85%, more preferably at least 90%, even more preferably at least 95% sequence identify with the full-length genomic sequence of the wild-type PPRS virus isolate. The antigenic characteristics of an immunological composition can be, for example, estimated by challenge experiments. Moreover, the antigenic characteristic of a modified PRRS virus antigen is still retained when the modified antigen confers at least 70%, preferably 80%, more preferably 90% of the protective immunity as compared to the wild-type PRRS virus antigen.

In one embodiment, the PRRS virus antigen component is a genetically modified, live virus which is included in the compositions of the invention at a level of at least $2.1 \leq TCID_{50} \leq 5.2$, wherein $TCID_{50}$ is the tissue culture infectious dose 50% determined by antigen quantification (in vitro potency test)

The PCV2 antigen component of the PCV2/M.hyo/PRRS compositions of the invention can be in the form of a chimeric type-1-type 2 circovirus, the chimeric virus including an inactivated recombinant porcine circovirus type 1 expressing the porcine circovirus type 2 ORF2 protein. In another embodiment, the PCV2 antigen component of the PCV2/M.hyo/PRRS compositions of the invention is in the form of a recombinant ORF2 protein.

Suitable PCV2 antigens for use in the PCV2/M.hyo/PRRS compositions can be derived from any of the PCV2 isolates described above, as well as other PCV2 isolates. Suitable PCV2 antigens to be employed in the compositions of the invention include, but are not limited to, the PCV2 sequences described above and variants thereof.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Types of suitable adjuvants for use in the compositions of the present invention include the following: an oil-in-water adjuvant, a polymer and water adjuvant, a water-in-oil adjuvant, an aluminum hydroxide adjuvant, a vitamin E adjuvant and combinations thereof. Some specific examples of adjuvants include, but are not limited to, complete Freund's adjuvant, incomplete Freund's adjuvant, *Corynebacterium parvum, Bacillus* Calmette Guerin, aluminum hydroxide gel, glucan, dextran sulfate, iron oxide, sodium alginate, Bacto-Adjuvant, certain synthetic polymers such as poly amino acids and co-polymers of amino acids, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant (N,N-dioctadecyl-N',N'-bis(2-hydroxyethyl)-propanediamine), "REGRESSIN" (Vetrepharm, Athens, Ga.), paraffin oil, RIBI adjuvant system (Ribi Inc., Hamilton, Mont.), muramyl dipeptide and the like.

Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol.

Another example of an adjuvant useful in the compositions of the invention is SP-oil. As used in the specification and claims, the term "SP oil" designates an oil emulsion comprising a polyoxyethylene-polyoxypropylene block copolymer, squalane, polyoxyethylene sorbitan monooleate and a buffered salt solution. Polyoxyethylene-polyoxypropylene block copolymers are surfactants that aid in suspending solid and liquid components. These surfactants are commercially available as polymers under the trade name Pluronic®. The preferred surfactant is poloxamer 401 which is commercially available under the trade name Pluronic® L-121. In general, the SP oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution. In one embodiment, the SP-oil emulsion is present in the final composition in v/v amounts of about 1% to 25%, preferably about 2% to 15%, more preferably about 5% to 12% v/v.

Yet another example of a suitable adjuvant for use in the compositions of the invention is AMPHIGEN™ adjuvant which consists of de-oiled lecithin dissolved in an oil, usually light liquid paraffin.

Other examples of adjuvants useful in the compositions of the invention are the following proprietary adjuvants: Microsol Diluvac Forte® duel emulsion adjuvant system, Emunade adjuvant, and Xsolve adjuvant. Both the Emunade and Xsolve adjuvants are emulsions of light mineral oil in water, but Emunade also contains alhydrogel, and d,l-α-tocopheryl acetate is part of the XSolve adjuvant. A still further example of a suitable adjuvant for use in the compositions of the invention is ImpranFLEX™ adjuvant (a water-in-oil adjuvant). A still further example of a suitable adjuvant is a Carbomer (Carbopol®) based adjuvant. Preferred Carbopol® adjuvants include Carbopol® 934 polymer and Carbopol® 941 polymer.

In one embodiment, the adjuvant or adjuvant mixture is added in an amount of about 100 μg to about 10 mg per dose. In another embodiment, the adjuvant/adjuvant mixture is added in an amount of about 200 μg to about 5 mg per dose. In yet another embodiment, the adjuvant/adjuvant mixture is added in an amount of about 300 μg to about 1 mg/dose.

The adjuvant or adjuvant mixture is typically present in the vaccine composition of the invention in v/v amounts of about 1% to 25%, preferably about 2% to 15%, more preferably about 5% to 12% v/v.

Other "immunomodulators" that can be included in the vaccine include, e.g., one or more interleukins, interferons, or other known cytokines. In one embodiment, the adjuvant may be a cyclodextrin derivative or a polyanionic polymer, such as those described in U.S. Pat. Nos. 6,165,995 and 6,610,310, respectively.

A further aspect relates to a method for preparing an immunogenic composition according to the present invention. This method comprises i) culturing M.hyo in a suitable media over periods ranging from 18-144 hours; ii) subsequently inactivating the M. hyo culture; iii) harvesting the inactivated culture fluid, wherein the inactivated culture fluid comprises an M.hyo whole cell preparation comprising both a soluble liquid fraction and insoluble cellular material; iv) separating the soluble liquid fraction from the insoluble cellular material; v) substantially removing both IgG and antigen/immunoglobulin immunocomplexes from the separated soluble liquid fraction to form a soluble portion of the M.hyo whole cell preparation; and vi) subsequently combining the soluble portion of the M.hyo whole cell preparation with a PCV2 antigen and a PRRS virus antigen. In some embodiments, step vi) includes combining a ready-to-use liquid composition including both the PCV2 antigen and the M.hyo soluble portion with a lyophilized PRRS virus antigen.

An example of a suitable media for culturing M.hyo is PPLO Broth (*Mycoplasma* Broth Base), which when supplemented with nutritive enrichments, is used for isolating and cultivating *Mycoplasma*.

In some embodiments, the culture of M.hyo is grown until late log phase growth, after which the culture is inactivated. In some other embodiments, the culture is inactivated by raising the pH (e.g., to about 7.8). This occurs by exposing the production culture to an inactivation agent, such as binary ethylenimine (BEI). The BEI is generated in situ during incubation of L-bromoethylamine hydrobromide (BEA) in the production culture. Subsequently, the pH of the inactivated culture is neutralized, such as by adding an equivalent amount of an agent that neutralizes the inactivation agent within the solution. In some embodiments, the inactivation agent is BEI and the neutralization agent is sodium thiosulfate. In one embodiment, the pH of the inactivated culture is adjusted to about 7.4 by adding sodium thiosulfate.

In some embodiments, the soluble liquid fraction of the M.hyo whole cell preparation is separated from the insoluble cellular material using conventional methods. In one embodiment, this separation is by a filtration step. In another embodiment, this separation is by a centrifugation step. In yet another embodiment, the separation is by a precipitation step.

In one embodiment, the soluble liquid fraction of an inactivated, neutralized M.hyo whole cell preparation is treated with Protein A resin to substantially remove both the IgG and antigen/immunoglobulin immunocomplexes therein. In other embodiments, Protein G resin can be used to substantially remove both the IgG and antigen/immunoglobulin immunocomplexes contained in the soluble liquid fraction. Methods for removing both IgG and antigen/immunoglobulin immunocomplexes with either Protein A or Protein G resins are well known in the art.

According to a further aspect, the method for preparing a trivalent immunogenic composition according to the present invention comprises preparing the soluble M.hyo antigen as described above and mixing this with a PCV2 antigen, a PRRS virus antigen, a suitable adjuvant, and one or more pharmaceutically-acceptable carriers. This method optionally includes combining the PCV2 antigen and soluble M.hyo antigen to form a divalent composition and subsequently adding this divalent composition to a monovalent PRRS virus antigen composition to form the trivalent composition.

A further aspect of the present invention relates to a kit. A "kit" refers to a plurality of components which are grouped together. In one embodiment, a kit according to the present invention includes a first bottle (or other suitable receptable) comprising a composition including both a PCV2 antigen and the soluble portion of a *Mycoplasma hyopneumoniae* (M.hyo) whole cell preparation, wherein the soluble portion of the M.hyo preparation is substantially free of both (i) IgG and (ii) antigen/immunoglobulin immunocomplexes; and a second bottle comprising PRRS virus antigen. In one embodiment, the kit further includes an instruction manual.

In some embodiments, the PCV2/M.hyo combination in the first bottle of the kit is provided as a ready-to-use liquid composition. In further embodiments, the PRRS virus antigen is in the form of a genetically modified, live virus which is provided in a lyophilized state. In such instances, the instruction manual will include the directions for re-hydrating the PRRS virus component in the second bottle with the liquid contents from the first bottle containing the PCV2/M.hyo combination. The instruction manual will also preferably include the directions to administer the combined contents from the first and second bottles to the pig.

In some embodiments, an immunogenic composition according to this invention is administered to pigs having maternally derived antibodies against at least one of M.hyo, PCV2 and PRRS virus. In other embodiments, an immunogenic composition of the present invention is administered to pigs having maternally derived antibodies against M.hyo, PCV2, and PRRS virus.

In some embodiments, a trivalent immunogenic composition according to the present invention is administered to a piglet aged 3 weeks or older. However, it is contemplated that a trivalent vaccine composition according to the invention may also be used to re-vaccinate gilts pre-breeding. As is known in the art, a gilt is a female pig that has never been pregnant. Vaccinated gilts will pass maternally derived antibodies onto their suckling newborns via colostrum.

It is further contemplated that a trivalent vaccine according to the invention can be used to annually re-vaccinate breeding herds. Preferably, a trivalent vaccine according to the present invention is administered to pigs (e.g., piglets or gilts) in one dose. In one embodiment, a multivalent vaccine according to the present invention does not require mixing of separate PCV2 and M.hyo monovalent vaccines prior to administration, i.e., the PCV2/M.hyo component is provided as a ready-to-use formulation contained in one bottle. In another embodiment, a multivalent formulation requires mixing of a divalent PCV2/M.hyo vaccine contained in a first bottle with a monovalent PRRS vaccine contained in a second bottle. Optionally, additional antigens can be added to either of these bottles.

In some embodiments, the onset of immunity is from 2-3 weeks post-vaccination with a trivalent vaccine composition according to the present invention. In other embodiments, the duration of immunity is about 17-23 weeks post-vaccination with a trivalent vaccine composition according to the present invention.

The following examples set forth preferred materials and procedures in accordance with the present invention. However, it is to be understood that these examples are provided by way of illustration only, and nothing therein should be deemed a limitation upon the overall scope of the invention.

EXAMPLES

Example 1

*Mycoplasma hyopneumoniae* Production Methods for PCV2 Combinable M.Hyo Antigen M.Hyo Fermentation and Inactivation Media for seed scale and antigen production was prepared as follows. Porcine heart derived Pleuropenumonia-like Organism (PPLO) Broth (BD Biosciences catalog No. 21498) was made per manufacturer's directions (i.e., 21 g/L) and yeast extract solution was made at 21 g/L in USP. Yeast extract solution was then added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. The medium was inoculated with a 10% v:v of a log phase culture of *M. hyopeumoniae* (strain P-5722-3). The culture was held at 37° C. and pH and dO were maintained at 7.0 and 25%, respectively. At late log phase growth, the culture was inactivated was inactivated by binary ethylenimine (BEI), an aziridine compound, produced from 2-bromoethylamine hydrobromide. Specifically, the inactivation occurred by raising the pH to 7.8 by adding 2-bromoethylaminehydrobromide (BEA) to a final concentration of 4 mM and incubating for 24 hours. The BEI was neutralized by addition of sodium thiosulfate at a 1:1 molar ratio followed by additional 24 hour incubation. The inactivated culture fluid was held at 2-8° C. until further processing.

Example 2

Chimeric Porcine Circovirus (cPCV)1-2 Production Methods

The cPCV1-2 was constructed by cloning the immunogenic capsid gene of the pathogenic porcine circovirus type 2 (PCV2) into the genomic backbone of the nonpathogenic porcine circovirus type 1 (PCV1). The procedure for construction of the chimeric DNA clone is described, for example, in U.S. Pat. No. 7,279,166, which is incorporated herein by reference in its entirety. An infectious stock of the chimeric virus was acquired from Dr. X. J. Meng, Virginia Polytechnic Institute and State University, Blacksburg, Va., and was used to infect Porcine Kidney (PK)-15 cells grown in Minimum Essential Medium (MEM) supplemented with 0.05% lactalbumin hydrolysate (LAH), 30 μg/mL gentamicin sulfate, and 5% fetal bovine serum. The resulting cPCV1-2 infected PK-15 cells were further expanded by serial passing four more times using the same growth medium except with 2-3% fetal bovine serum. The fifth passage was frozen, thawed and filtered, and the resulting lysates were used to prepare a pre-master seed and subsequent master seed.

The medium which was used for producing virus seeds was the same as that used in producing virus stock. For the growth medium, MEM, OptiMEM, or equivalent is the basal medium which can be used for planting the PK-15 cell line for outgrowth. The growth medium can be supplemented with up to 10% bovine serum, up to 0.5% lactalbumin hydrolysate, up to 0.5% bovine serum albumin, and up to 30 μg/mL gentamicin. For the virus propagation medium, MEM, OptiMEM, or equivalent is used. The virus propagation medium can be supplemented with up to 0.5% lactalbumin hydrolysate, up to 2% bovine serum, up to 0.5% bovine serum albumin, and up to 30 μg/mL gentamicin. Up to 5 g/L glucose and up to 5 mmol/L L-glutamine can be added to the growth medium and/or the virus propagation medium as required to sustain the cells.

The cPCV1-2 master seed virus are added to a cell suspension of PK-15 cells and adsorbed for up to 3 hours. Seed virus is diluted in growth basal medium to provide a multiplicity of infection (MOI) of 0.1-0.0001.

Cultures of PK-15 cells are initially inoculated with working seed virus at the time of cell planting, or when cells reach approximately 20% to 50% confluency. This initial passage may be referred as "One-Step Infection Method" for the production of antigen stock, or may be further used for serial passages. For serial passages, the cPCV1-2 infected PK-15 cells are further expanded up to passage 7 by serial splits at the ratio of 1:5-20 for virus propagation. Culture medium containing an infected cell suspension from the previous passage serves as seed material for the next passage. The cPCV1-2 infected cells are incubated for three (3) to 14 days for each passage at 36±2° C. when cells reach ≥90% confluency. The cPCV1-2 virus causes observable cytopathic changes during viral replication. At harvest, rounding of cells and considerable floating debris is observed. Cultures are also observed for visual evidence of bacterial or fungal contamination. The incubation time between harvests for the cPCV antigen is provided in Table 1 below:

TABLE 1

| Minimum and Maximum Times for Harvesting cPCV Antigen | | |
|---|---|---|
| Method | Minimum/ Maximum Time | Temperature Range |
| One-Step Infection | 5 to 16 days | 36 ± 2° C. |
| Serial Passage (MSV + 3 to MSV + 7) | 16 to 36 Days | 36 ± 2° C. |

The cPCV1-2 culture fluids are harvested into sterile vessels and are sampled for *mycoplasma* testing using known methods. Multiple harvests may be conducted from roller bottles, bioreactors and perfusion vessels.

Prior to inactivation of the harvested cPCV1-2 virus, one or more antigen lots may be concentrated (e.g., up to 60×) by ultrafiltration. The concentrates may be washed with balanced salt solution to reduce serum proteins.

The method of inactivation, attenuation, or detoxification of the cPCV1-2 virus will now be described. After cPCV antigen concentration, Beta-propiolactone (BPL) is added to the pooled cPCV1-2 viral material to obtain an approximate concentration of 0.2% v/v. The pooled viral fluids are then agitated for a minimum of 15 minutes and then the inactivating bulk antigen fluids are transferred to a second sterile vessel. The transferred antigen fluids are maintained at 2-7° C., with constant agitation, for a minimum of 24 hours. After a minimum of 24 hours, a second addition of 0.2% v/v of BPL is added to the pooled suspension. The contents are subsequently agitated, transferred to a third vessel, and maintained at 2-7° C., with constant agitation, for an additional time of not less than 84 hours. In general, the total inactivation time is not less than 108 hours and not more than 120 hours. The inactivation method is summarized in Table 2 below.

TABLE 2

| Inactivation Method | | | |
|---|---|---|---|
| Inactivant | Final Concentration | Temp. Range | Time-Hours (Min/Max) |
| Beta-propiolactone (BPL) | 0.4% v/v (2 × 0.2% v/v additions) | 2-7° C. (w/Agitation) | 108-120 |

The inactivation is terminated by the addition of a final concentration of not more than 0.1 M solution of sodium thiosulfate. The pH of the inactivated antigen stock is adjusted to about 6.8 using NaOH or HC 1. Following inactivation, a representative sample is taken from the pool and tested for completion of inactivation. The inactivated cPCV1-2 antigen product is standardized to a meet a target of greater than 1.0 RP as measured via potency ELISA.

Example 3

Down Stream Processing of M.Hyo Antigens and Analytical Testing of these Processed Antigens Down Stream Processing of M.Hyo Antigens:

Inactivated fermentation fluid (prepared as described above in Example 1) was treated for each indicated group as follows. These processed M.hyo antigens were employed in Example 4 below.

T02: (Whole Bulk) Not processed.

T03: (10×UF concentrated) Concentrated via tangential flow filtration via a 100 KDa molecular weight cutoff membrane (hollow fiber). Final volume reduction was equal to 10×.

T04 & T05: (10×UF concentrated & centrifuged) Concentrated *mycoplasma* cells (from T03) were collected and washed one time with PBS via centrifugation at ~20,000×g (Sorvall model RC5B).

T06 & T07: (10× centrifuged) Inactivated fermentation fluid was centrifuged at ~20,000×g (Sorvall RC5B) and washed one time by resuspending the cells in PBS followed by an additional centrifugation. Final volume reduction was equal to 10×.

T08: (10× centrifuged & Heated) *Mycoplasma* cells were concentrated and washed per T06 and heated to 65° C. for 10 minutes.

T09: (Cell-free supernatant) Supernatant collected from the first centrifugation as described for T06 was filter sterilized through a 0.2 micron filter (Nalgene).

T10: (Cell-free supernatant-Protein-A treated) Sterile supernatant (prepared per T09) was mixed with Protein A resin (Protein A Sepharose, Pharmacia Inc) at a 10:1 volume ratio for 4 hours. Resin was removed sterile filtration and filtered fluid was stored at 2-8° C. This process uses post-fermentation "downstream" protein A treatment to remove antibodies and immunocomplexes. Although the present invention does not preclude upstream protein A treatment, the present inventors have found that in the case of M.hyo, upstream protein A treatment of the growth media led to p46 results which were lower and inconsistent as compared to untreated media (data not shown).

Analytical Testing of M.Hyo Downstream Processed Antigens

The downstream processed M.hyo antigens preparations (prepared as described above) were tested for the recovery of M.hyo specific p46 antigen, and the presence of PCV2 antibody. In addition, these M.hyo antigen preparations were tested for the presence of Torque Teno Virus (TTV), including genotype 1 (g1TTV) and genotype 2 (g2TTV). The results are presented below in Table 3.

TABLE 3

Characterization of *M. hyo* Downstream Processed Antigens

| Treatment | Bulk *M. Hyo* p46 RU/mL | PCV2 ab S/P ratio | qPCR DNA g1TTV | qPCR DNA g2TTV |
|---|---|---|---|---|
| Whole bulk | 809 | 0.248 | 1.00E+03 | 1.78E+03 |
| 10x UF concentrated | 6666 | 0.819 | 1.00E+03 | 9.94E+03 |
| 10x UF conc. + Centrifuge | 614 | 0.019 | 0 | 0 |
| 10x Centrifuged | 763 | −0.015 | 1.90E+02 | 1.91E+02 |
| 10x Centrifuged + Heated | 690 | −0.012 | 0 | 2.07E+02 |
| Cell-free supe | 719 | 0.242 | 4.20E+02 | 3.23E+03 |
| Cell-free supe (Prot A) | 826 | −0.014 | 0 | 2.06E+03 |

With reference to Table 3 above, recovery of the M.hyo-specific p46 antigen was demonstrated for each of the M.hyo downstream processed antigen preparations. In addition, the following treatments successfully removed PCV2 antibody: 10×UF concentrated & centrifuged, 10× centrifuged, 10× centrifuged & heated and Cell-free supernatant (Protein-A treated). With respect to TTV, the following treatments successfully removed g1TTV: 10×UF concentrated & centrifuged, 10× centrifuged & heated, and Cell-free supernatant (Protein-A treated). Only the treatment designated 10×UF concentrated & centrifuged removed g2TTV. Torque teno virus isolates, including genotypes 1 and 2 are described in US20110150913, which is incorporated herein by reference in its entirety.

Since it is known in the art that Protein A binds IgG, it is understood by those of ordinary skill in the art that not only PCV2 antibody, but other swine antibodies, including PRRS antibody, HPS antibody, and SIV antibody will be effectively removed by the Protein-A treatment. This makes the Cell-free Protein-A treated M.hyo supernatant of this invention compatible not only with PCV2 antigen, but also with other porcine antigens due to the lack of immunological interference between the antigens. Additionally, the removal of the non-protective cell debris and removal of the immunoglobulin and antigen/immunoglobulin complexes is reasonably expected to make a safer vaccine.

Example 4

Preparation of M.Hyo Experimental Vaccine Formulations

All experimental M.hyo vaccines were formulated with a final concentration of 5% Amphigen adjuvant. In addition, all vaccines were standardized with a p46 ELISA and preserved with thimerosol. The experimental vaccine formulations were prepared with M.hyo antigens processed according to treatments T02-T10 above. In addition, Treatment T01 corresponded to a placebo (no M.hyo antigen, only 5% Amphigen adjuvant) whereas Treatment T11 is a positive control corresponding to an expired bacterin-based M.hyo vaccine (RespiSure-ONE®, Pfizer Animal Health). These formulations are described in Table 4 below.

TABLE 4

*M. hyo* Experimental Vaccine Formulations

| Treatment | IVP Serial* | Target p46 units/ds | M Hyo antigen (mL) | Adjuvant (mL) | Formulation Vol. (mL) |
|---|---|---|---|---|---|
| T01 | 123639 (Placebo) | 5% Amphigen only, No Antigen | | | |
| T02 | L100211A | 452 | 279.36 | 250 | 1000 |
| T03 | L100211B | 452 | 6.78 | 50 | 200 |
| T04 | L100211C | 452 | 73.62 | 50 | 200 |
| T05 | L100211D | 816 | 132.90 | 50 | 200 |
| T06 | L100211E | 452 | 59.24 | 50 | 200 |
| T07 | L100211F | 816 | 106.95 | 50 | 200 |
| T08 | L100211G | 452 | 65.51 | 50 | 200 |
| T09 | L100211H | 452 | 62.87 | 50 | 200 |
| T10 | L100211J | 452 | 54.72 | 50 | 200 |
| T11 | A827870 | Expired "RespiSure" vaccine | | | |

*Investigational Veterinary Product (IVP) Serial

Example 5

Evaluation of the In Vivo Efficacy of M.Hyo Vaccines with M.Hyo Antigens from Different Downstream Processes This study was conducted to evaluate the in vivo efficacy of *Mycoplasma hyopneumoniae* (M hyo) vaccines with M hyo antigens from different downstream processes (DSP). Pigs at 3 weeks of age were intramuscularly inoculated with a single dose of the different vaccine formulations described in Table 4 above. Sixteen animals were included in each of the treatment groups. Animals were challenged 21 days after vaccination with a virulent M.hyo field isolate. Animals were necropsied 28 days after challenge and the lungs were removed and scored for consolidation consistent with M.hyo infection. The primary criterion for protection against M.hyo challenge was lung consolidation scores. It is generally accepted that there is a relationship between the size of the lung lesions caused by enzootic pneumonia and an adverse effect on growth rate. Table 5 below contains the lung lesion scores for the respective treatment groups. Statistical significance was determined by a Mixed Model Analysis of lung scores for each group.

TABLE 5

| Lung Lesion Results | | | | | | | |
|---|---|---|---|---|---|---|---|
| Treatment | Description | p46 RP Target/ Observed | % Lung Lesions Back Transformed LS Means | Range % Lung with Lesions | Contrast | p-value | Significant |
| T01 | Placebo (5% Amphigen) | N/A | 11.7 | 1.2-44.3 | N/A | N/A | N/A |
| T02 | Whole bulk | 13/15.6 | 1.2 | 0.1-18.5 | T01 vs 02 | 0 | Yes |
| T03 | Whole bulk UF 10x | 13/11.9 | 0.3 | 0.0-2.8 | T01 vs 03 | 0 | Yes |
| T04 | UF 10x + Centrifuged | 13/28.1 | 5.9 | 0.0-40.5 | T01 vs 04 | 0.1589 | No |
| T05 | UF 10x + Centrifuged | 24/48.2 | 3.7 | 0.0-42.3 | T01 vs T05 | 0.0309 | Yes |
| T06 | 10x Centrifuged | 13/30.4 | 4.7 | 0.0-23.6 | T01 vs 06 | 0.0388 | Yes |
| T07 | 10x Centrifuged | 24/57.4 | 4.6 | 0.3-37.3 | T01 vs T07 | 0.0323 | Yes |
| T08 | 10x Centrifuged + Heat | 13/17.7 | 4.5 | 0.3-21.7 | T01 vs T08 | 0.0137 | Yes |
| T09 | Supernatant (no cells) | 13/14.1 | 1.4 | 0.0-33.0 | T01 vs T09 | 0.0004 | Yes |
| T10 | Supernatant + Prot A | 13/12.1 | 3.1 | 0.0-25.8 | T01 vs T10 | 0.0094 | Yes |
| T11 | Expired RSO | 13/12.5 | 2.2 | 0.1-32.1 | T01 vs T11 | 0.0009 | Yes |

With reference to Table 5 above, the results with M.hyo antigens from different downstream processes indicated that all experimental vaccines except T04 significantly differed from the placebo. These M.hyo lesion results are depicted graphically in FIG. 1. As shown in FIG. 1, T04 gave unacceptable results. All other treatments differed significantly from the placebo (T01). The lung consolidation scores indicated that T02, T03 and T09-T11 gave the most efficacious protection against M.hyo challenge.

The p46 relative potency of the experimental vaccines was assessed by using a double antibody sandwich enzyme-linked immunosorbent assay (DAS ELISA). The p46 DAS ELISA results presented in Table 5 above indicate that all the experimental vaccines exceeded the target potency. In addition, the p46 relative potency was either maintained or increased during storage of the vaccines over a one-month period (data not shown). A perceived increase in potency over time was observed in centrifuged antigens with the exception of those antigens that were subjected to heat. While not wishing to be bound by any one theory, it is likely that cell "carcasses" are breaking up over time and released more of the membrane bound p46 antigen in the case of the centrifuged antigens.

Example 6

Evaluation of the Compatibility of the Experimental M.Hyo Vaccines with PCV2 Antigen This study was conducted to evaluate the compatibility of the M.hyo experimental vaccines with M hyo antigens from different downstream processes with PCV2 antigen. The M.hyo experimental vaccine formulations are described in Tables 4 and 5 above. The observed p46 relative potencies for these vaccines are described in Table 5 above. These M.hyo experimental vaccines were each combined with PCV2 antigen. In this example, the PCV2 antigen was a killed PCV Type 1-Type 2 chimeric virus (Fostera PCV) prepared as described above in Example 2. The chimeric virus was included in the compositions at an initial level of about 1.6≤RP, wherein the RP is the Relative Potency unit determined by PCV2 ELISA antigen quantification (in vitro potency test) compared to an efficacious reference vaccine.

Figure 2:
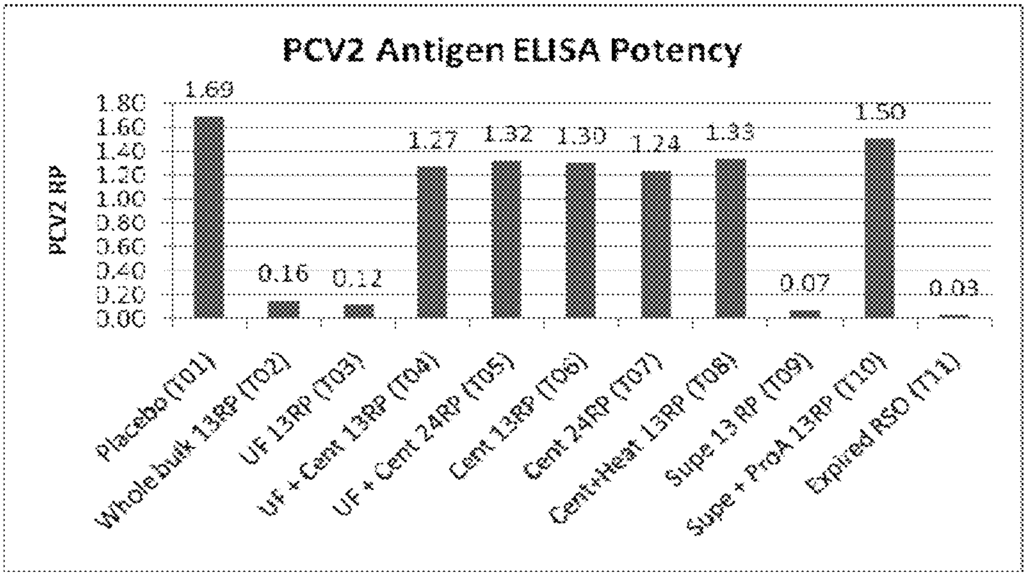
FIG. 2 is a graph showing the PCV2 antigen potency results (PCV2 antigen ELISA) of M.hyo vaccines in combination with killed PCV Type1-Type2 chimeric virus. The chimeric virus was included in the compositions at an initial level of about 1.6≤RP. The status of each sample is expressed as relative potency (RP).

The experimental M.hyo/PCV2 combination formulations were evaluated by PCV2 ELISA. The results are presented in FIG. 2. As shown in FIG. 2, only the M.hyo antigen preparations from the following downstream processes were compatible with the PCV2 antigen: Ultrafiltration & Centrifugation (T04 & T05), Centrifugation (T06 & T07), Centrifugation plus heat (T08) and Protein A-treated Supernatant (T10). Of these, the M.hyo Protein A-treated supernatant was the most compatible with PCV2 antigen when compared to the placebo control which included the chimeric virus and Amphigen adjuvant, but no M.hyo antigen. The level of chimeric PCV virus in the Protein-A treated supernatant was 1.5 RP as compared to 1.69 RP for the placebo. It was therefore concluded that there is no or minimal immunological interference between the Protein-A treated M.hyo soluble antigen preparation and PCV2 antigen of the chimeric virus.

The in vivo efficacy of the Protein-A treated M.hyo supernatant demonstrated in Example 5 above together with the results described in the present example indicated that the Protein-A treated supernatant was a potentially effective platform for M.hyo-PCV2 combinations.

Example 7

Evaluation of PCV2 Efficacy of a 1-Bottle PCV2/M.Hyo Combination Vaccine in Different Adjuvant Formulations This study was designed to evaluate the PCV2 efficacy in a 1-bottle PCV2/M.hyo combination vaccine in different adjuvant formulations. In this example, the PCV2 antigen was a killed PCV Type 1-Type 2 chimeric virus (Fostera PCV). The chimeric virus was combined with an M.hyo soluble antigen preparation that was substantially free of IgG (i.e., Protein A-treated supernatant).

Processing of Fluids:

Inactivated M.hyo fermentation fluid (described above in Example 1) was treated for each indicated group as follows. T02-T04: Whole fermentation fluid containing live *M. hyopneumoniae* cells (described above) was centrifuged at ~20,000×g (Sorvall RCSB) and the supernatant collected and sterilized through a 0.2 μM filter. rProtein A Sepharose (part number 17-5199-03, GE Healthcare) was packed into a 1 L chromatography column. After removal of the storage buffer and treatment with 2 column volumes of 1M acetic acid, the resin was equilibrated with 5 column volumes of 50 mM NaPO4/1M NaCl buffer, pH 7.04. Approximately 2 liters of the clarified/filtered *M. hyopneumoniae* antigen containing fluids were passed through the Protein A resin at a flow rate of 100 cm/hr. The flow through was collected and sterilized via 0.2 μM filter.

T05: This is a positive control corresponding to a Fostera PCV-like formulation (no M.hyo antigen). The level of the chimeric virus in this Fostera PCV-like formulation was approximately at Minimum Immunizing Dose (MID) formulation levels. The chimeric virus was included in the PCV2/M.hyo experimental vaccines at similar formulation levels.

All experimental PCV2/M.hyo vaccines were formulated with different adjuvant formulations. The experimental vaccine formulations were prepared with M.hyo antigens processed according to treatments T02-T04 above. In addition, Treatment T01 corresponded to a placebo (sterile saline).

All vaccines were standardized with a p46 ELISA and preserved with thimerosol. These experimental formulations are described in Table 6 below, wherein the symbol * indicates the M hyo antigen from global M hyo seed, Protein A treated supernatant and the symbol ** indicates Investigational Veterinary Product (IVP) serial.

TABLE 6

PCV2/*M. hyo* Experimental Vaccine Formulations Used for PCV2 Efficacy Study

| Treatment | IVP Serial** | PCV1-2 Ag | *M Hyo** Ag | Adjuvant | Other |
|---|---|---|---|---|---|
| T01 | 87-244-DK (Placebo) | | NA | | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | L0611RK04 | | NA | 20% SLCD | |

Pigs at 3 weeks of age were intramuscularly inoculated with a single dose of the different vaccine formulations described in Table 6 above. Sixteen animals were included in each of the treatment groups. Animals were challenged 21 days after vaccination with a virulent PCV2 field isolate.

Figure 3:
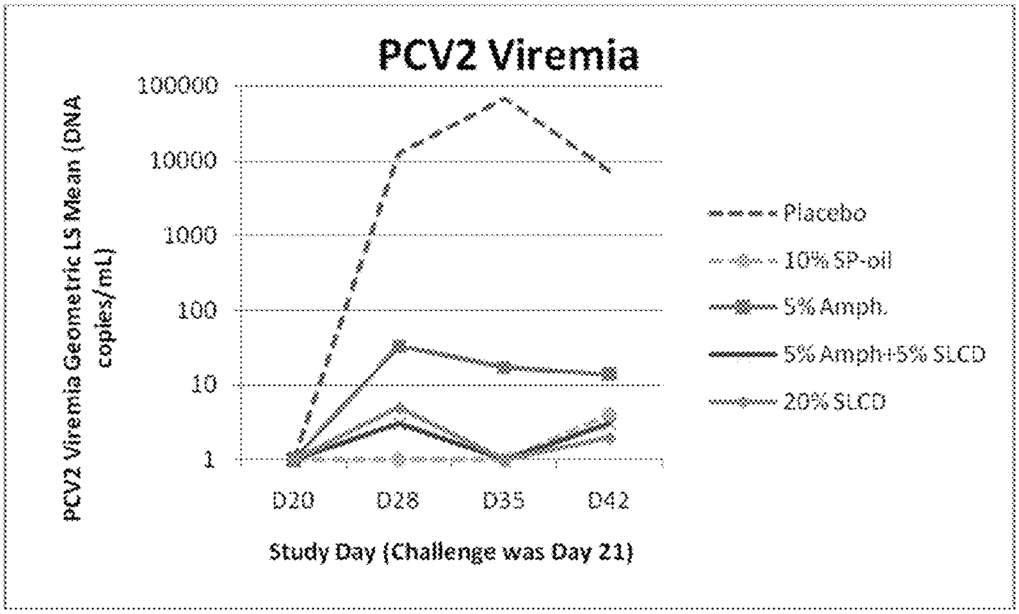
FIG. 3 is a graph showing the PCV2 viremia results (PCV2 Quantitative PCR) observed with PCV/M.hyo vaccine formulations employing different adjuvant platforms.

FIG. 3 is a graph showing the PCV2 viremia results (PCV2 Quantitative PCR) observed with the different adjuvant platforms. It is noted that PCV2 viremia was used as the primary efficacy variable. The PCV2 viremia results are presented as DNA copies/ml. As shown in FIG. 3, all treatments had significantly less viremia compared to the placebo on days 28, 35 and 42 (challenge was day 21). The 10% SP-oil adjuvant had significantly less viremia compared to 5% Amphigen at Days 28 and 35. The 5% Amphigen plus 5% SLCD adjuvant had significantly less viremia compared to 5% Amphigen at Days 28 and 35. The 20% SLCD adjuvant platform had significantly less viremia compared to 5% Amphigen at Days 28, 35 and 42.

PCV2 Serology, PCV2 fecal shed, PCV2 nasal shed, Cell Mediated Immune (CMI) responses, lymphoid depletion, and Immunohistochemistry (IHC) were also monitored as secondary efficacy variables. These results will now be described below.

Figure 4:
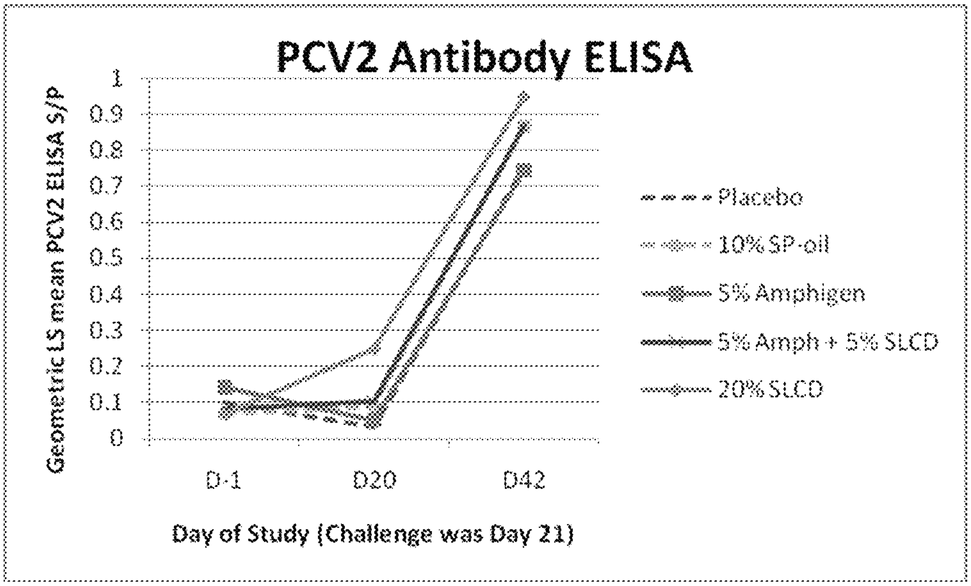
FIG. 4 is a graph showing the PCV2 antibody ELISA (S/P) serological results observed with PCV/M.hyo vaccine formulations employing different adjuvant platforms on days 1, 20, and 42 of challenge.

FIG. 4 is a graph showing the PCV2 ELISA results on days 1, 20 and 42 of the study (challenge was day 21). The status of each sample was expressed as a sample to positive ratio (S/P). As shown in FIG. 4, 20% SLCD was the only treatment which was significantly different from the placebo (T01) at both day 20 and day 42. Also, 5% Amphigen was the only treatment not significantly different from the placebo at day 20.

Figure 5:
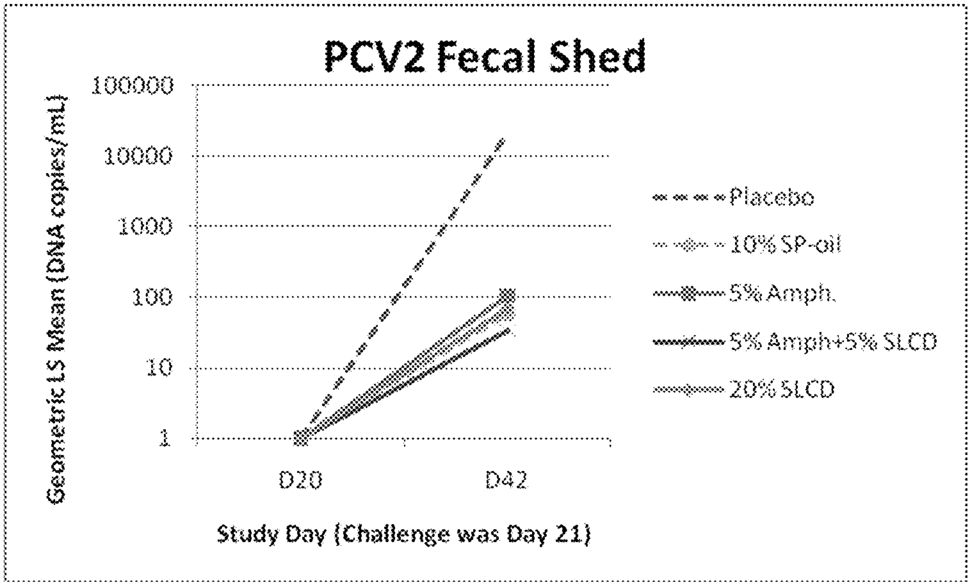
FIG. 5 is a graph showing the PCV2 fecal shed obtained with the T02-T04 treatments described in Example 7 vs. a placebo (T01). The results are expressed as PCV2 DNA copies/ml.

FIG. 5 is a graph showing the PCV2 fecal shed obtained with the T02-T04 treatments vs. the placebo (T01). These results are expressed as PCV2 DNA copies/ml. The results in FIG. 5 indicate that all treatments had significantly less fecal shed when compared to the placebo at day 42. In addition, 5% Amphigen & 5% SLCD (T04) had significantly less fecal shed as compared to 5% Amphigen (T03) at day 42. No other treatment differences were noted.

Figure 6:
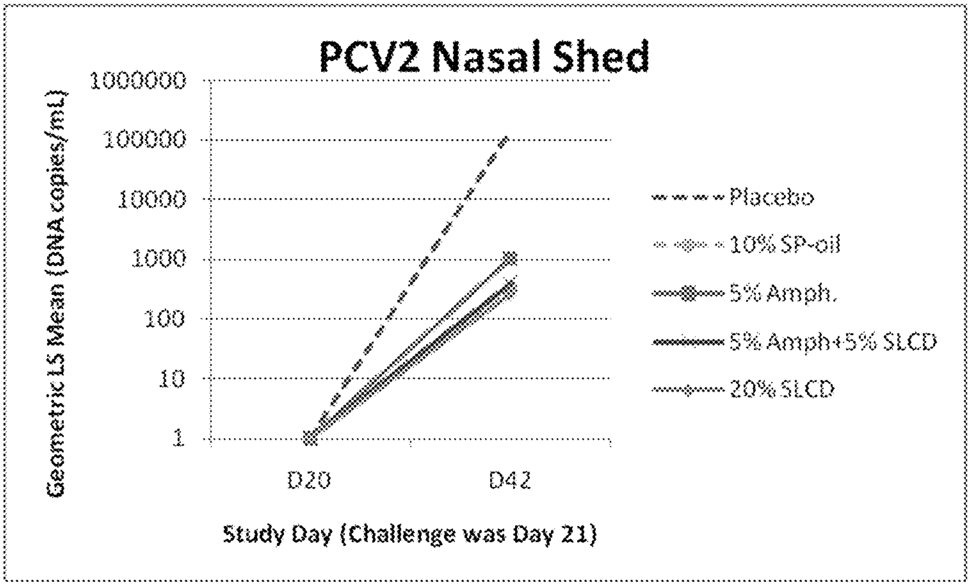
FIG. 6 is a graph showing the PCV2 nasal shed obtained with the T02-T04 treatments described in Example 7 vs. the placebo (T01). The results are expressed as PCV2 DNA copies/ml.

FIG. 6 is a graph showing the PCV2 nasal shed obtained with the T02-T04 treatments vs. the placebo (T01). These results are expressed as PCV2 DNA copies/ml. The results in FIG. 6 indicate that all treatments had significantly less nasal shed when compared to the placebo at day 42. In addition, 20% SLCD (T05) had significantly less nasal shed compared to 5% Amphigen (T03) at day 42. No other treatment differences were noted.

Figure 7A:
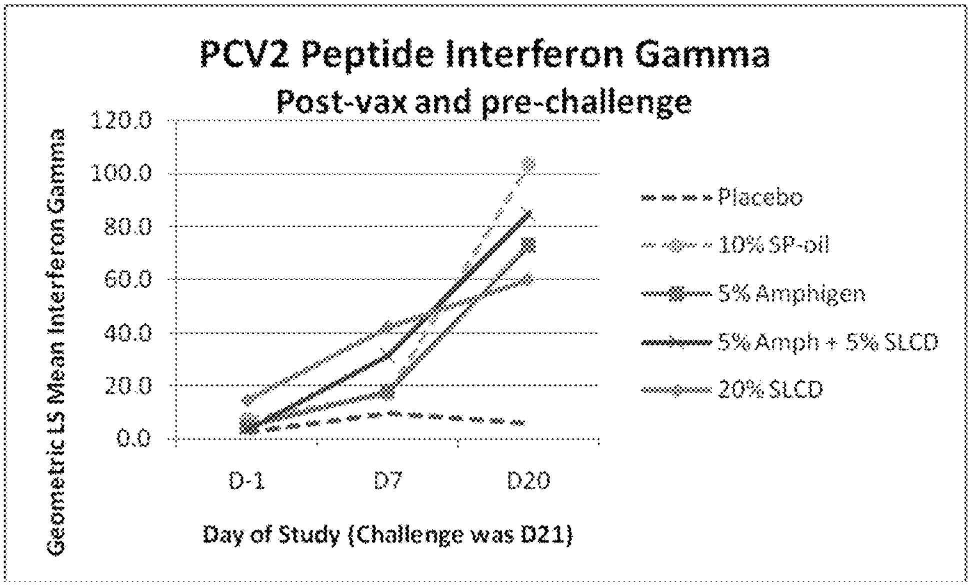
FIGS. 7 (A & B) are graphs showing the results of an interferon-gamma (IFN-γ) test that measures PCV2-specific cellular mediated immune (CMI) responses. The results of pos-vaccination/pre-challenge are presented in FIG. 7A, and the results of post-vaccination/post-challenge are presented in FIG. 7B. Stimulation of $5\times10^6$ cells was considered significant.
Figure 7B:
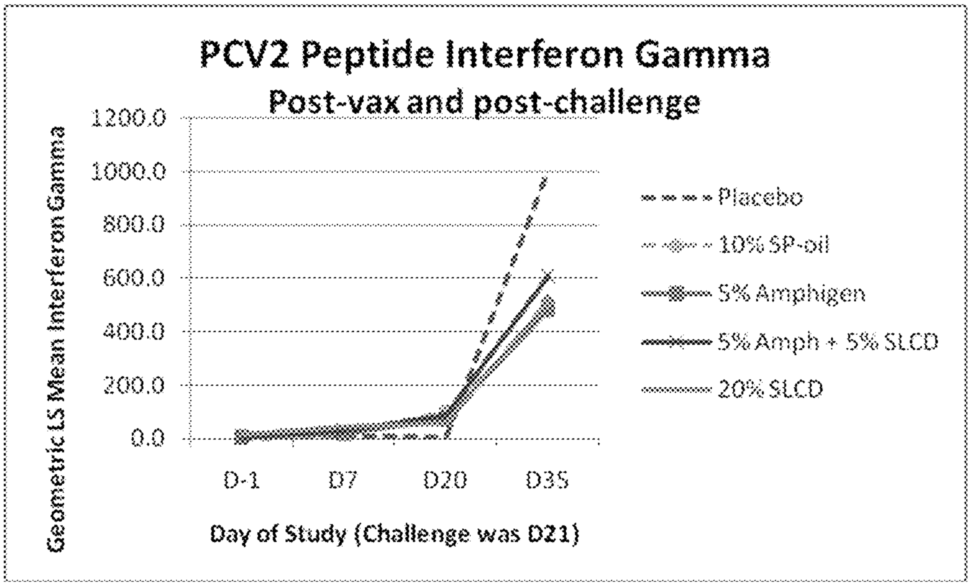

FIGS. 7 (A & B) are of two graphs showing the results of an interferon-gamma (IFN-γ) test that measures PCV2-specific cellular mediated immune (CMI) responses. The CMI results are shown post-vaccination/pre-challenge (FIG. 7A), and post-vaccination/post-challenge (FIG. 7B). In these graphs, stimulation of $5\times10^6$ cells was considered significant ( . . . ). All PCV2/M.hyo experiment vaccines gave a detectable IFN-γ response post-vaccination. The 10% SP-oil (T02) drove the strongest IFN-γ response post-vaccination. The 20% SLCD (T05) induced an earlier response, but the lowest response at day 20. There was a large post-challenge response, especially seen in the placebo group. Additionally, the post-challenge response was lower in the vaccinated pig treatment groups as compared to the placebo group.

Table 7 below shows the lymphoid depletion obtained with the experimental treatments contrasted to the placebo.

TABLE 7

PCV2 Histopathology (Lymphoid Depletion)

| Treatment | Lymphoid Depletion Positive | Negative | % Ever Pos. | Contrasted to Placebo P-value | Significant |
|---|---|---|---|---|---|
| Placebo | 9 | 7 | 56% | NA | NA |
| 10% SP-oil | 1 | 15 | 6% | 0.0059 | Yes |
| 5% Amphigen | 1 | 15 | 6% | 0.0059 | Yes |
| 5% Amph + 5% SLCD | 0 | 16 | 0% | 0.0008 | Yes |
| 20% SLCD | 1 | 15 | 6% | 0.0059 | Yes |

The results presented in Table 7 above show that all vaccines afforded strong protection against lymphoid depletion. Also, no statistically significant vaccine treatment contrasts were observed. Table 8 below shows the immunohistochemistry obtained with the experimental treatments contrasted to the placebo.

TABLE 8

PCV2 Histopathology (Immunohistochemistry)

| Treatment | Immunohistochemistry Positive | Negative | % Ever Pos. | Contrasted to Placebo P-value | Significant |
|---|---|---|---|---|---|
| Placebo | 12 | 4 | 75% | NA | NA |
| 10% SP-oil | 0 | 16 | 0% | 0.0001 | Yes |
| 5% | 1 | 15 | 6% | 0.0002 | Yes |

TABLE 8-continued

PCV2 Histopathology (Immunohistochemistry)

| Treatment | Immunohistochemistry | | | Contrasted to Placebo | |
|---|---|---|---|---|---|
| | Positive | Negative | % Ever Pos. | P-value | Significant |
| Amphigen 5% | 0 | 16 | 0% | 0.0001 | Yes |
| Amph + 5% SLCD | | | | | |
| 20% SLCD | 0 | 16 | 6% | 0.0001 | Yes |

The results presented in Table 8 above show that all vaccines afforded strong protection against PCV2 colonization as evidenced by immunohistochemistry. Also, no statistically significant vaccine treatment contrasts were observed.

In conclusion, the results presented in this example demonstrate that the M.hyo soluble antigen preparation does not interfere with PCV2 efficacy. The results also show that all the PCV/M.hyo experimental vaccine formulations provide efficacy against PCV2 challenge. Additionally, the results indicate that there are some statistical and numerical differences obtained with the different adjuvant formulations, with 10% SP-oil yielding the strongest efficacy.

Example 8

Evaluation of M.Hyo Efficacy of a 1-Bottle PCV2/M.Hyo Combination Vaccine in with Different Adjuvant Formulations This study was designed to evaluate the M.hyo efficacy of a 1-bottle PCV2/M.hyo combination vaccine with different adjuvant formulations. The M.hyo antigen was combined with Porcine Circovirus (Type 1-Type 2 Chimera, or PCV1-2, killed virus) in one bottle.

Processing of Fluids:

Inactivated M.hyo fermentation fluid (described above in Example 1) was treated for each indicated group as follows. T02-T04: These treatments were the same as those described for treatment groups T02-T04 in Example 7 above.

T05: This was formulated with inactivated M.hyo cells (M.hyo bacterin) as described in Example 1 above under the heading "Fermentation and Inactivation".

All experimental PCV2/M.hyo vaccines were formulated with different adjuvant formulations. The experimental vaccine formulations were prepared with M.hyo antigens processed according to treatments T02-T04. In addition, Treatment T01 corresponded to a placebo (sterile saline). Treatment T05 is a positive control corresponding to an expired RespiSure® vaccine, which is an M.hyo bacterin-based vaccine (Pfizer Animal Health).

These experimental formulations are described in Table 9 below, wherein the symbol * indicates the M hyo antigen from global M hyo seed, Protein A treated supernatant and the symbol ** indicates Investigational Veterinary Product (IVP) serial.

TABLE 9

PCV2/M. hyo Experimental Vaccine Formulations Used for M. hyo Efficacy Study in Different Adjuvant Formulations

| Treatment | IVP Serial ** | PCV1-2 Ag | M Hyo* Ag | Adjuvant | Other |
|---|---|---|---|---|---|
| T01 | 87-244-DK (Placebo) | | NA | | Sterile Saline |

TABLE 9-continued

PCV2/M. hyo Experimental Vaccine Formulations Used for M. hyo Efficacy Study in Different Adjuvant Formulations

| Treatment | IVP Serial ** | PCV1-2 Ag | M Hyo* Ag | Adjuvant | Other |
|---|---|---|---|---|---|
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | A827870 | | | Expired "RespiSure" vaccine | |

Pigs at 3 weeks of age were intramuscularly inoculated with a single dose of the different vaccine formulations described in Table 9 above. Fourteen animals were included in both the placebo and 10% SP-oil groups, thirteen animals were included in the positive control group, and sixteen animals were included in both the 5% Amphigen and 5% Amphigen+5% SLCD groups.

Animals were challenged 21 days after vaccination with a virulent M.hyo field isolate. Animals were necropsied 28 days after challenge and the lungs were removed and scored for consolidation consistent with M.hyo infection. Table 10 below contains the lung lesion scores for the respective treatment groups. Statistical significance was determined by a Mixed Model Analysis of lung scores for each group.

TABLE 10

M. hyo Lung Lesions

| Treatment | # Animal | LS Mean Lung Lesion | Range % Lung Lesion |
|---|---|---|---|
| Placebo (T01) | 14 | 13.1% | 0.1-50.5 |
| 10% SP-oil (T02) | 14 | 4.3% | 0.0-50.8 |
| 5% Amphigen (T03) | 16 | 4.7% | 0.0-38.5 |
| 5% Amph + 5% SLCD (T04) | 16 | 12.0% | 0.1-55.8 |
| Expired RSO (T05) | 13 | 2.28% | 0.0-34.5 |

As indicated in Table 10 above, the placebo group had a mean lung lesion score of 13.1%, as compared to the 10% SP-oil and 5% Amphigen treatment groups which had mean lung scores of 4.3% and 4.7%, respectively. Both the 10% SP-oil and 5% Amphigen formulations reduced and/or prevented lung lesions. Thus, the experimental PCV/M.hyo vaccines formulated with 10% SP-oil or 5% Amphigen were considered efficacious. The PCV2 antigen did not appear to interfere with the M.hyo efficacy of these formulations.

In contrast, the 5% Amphigen+5% SLCD group had a mean lung lesion score of 12.0%. which was an unacceptable result in that it was not different as compared to the placebo. Consequently, the experiment PCV/M.hyo vaccine formulated with 5% Amphigen+5% SLCD was not considered as efficacious.

It is noted that due to the reduced animal number and high variability in lung lesion scoring, no statistical treatment effect could be conclusively demonstrated in this study. For this reason, it was decided that another study would be designed to test the M.hyo efficacy of the PCV/M.hyo experimental formulations in 10% SP-oil. This repeat study is presented in Example 9 below.

Example 9

Evaluation of M.Hyo Efficacy of a 1-Bottle PCV2/M.Hyo Combination Vaccine in 10% SP-Oil This study is a proof of concept designed to evaluate the M.hyo fraction efficacy of four experimental PCV2/M.hyo vaccines (Serials L0711RK11, L0711RK12, L0711RK13 and L0711RK14 in Table 11 below) prepared by different M.hyo manufacturing processes which utilize Protein A for IgG removal compared to control vaccines prepared with the standard M.hyo manufacturing process. Each of these four experimental PCV2/M.hyo vaccines included 10% SP-oil as the adjuvant.

Processing of Fluids:

T02: Inactivated *M. hyopneumoniae* antigen as described under "Fermentation and Inactivation" in Example 1 above.

T03 and T04: Formulated with inactivated *M. hyopneumoniae* cells as described under "Fermentation and Inactivation" in Example 1 above.

T05: Protein A treatment of medium used to grow *M. hyopneumoniae*. PPLO (porcine heart derived) was made per manufacturer's directions (i.e., 21 g/L) and yeast extract solution was made at 21 g/L in USP. Yeast extract solution was added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. Antibodies in the complete PPLO media were removed by treatment with protein A. Briefly, one liter of rProtein A Sepharose (part number 17-5199-03 GE Healthcare) was packed into a glass column (10×11.5 cm). After removal of storage buffer, the column was treated with 2 column volumes of 1M acetic acid. The resin was equilibrated with 5 column volumes of 50 mM NaPO4, 1M NaCl buffer (pH 7.0). Fifteen liters of complete PPLO medium was loaded onto the resin at a linear flow rate of 140 cm/hour. The column flow through was collected and filter sterilized through a 0.2 micron filter (Sartorius). The treated medium was used propagate *M. hyopneumoniae* cells as described under "Fermentation and Inactivation" above. Whole inactivated culture (including cells) was formulated into the final vaccine.

T06: Inactivated *M. hyopneumoniae* cells were prepared as described under "Fermentation and Inactivation" in Example 1 above. The inactivated fermentation fluid was centrifuged at ~20,000×g (Sorvall RCSB) for 30 min. and the supernatant was sterilized via 0.2 uM filtration. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 µM filter.

T07: Inactivated *M. hyopneumoniae* cells were prepared as described under "Fermentation and Inactivation" in Example 1 above. The inactivated fermentation fluid was clarified by via tangential flow filtration. Briefly, a polyether sulfone filter (GE HealthCare, part number 56-4102-71) with nominal pore size of 0.2 µM was sanitized with 0.5N sodium hydroxide solution followed by extensive rinsing with sterile USP water. Inactivated *mycoplasma* culture fluid was introduced to the apparatus at a recirculation rate targeted to 14.6 L/minute and a transmembrane pressure of 2-3.4 PSI. Clarification was performed at room temperature. Filter permeate was collected and stored at 2-8 C until further processing. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 2.3 liters of the clarified/filtered *M. hyopneumoniae* antigen containing fluids were passed through the resin at a flow rate of 120 cm/hr. The flow through was collected and sterilized via 0.2 µM filter.

T08: Inactivated *M. hyopneumoniae* cells were prepared as described under "Fermentation and Inactivation" above. The inactivated fermentation fluid was centrifuged at ~20,000×g (Sorvall RCSB) for 30 min. and the supernatant was sterilized via 0.2 uM filtration. One hundred fifteen mls of rProtein A Sepharose (part number 17-5199-03 GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 uM filter.

The experimental vaccine formulations were prepared with M.hyo antigens processed according to treatments T02-T08 above. T02, T03 and T04 corresponded to positive controls. In addition, Treatment T01 corresponded to a placebo (sterile saline).

These experimental formulations are described in Table 11 below. The M.hyo antigen corresponds to the M.hyo antigen from global M.hyo seed, Protein A treated supernatant. The information in the "Protein A Treatment" column indicates whether the M.hyo supernatant was treated with Protein A either before or after fermentation.

TABLE 11

PCV2/*M. hyo* Experimental Vaccine Formulations Used for *M. hyo* Efficacy Study in SP-Oil Adjuvant

| Treatment | Serial No. | PCV1-2 Ag | *M. hyo* Ag | Protein A Treatment | Supernatant Clarification Method | Protein A Brand | Adjuvant | Other |
|---|---|---|---|---|---|---|---|---|
| T01 | L0311AS11 | | | | NA | | | Sterile Saline |
| T02 | A828718 | NA | 13 | | Expired RespiSure One | | Amphigen | |
| T03 | L0711RK09 | 1.5 RP | 7.5 RP | | *M. hyo* without Protein A treatment and with PCV-2 | | 10% SP Oil | NA |
| T04 | L0711RK10 | NA | | | *M. hyo* without Protein A treatment and without PCV-2 | | | |
| T05 | L0711RK11 | 1.5 RP | | Before | NA | Sepharose | | |

TABLE 11-continued

| PCV2/*M. hyo* Experimental Vaccine Formulations Used for *M. hyo* Efficacy Study in SP-Oil Adjuvant | | | | | | | | |
|---|---|---|---|---|---|---|---|---|
| Treatment | Serial No. | PCV1-2 Ag | *M. hyo* Ag | Protein A Treatment | Supernatant Clarification Method | Protein A Brand | Adjuvant | Other |
| T06 | L0711RK12 | | | After | Centrifuge | MAbSelect | | |
| T07 | L0711RK13 | | | After | Filter | MAbSelect | | |
| T08 | L0711RK14 | | | After | Centrifuge | Sepharose | | |

Figures 8A, 8B:
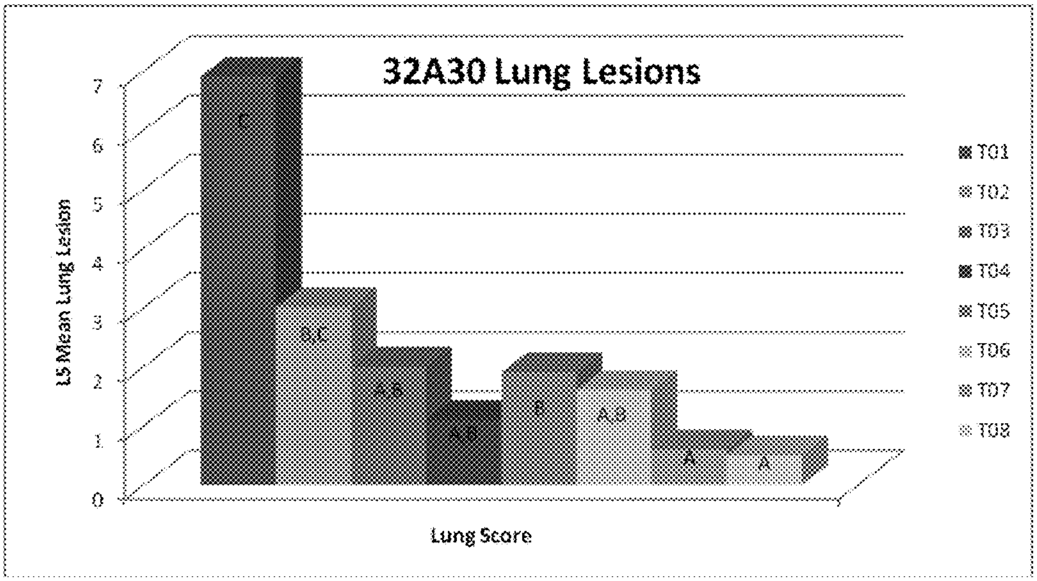
FIGS. 8A and 8B depict the M.hyo efficacy of the PCV2/M.hyo experimental vaccine formulations in SP-oil. The lung scores for formulations employing M.hyo treatments T02-T08 vs. a placebo (T01) are depicted graphically in FIG. 8A. The table in FIG. 8B depicts the contrast of treatments T02-T08 with the placebo.

Pigs at 3 weeks of age were intramuscularly inoculated with a single dose of the different vaccine formulations described in Table 11 above. There were 18 pigs included in each treatment group. Animals were challenged 21 days after vaccination with a virulent M.hyo field isolate. Animals were necropsied 28 days after challenge and the lungs were removed and scored for consolidation consistent with M.hyo infection. FIGS. 8A and 8B show the lung lesion scores for the respective treatment groups. Statistical significance was determined by a Mixed Model Analysis of lung scores for each group.

The lung lesion results depicted in FIGS. 8A and 8B indicate that of all the treatments, only two (T07 and T08) had 100% of pigs in the <5% lung lesion category. It is noted that strong statistical difference were observed in this study.

The results in the present example demonstrate significant M.hyo efficacy in a 1-bottle PCV2/M.hyo experimental formulation employing the Protein A-treated M.hyo supernatant and utilizing SP-oil as the adjuvant. Additionally, Example 7 above demonstrated PCV2 efficacy in a 1-bottle PCV2/M.hyo formulation employing the Protein A-treated M.hyo supernatant and utilizing SP-oil as the adjuvant. Taken together, both M.hyo and PCV2 efficacy have been demonstrated in the 1-bottle PCV2/M.hyo combinations employing Protein A-treated M.hyo supernatant.

Example 10

In Vivo Safety of Experimental PCV2/M.Hyo Experimental Vaccines

This study was conducted to evaluate in vivo safety of experimental PCV2-M.hyo vaccines formulated at maximum antigen dose in various adjuvant formulations in the host animal when given at the youngest age (3 weeks of age). Different adjuvant platforms were evaluated in order to determine which of these platforms provided an acceptable safety profile based on temperature, injection site reactions and clinical observations. A 20% SLCD/10% SP-oil formulation was used as a positive ("unsafe") control due to historic issues with injection site reactions observed by this investigative group and others.

Processing of Fluids:

All vaccines were prepared with inactivated *M. hyopneumoniae* antigen as described under "Fermentation and Inactivation" in Example 1. M.hyo whole bulk antigen was used since it was known to contain soluble and insoluble M.hyo antigens, in addition to the immunoglobulins and immunocomplexes that would be removed upon protein A treatment. It is reasonable to conclude that removal of insoluble cell debris and immunuoglobulins and immunocomplexes will only further enhance the safety of the vaccine formulations. The intention of this study was to stringently test the safety of the various adjuvant formulations containing PCV2 antigen and M.hyo antigen. The PCV2 and M.hyo antigens were formulated at maximum release levels to further assess safety. These experimental formulations are described in Table 12 below. IVP indicates Investigational Veterinary Product (IVP).

TABLE 12

| PCV2/*M. hyo* Experimental Vaccine Formulations Used for Safety Study | | | | | |
|---|---|---|---|---|---|
| IVP Serial | PCV1-2 Ag | M Hyo* Ag | Adjuvant | Other | Minimum Vaccine Vol. (mL) |
| 87-244-DK (Placebo) | | | NA | Sterile Saline | NA |
| L0411RK15 | 7.8 RP | 13 RP | 10% SP Oil | NA | 200 |
| L0411RK16 | | | 5% Amphigen | | 200 |
| L0611RK05 | | | 5% Amphigen + 5% SLCD | | 200 |
| L0611RK06 | | | 20% SLCD + 10% SP Oil | | 200 |

**M hyo* antigen = from global *M hyo* seed (whole bulk antigen).

The safety parameters employed in this study were rectal temperature profile and injection site reaction. The results of this study indicated that all candidate adjuvant platforms provided an acceptable safety profile in terms of rectal temperature profile and clinical observations (results not shown). Only the 20% SLCD+10% SP-oil (i.e., positive control) was significantly different than the placebo vaccine and had a number of severe injection site reactions (results not shown).

Example 11

Preparation of Protein a Treated M.Hyo Antigen for Pivotal Studies

Figure 9:
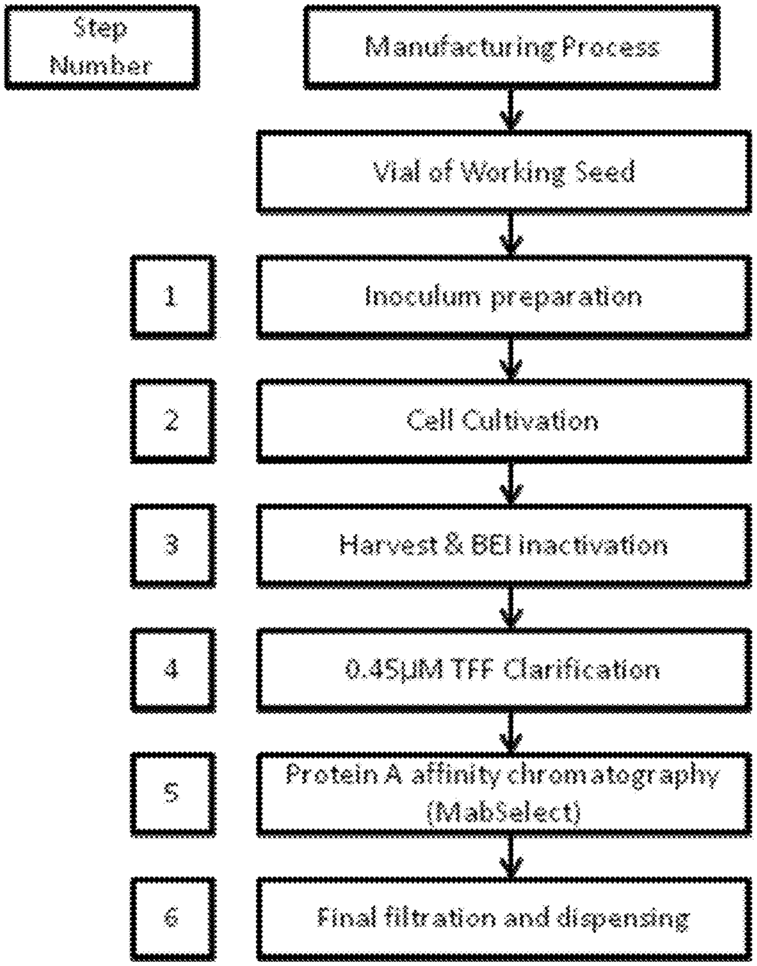
FIG. 9 is a flowchart which shows one embodiment of a manufacturing process used to prepare PCV2-compatible Protein-A treated M.hyo antigen.

FIG. 9 is a flowchart which shows one embodiment of a manufacturing process used to prepare PCV2 compatible Protein-A treated M.hyo antigen. Inactivated whole cultures of M.hyo were clarified of cells via tangential flow filtration. Briefly, a polyether sulfone filter (GE Healthcare, part number 56-4102-49) with nominal pore size of 0.45 μM was sanitized with 0.5N sodium hydroxide solution followed by extensive rinsing with sterile USP water. Inactivated *mycoplasma* culture fluid was introduced to the apparatus at a recirculation rate targeted to 11.0 L/minute and a transmembrane pressure of ~5 PSI. Clarification was performed at room temperature. Filter permeate was collected and stored at 2-8° C. until further processing.

Following clarification, antigen containing fluids were treated with protein A resin to reduce antibody levels. Briefly, MAbSelect protein A resin (GE Healthcare) was packed into a glass column to a height of 12 cm. The resin was equilibrated with 5 column volumes of 50 mM sodium phosphate, 250 mM NaCl buffer (pH 7.0). Antigen containing fluid, equivalent to 10 column volumes, was loaded onto the resin at a linear flow rate of 100 cm/hour. The column flow through was collected and filter sterilized through a 0.2 micron filter. Regeneration of the column was achieved by flowing 3 column volumes of 25 mM acetate solution at pH 3.7 followed by 4 column volumes of 1M acetic acid solution. Anti-PCV2 antibodies and *M. hyopneumoniae* antigen levels were measured in the final antigen fluid via PCV2 specific antibody ELISA and p46 antigen quantification ELISA, respectively.

Example 12

Evaluation of Virucidal Activity Against PRRS Virus

The studies presented in this example were designed to evaluate the various adjuvant platforms for virucidal activity against PRRS virus. Initial experiments focused on adjuvant alone (i.e., the formulations did not contain PCV or M.hyo antigens). The adjuvant evaluation for PRRS virucidal activity is presented in FIG. 10. Preliminary virucidal assessment indicated that 10% SP-oil, 0.2% Carbopol and 2.5% Amphigen are non-virucidal to PRRS virus. In contrast, the 20% SLCD adjuvant appeared to be virucidal to PRRS virus.

Further studies were performed to evaluate whether the PCV/M.hyo formulations adjuvanted with the different adjuvant platforms were non-virucidal to PRRS virus. These results are presented in Table 13 below, wherein the symbol * indicates those vaccine serials which were virucidal to PRRS virus.

TABLE 13

Results of PRRS Virucidal Assay with Different Formulations

| Vaccine Serial Used in Studies of Examples 7, 8, 10 | | | Potency | | PRRS Virucidal | |
|---|---|---|---|---|---|---|
| | | | p46 RP | PCV2 NVSL | | |
| Study | Description | Serial # | (ru/ds) | RP | A | B |
| Examples 7, 8, 10 | Sterile Saline (0.9% Sodium chloride) | 87-244-DK (Placebo) | | | | |
| Examples 7, 8 | cPCV (RP 1.6) + *M Hyo* Prot A treated (RP 7.5) in 10% SP Oil | L0411RK08 | 7.1 | 1.29 | −0.10 | −0.13 |
| Examples 7, 8 | cPCV (RP 1.6) + *M Hyo* Prot A treated (RP 7.5) in 5% Amphigen | L0411RK09 | 7.3 | 1.33 | −0.10 | +0.14 |
| Examples 7, 8 | cPCV (RP 1.6) + *M Hyo* Prot A treated (RP 7.5) in 5% Amph + 5% SLCD | L0611RK03 | 6.9 | 1.15 | −0.36 | −0.33 |
| Example 7 | cPCV (RP 1.6) monovalent in 20% SLCD | L0611RK04 | | 1.50 | −1.86* | −0.50 |
| Example 8 | Expired RespiSure One serial | A827870 | 12.6 | | | |
| Example 10 | cPCV (RP 7.8) + *M Hyo* Whole Bulk (RP 13.3) in 10% SP Oil | L0411RK15 | 14 | 1.03 | −0.32 | −0.03 |
| Example 10 | cPCV (RP 7.8) + *M Hyo* Whole Bulk (RP 13.3) in 5% Amphigen | L0411RK16 | 15.5 | 1.12 | −0.36 | −0.53 |
| Example 10 | cPCV (RP 7.8) + *M Hyo* Whole Bulk (RP 13.3) in 5% Amph + 5% SLCD | L0611RK05 | 17.5 | 1.50 | −0.54 | −0.33 |
| Example 10 | cPCV (RP 7.8) + *M Hyo* Whole Bulk (RP 13.3) in 20% SLCD + 10% SP Oil | L0611RK06 | 15.9 | 1.13 | −1.93* | −0.99* |

*Indicates Virucidal (>0.7 log loss)

A—Virucidal assay control GMT ~5.53 log/mL

B—Virucidal assay control GMT ~6.42 log/mL

The results presented in Table 13 above indicate that 10% SP-oil is non-virucidal to PRRS virus. Further PCV/M.hyo vaccine serials were prepared using 10% SP-oil as the adjuvant (Table 14). The results shown in Table 14 below further demonstrate that 10% SP-oil is non-virucidal to PRRS virus. The test sample values in Table 14 were each higher (+ sign) than the virucidal assay control, which had a geometric mean titer (GMT) of about 5.9±0.5 log/ml.

TABLE 14

Results of Virucidal Assay with Different PCV/*M. hyo* Formulations Adjuvanted with 10% SP-oil

| Vaccine Serial Used Description | Serial # | Potency: p46 RP (ru/ds) Reference L1211RK15 | Potency: PCV2 NVSL Reference L1211RK15 | PRRS Virucidal log10 TCID50/mL |
|---|---|---|---|---|
| Sterile Diluent (sterile water) | 1949122 | na | na | |
| cPCV + M Hyo Prot A treated in 10% SP Oil | L0912RK12 | 1.62 | 2.60 | +0.58 |
| cPCV + M Hyo Prot A treated in 10% SP Oil | L0912RK10 | 0.88 | 1.23 | +0.58 |
| cPCV + M Hyo Prot A treated in 10% SP Oil | L0912RK11 | 1.24 | 2.62 | +0.58 |
| cPCV + M Hyo Prot A treated in 10% SP Oil | L0912RK08 | 1.08 | 1.03 | +0.91 |
| cPCV + M Hyo Prot A treated in 10% SP Oil | L0912RK09 | 1.65 | 2.06 | +0.50 |

Virucidal Assay control GMT ~5.9 ± 0.5 log/ml

The results presented in this example demonstrate that 10% SP-oil is non-virucidal to PRRS virus. The results presented in this example further demonstrate that the PCV/M.hyo formulation adjuvanted with 10% SP-oil was among those vaccine serials which were considered non-virucidal to PRRS virus (Table 13 and Table 14). In conclusion, the PCV/M.hyo formulation adjuvanted with 10% SP-oil was considered an effective platform on which to base a trivalent combination including PCV, M.hyo, and PRRS virus.

Example 13

Preparation of a PCV/M.Hyo/PRRS Combination Vaccine

A PCV/M.hyo formulation adjuvanted with an adjuvant platform which is non-virucidal to PRRS virus (see Table 13 and Table 14 above), is provided as a ready-to-use in one-bottle liquid composition. This 1-bottle PCV/M.hyo formulation employs Protein A-treated M.hyo supernatant. Both M.hyo and PCV2 efficacy have been demonstrated in such PCV2/M.hyo formulations employing M.hyo Protein A-treated supernatant (see Examples 7-9). In the present example, this divalent PCV2/M.hyo formulation is combined with a monovalent PRRS virus antigen.

In one embodiment, a PCV/M.hyo combination in 10% SP-oil and corresponding to one of the vaccine serials L0711RK11, L0711RK12, L0711RK13 and L0711RK14 in Table 11 above is provided as a ready-to-use in one bottle liquid composition. The results presented in Example 12 above demonstrated that 10% SP-oil is non-virucidal to PRRS virus. Example 12 also demonstrated that PCV2/M.hyo formulations adjuvanted with 10% SP-oil were among those vaccine serials which were considered non-virucidal to PRRS virus. In the present example, such a 1-bottle PCV2/M.hyo liquid composition is used to re-hydrate a lyophilized genetically modified live PRRS virus composition contained in a second bottle, such that all antigens are contained in a single bottle prior to being administered to a pig of a suitable age (e.g., at 3 weeks of age or older).

In one embodiment, the PRRS virus has the genomic sequence corresponding to SEQ ID NO: 16 or a variant thereof. In another embodiment, the PRRS virus employed in the trivalent composition is the PRRS virus isolate designated ISU-55, which was deposited in the ATCC under the accession number VR 2430. Suitable amounts of the respective antigens are described herein. Desirably, all antigens are administered in a single dose to the pig.

Example 14

Evaluation of PCV2 Efficacy of a PCV2/M.Hyo/PRRS Combination Vaccine Followed by a PCV2 Challenge This study was designed to evaluate the efficacy of the PCV1-2 chimera, killed virus fraction of an experimental PCV2/M.hyo/PPRS combination vaccine, administered intramuscularly once to pigs at 3 weeks of age and challenged with a virulent PCV2 isolate three weeks post vaccination. These trivalent vaccines included Porcine Circovirus Type 1-Type 2 Chimera, killed virus, Respiratory and Reproductive Syndrome Vaccine, Respiratory Form, Modified Live Virus, and *Mycoplasma Hyopneumoniae* Bacterial Extract.

This trivalent combination was prepared by re-hydrating a lyophilized genetically modified live PRRS virus (PRRS-MLV) with a one-bottle liquid formulation including a combination of porcine circovirus Type1-Type 2 Chimera, killed virus and M.hyo bacterial extract (PCV2/M.hyo), which is adjuvanted using 10% SP-oil (see Example 13 above). The experimental formulations administered throughout the course of the present study are described in Table 15 below.

TABLE 15

PCV2/*M. hyo*/PRRS Experimental Vaccine Formulations Used for PCV2 Efficacy Study

| Group | N | CP or IVP | Serial No. | Antigen Input[1] | Study Days Vaccination | Challenge | Necropsy |
|---|---|---|---|---|---|---|---|
| T01 | 24 | *M hyo* | L1012RK10 | ≥153 RU/mL | Day 0 | Day 21 | Day 42 |
| | | PRRSV MLV | L1011CM14 | 4.5 log10 TCID50 | 2 mL IM | 1 mL IM 2 mL IN | ± 3 days |
| T02 | 24 | PCV2 | L0912RK08 | 0.688% | Left Neck | 40895 | |
| | | *M hyo* | | 102 RU/mL | | | |
| | | PRRSV MLV | L1011CM14 | 4.5 log10 TCID50 | | | |
| T03 | 24 | PCV2 | L0912RK09 | 1.375% | | | |
| | | *M hyo* | | 153 RU/mL | | | |
| | | PRRSV MLV | L1011CM14 | 4.5 log10 TCID50 | | | |

IVP = Investigational Veterinary Product
CP = Control Product
IM = Intramuscularly
IN = Intranasal
[1]% = PCV2 antigen, RU/mL = *M hyo* antigen, log10 TCID50 = PRRSV antigen Pigs at 3 weeks of age were intramuscularly inoculated with a single dose of the different vaccine formulations described in Table 15 above. Twenty-four animals were included in each of the treatment groups. Animals were challenged 21 days after vaccination with a virulent PCV2a isolate.

Figure 11:
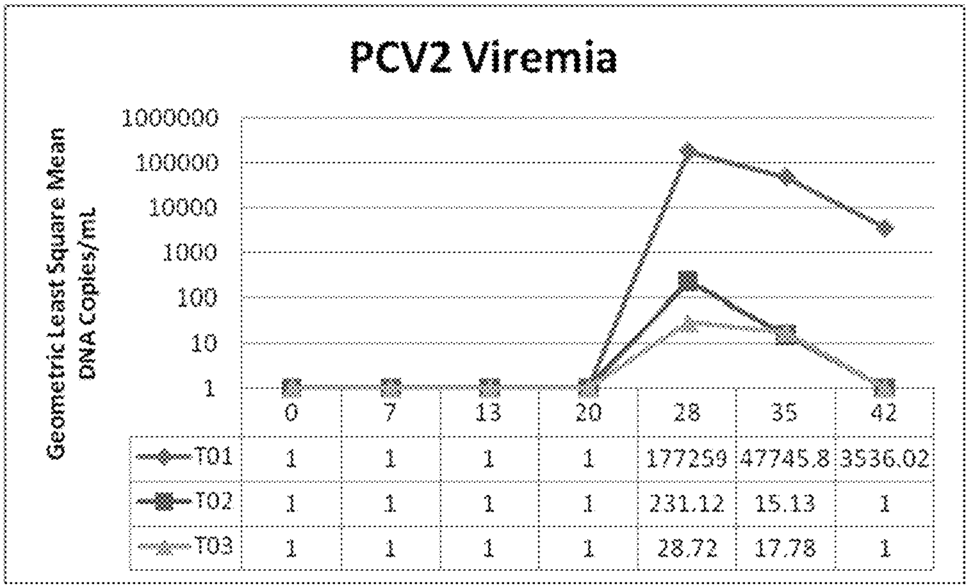
FIG. 11 is a graph showing the PCV2 viremia results (PCV2 Quantitative PCR) observed with PCV2/M.hyo/PRRS experimental vaccine formulations.

The PCV2 viremia results (PCV2 Quantitative PCR) observed in this study are presented in FIG. 11. It is noted that PCV2 viremia was used as the primary efficacy variable. The PCV2 viremia results are presented as DNA copies/ml. As shown in FIG. 11, all treatments had significantly less viremia (P<0.001) compared to the placebo on days 28, 35 and 42 (challenge was day 21).

PCV2 Serology, PCV2 fecal shed, lymphoid depletion, and Immunohistochemistry (IHC) were also monitored as secondary efficacy variables in this study. These results are described below.

Figure 12:
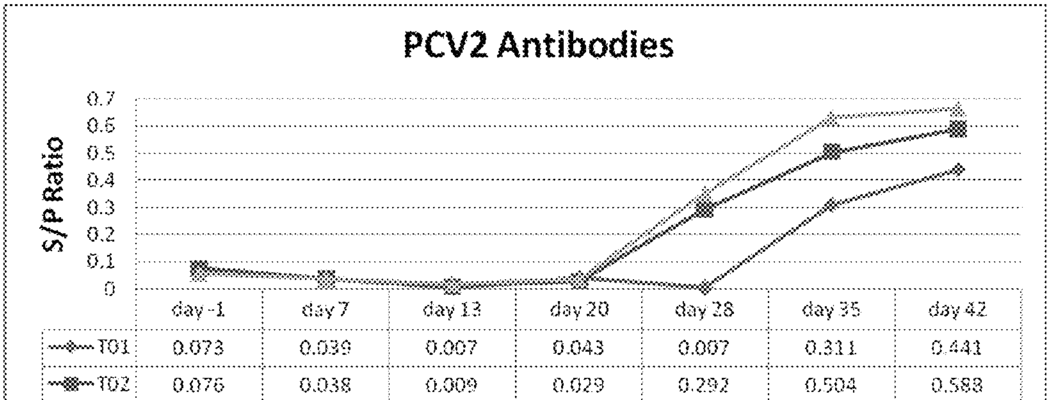
FIG. 12 is a graph showing the PCV2 ELISA results observed with PCV2/M.hyo/PRRS experimental vaccine formulations on days −1, 7, 13, 20, 28, 35 and 42 of the study (challenge was day 21).

The PCV2 serology results are presented in FIG. 12, which shows the PCV2 ELISA results on days −1, 7, 13, 20, 28, 35 and 42 of the study (challenge was day 21). The status of each sample was expressed as a sample to positive ratio (S/P). These results show that compared to the placebo group, both treatment groups had significantly higher PCV2 antibody titers post-challenge (P<0.0345)

Figure 13:
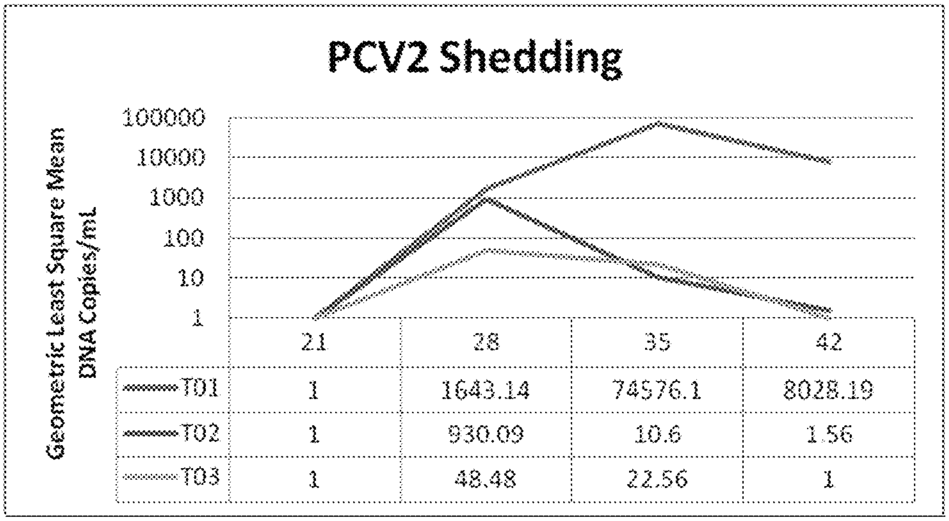
FIG. 13 is a graph showing the PCV2 fecal shed obtained with the T02 and T03 treatments (PCV2/M.hyo/PRRS experimental vaccine formulations) described in Example 14 vs. the placebo (T01).

The PCV2 fecal shed obtained with the T02 and T03 treatments vs. the placebo (T01) is presented in FIG. 13. These results are expressed as PCV2 DNA copies/ml. The results in FIG. 13 indicate that both the T02 and T03 treatments had significantly less fecal shed (P<0.0001) when compared to the placebo on days 35 and 42.

Table 16 below shows the significant protection against lymphoid depletion obtained with the experimental treatment (T02) contrasted to the placebo.

TABLE 16

PCV2 Histopathology (Lymphoid Depletion)

| | Lymphoid Depletion | | | Contrasted to Placebo | |
|---|---|---|---|---|---|
| Treatment | Positive | Negative | % Ever Pos. | P-value | Significant |
| Placebo | 13 | 8 | 61.9% | NA | NA |
| T02 | 3 | 17 | 15% | 0.047 | Yes |
| T03 | 7 | 13 | 35% | 0.0780 | No |

The results presented in Table 17 below shows the significant protection against Histiocytic Replacement obtained with the experimental treatment (T02) contrasted to the placebo.

TABLE 17

PCV2 Histopathology (Histiocytic replacement)

| | Histiocytic Replacement | | | Contrasted to Placebo | |
|---|---|---|---|---|---|
| Treatment | Positive | Negative | % Ever Pos. | P-value | Significant |
| Placebo | 11 | 10 | 52.4% | NA | NA |
| T02 | 2 | 18 | 10% | 0.0105 | Yes |
| T03 | 6 | 14 | 30% | 0.1566 | No |

Table 18 below shows the immunohistochemistry obtained with the experimental treatments contrasted to the placebo. Both vaccines (T02 and T03) showed significant protection (P<0.0059) against colonization of PCV2 antigen in lymphoid tissues.

TABLE 18

PCV2 Histopathology (Immunohistochemistry)

| | Immunohistochemistry | | | Contrasted to Placebo | |
|---|---|---|---|---|---|
| Treatment | Positive | Negative | % Ever Pos. | P-value | Significant |
| Placebo | 14 | 7 | 66.7% | NA | NA |
| T02 | 3 | 17 | 15% | 0.0030 | Yes |
| T03 | 4 | 16 | 20% | 0.0059 | Yes |

In conclusion, the results presented in this example demonstrate that the experimental vaccines used in this study provided efficacy against a PCV2 challenge. Both potency levels of the vaccines provided significant protection against the primary variable as well as PCV2 colonization. However, the T02 group also provided significant protection against PCV2 lesions (lymphoid depletion and histiocytic replacement).

Example 15

Evaluation of M.Hyo Efficacy of a PCV2/M.Hyo/PRRS Combination Vaccine Followed by M.Hyo Challenge This study was designed to evaluate the efficacy of the M.hyo fraction of an experimental PCV2/M.hyo/PPRS combination vaccine, administered intramuscularly in susceptible pigs at 3 weeks of age and challenged with a virulent *Mycoplasma hyopneumoniae* isolate three weeks post vaccination. These trivalent vaccines included Porcine Circovirus Type 1-Type 2 Chimera, killed virus, Respiratory and Reproductive Syndrome Vaccine, Respiratory Form, Modified Live Virus, and *Mycoplasma Hyopneumoniae* Bacterial Extract.

Processing of Fluids:

Inactivated, clarified M.hyo fermentation fluid (described above in Example 11) was used for each treatment group as follows.

T01: A negative control treatment consisting of PCV1-2 vaccine without *M. hyopneumoniae* antigen which was used as diluent in a lyophilized PRRSV modified live vaccine.

T02: Inactivated *M. hyopneumoniae* antigen was combined with Porcine Circovirus (Type 1-Type 2 Chimera, or PCV1-2, killed virus) in one bottle. The PCV1-2/M. hyo combination was used as diluent in a lyophilized PRRSV modified live vaccine.

T03: Inactivated *M. hyopneumoniae* antigen as described above in Example 11 with an additional step to concentrate the antigen 20× by molecular filtration was combined with Porcine Circovirus (Type 1-Type 2 Chimera, or PCV1-2, killed virus) in one bottle. The PCV1-2/M. hyo combination was used as diluent in a lyophilized PRRSV modified live vaccine.

These experimental formulations are described in Table 19 below. In Table 19, CP is control product and IVP is Investigational Veterinary Product. The M.hyo antigen corresponds to the M.hyo antigen from global M.hyo seed, Protein A treated supernatant.

TABLE 19

PCV2/*M. hyo*/PRRS Experimental Vaccine Formulations used for *M. hyo* Efficacy Study

| Group | N | CP or IVP | Serial No. | Potency |
|---|---|---|---|---|
| NTX | 5 | Sentinel | | |
| T01 | 25 | PCV2 | L0412RK13 | 4.3 Relative Potency Units |
| | | PRRSV MLV | L1011CM14 | 4.5 +/− 0.5 LOG10 $FAID_{50}$/mL |
| T02 | 25 | PCV2 | L1211RK12 | 4.5 Relative Potency Units |
| | | M hyo | | 2.7 Relative Potency Units |
| | | PRRSV MLV | L1011CM14 | 4.5 +/− 0.5 LOG10 $FAID_{50}$/mL |
| T03 | 25 | PCV2 | L0712RK33 | 3.4 Relative Potency Units |
| | | M hyo-filter concentrated | | 2.7 Relative Potency Units |
| | | PRRSV MLV | L1011CM14 | 4.5 +/− 0.5 LOG10 $FAID_{50}$/mL |

Pigs at 3 weeks of age were intramuscularly inoculated with a single dose of the different vaccine formulations described in Table 19 above. Animals were challenged 20 days after vaccination with a virulent M.hyo field isolate. Twenty five animals completed the study in group T01 and T03, and 24 completed the study in group T02. Animals were necropsied 28 days after challenge and the lungs were removed and scored for consolidation consistent with M.hyo infection. Table 20 below contains the lung lesion scores for the respective treatment groups. Statistical significance was determined by a Mixed Model Analysis of lung scores for each group.

TABLE 20

*M. hyo* Lung Lesions

| Treatment | # Animal | LS Mean Lung Lesion | Range % Lung Lesion |
|---|---|---|---|
| T01: PCV1-2, PRRSV MVL | 25 | 7.65% | 0.00 to 44.75 |
| T02: PCV1-2/*M. hyo*, PRRSV MVL | 24 | 4.38% | 0.10 to 20.95 |
| T03: PCV/*M hyo*-filter concentrated, PRRSV MVL | 25 | 2.23% | 0.00 to 17.95 |

Compared to the negative control group (T01), treatment group T03 demonstrated a significant reduction ($P \leq 0.05$) in percent lung with lesion compared to T01. The percent lung lesions for T02 were not significantly different from either T01 or T03.

The results in the present example demonstrate that an experimental trivalent vaccine formulation (T03 treatment) used in this study provided significant efficacy against M.hyo challenge.

Example 16

Evaluation of PRRSV Efficacy of a PCV/M.Hyo/PRRS Combination Vaccine

This study was designed to evaluate the efficacy of the PRRSV fraction of an experimental PCV2/M.hyo/PPRS combination vaccine.

Study Summary:

On Day 0, approximately 102 clinically healthy, three week old pigs, sero-negative to PRRSV, SIV and *M. hyopneumoniae* and free of PCV viremia by PCR, are selected and allotted (blocked by litter) to one of the four treatment groups (24 per group) or a sentinel (NTX) group (6). Pigs are administered a single 2 mL intramuscular (IM) dose of an experimental Porcine Circovirus Type 1-Type 2 Chimera, Killed Virus Vaccine—*Mycoplasma Hyopneumoniae* Bacterial Extract (T01), or an experimental Porcine Circovirus Type 1-2 Chimera-Respiratory and Reproductive Syndrome Vaccine, Respiratory Form, Modified Live and Killed Virus—*Mycoplasma Hyopneumoniae* Bacterial Extract (T02, T03 and T04). The NTX group animals are housed in a separate pen from treatment groups during the vaccination phase of the study. Four weeks after vaccination the NTX pigs are euthanized and necropsied, prior to re-housing the treatment groups, to confirm absence of PRRSV lung lesions. All treated pigs are challenged with a virulent PRRSV challenge strain (NADC20). All remaining pigs are euthanized and necropsied ten (10) days after challenge. At necropsy, the percentage of consolidation for each lobe of the lung (left cranial, left middle, left caudal, right cranial, right middle, right caudal, and accessory) is scored and recorded as percent of the lobe observed with lesions. The PRRSV negative status of T01 pigs is tested (IDEXX ELISA) prior to challenge. Clinical observations are recorded once daily for the duration of study and body weights are taken prior to challenge and at necropsy.

The experimental formulations are described below and in Table 21. The M.hyo antigen control lot is prepared as described in Example 11 above. The PCV2 antigen is a killed cPCV1-2 antigen prepared as described in Example 2 above. Prior to inactivation of the chimeric virus, the PCV2 antigen lot was concentrated 20× and the concentrates were washed with a balanced salt solution. The PCV/M.hyo one-bottle formulation (adjuvanted in 10% SP oil) is used to re-hydrate lyophilized modified live PRRSV.

T01: Experimental preparation of high passage Porcine Circovirus Type 1-Type 2 Chimera, killed virus (1.65% of 20× concentrated antigen lot) and *Mycoplasma Hyopneumoniae* Bacterial Extract (Dose-9.0 RP; 153 RU/mL). T01 preparation corresponds to serial number L0912RK12 (PCV/M.hyo) and is a negative control (no PRRSV antigen).

T02: Experimental preparation of high passage Porcine Circovirus Vaccine Type 1-Type 2 Chimera, killed virus (1.65% of 20× concentrated antigen lot) and *Mycoplasma Hyopneumoniae* Bacterial Extract (Dose—9.0 RP; 153 RU/mL) and Experimental preparation of high passage of Porcine Reproductive & Respiratory Syndrome Vaccine Respiratory Form, Modified Live Virus (MID (≤2.5 logs). T02 preparation corresponds to serial number L0912RK12 (PCV/M.hyo)+(PPRS MLV at MID≤2.5 logs).

T03: Experimental preparation of high passage Porcine Circovirus Vaccine Type 1-Type 2 Chimera, killed virus (1.65% of 20× concentrated antigen lot) and *Mycoplasma Hyopneumoniae* Bacterial Extract (Dose—9.0 RP; 153 RU/mL) and Experimental preparation of high passage of Porcine Reproductive & Respiratory Syndrome Vaccine Respiratory Form, Modified Live Virus (MID (≤3.0 logs). T03 preparation corresponds to serial number L0912RK12 (PCV/M.hyo)+(PPRS MLV at MID≤3.0 logs).

T04: Experimental preparation of high passage Porcine Circovirus Vaccine Type 1-Type 2 Chimera, killed virus (1.65% of 20× concentrated antigen lot) and *Mycoplasma Hyopneumoniae* Bacterial Extract (Dose—9.0 RP; 153 RU/mL) and Experimental preparation of high passage of Porcine Reproductive & Respiratory Syndrome Vaccine Respiratory Form, Modified Live Virus (MID (≤3.5 logs). T04 preparation corresponds to serial number L0912RK12 (PCV/M.hyo)+(PPRS MLV at MID≤3.5 logs).

These experimental formulations are described in Table 21 below. The M.hyo antigen corresponds to the M.hyo antigen from global M.hyo seed, Protein A treated supernatant. Serial numbers for the PRRSV preparations are to be determined (TBD).

TABLE 21

Study Design

| | | | | Study Days | | |
|---|---|---|---|---|---|---|
| Group | N | CP or IVP[1] | Lot No. | Vaccination | Challenge | Necropsy |
| NTX | 6 | Sentinel | | NA | | At re-housing Lung Scores |
| T01 | 24 | PCV2/*M. hyo* | L0912RK12 | Day 0 2 mL IM Right Neck | Day 28 4 mL (1 mL per nostril + 2 mL IM injection) Left Neck | Day 38 Lung Scores |
| T02 | 24 | PCV2/*M. hyo* + PRRSV | L0912RK12 + TBD | | | |
| T03 | 24 | PCV2/*M. hyo* + PRRSV | L0912RK12 + TBD | | | |
| T04 | 24 | PCV2/*M. hyo* + PRRSV | L0912RK12 + TBD | | | |

[1]Investigational Veterinary Product (IVP) = Porcine *Circovirus* Type 1-2 Chimera (PCV2), Killed Virus vaccine-*Mycoplasma Hyopneumoniae* (*M hyo*) Bacterial Extract adjuvanted with 10% SP Oil (diluent)-Porcine Reproductive & Respiratory Syndrome Vaccine, Respiratory Form, Modified Live Virus (PRRSV) Control Product (CP) = Porcine *Circovirus* Type 1-2 Chimera (PCV2), Killed Virus vaccine-*Mycoplasma Hyopneumoniae* (*M hyo*) Bacterial Extract-without Porcine Reproductive & Respiratory Syndrome Vaccine fraction; Adjuvanted with 10% SP Oil
IM = Intramuscular
NA = Not Applicable

What is claimed is:

1. A method for preparing a multivalent immunogenic composition including a soluble portion of a *Mycoplasma hyopneumoniae* (M.hyo) whole cell preparation, the method comprising:

i) culturing M.hyo in a suitable media over periods ranging from 18-144 hours;

ii) subsequently inactivating the M.hyo culture;

iii) harvesting the inactivated culture fluid, wherein the inactivated culture fluid comprises an M.hyo whole cell preparation comprising both a soluble liquid fraction and insoluble cellular material;

iv) separating the soluble liquid fraction from the insoluble cellular material;

v) substantially removing both IgG and antigen/immunoglobulin immunocomplexes from the separated soluble liquid fraction to form a soluble portion of the M.hyo whole cell preparation; and vi) subsequently combining the soluble portion of the M.hyo whole cell preparation with a PCV2 antigen and PRRS virus antigen.

2. The method of claim 1, wherein vi) comprises combining a ready-to-use liquid composition comprising both the PCV2 antigen and the M.hyo soluble portion with a lyophilized PRRS virus antigen.

3. The method of claim 1, wherein the M.hyo culture is inactivated by exposing the culture to an inactivation agent.

4. The method of claim 3, wherein the inactivation agent is binary ethylenimine (BEI).

5. The method of claim 3, further comprising neutralizing the inactivation agent.

6. The method of claim 1, wherein the soluble liquid fraction is separated from the insoluble cellular material by a centrifugation step.

7. The method of claim 1, wherein the soluble liquid fraction is separated from the insoluble cellular material by a filtration step.

8. The method of claim 1, wherein the soluble liquid fraction is separated from the insoluble cellular material by a precipitation step.

9. The method of claim 1, wherein the separated soluble liquid fraction is treated with a Protein A or Protein G resin to substantially remove both the IgG and antigen/immunoglobulin immunocomplexes contained in the separated soluble liquid fraction.

10. The method of claim 9, wherein the separated soluble liquid fraction is treated with a Protein A resin to substantially remove both the IgG and antigen/immunoglobulin immunocomplexes contained in the separated soluble liquid fraction.

11. The method of claim 1, further comprising admixing the immunogenic composition with an adjuvant.

12. The method of claim 11, wherein the adjuvant is an oil emulsion comprising a polyoxyethylene-polyoxypropylene block copolymer, squalane, polyoxyethylene sorbitan monooleate and a buffered salt solution (SP-oil).

13. The method of claim 1, further comprising admixing the immunogenic composition with a pharmaceutically-acceptable carrier.

14. The method of claim 1, further comprising combining the immunogenic composition with at least one additional porcine antigen.

* * * * *

SEQUENCE LISTING

<160> NUMBER OF SEQ ID NOS: 18

<210> SEQ ID NO 1
<211> LENGTH: 1260
<212> TYPE: DNA
<213> ORGANISM: Mycoplasma hyopneumoniae

<400> SEQUENCE: 1
atgaaaaaaa tgcttagaaa aaaattcttg tattcatcag ctatttatgc aacttcgctt 60
gcatcaatta ttgcatttgt tgcagcaggt tgtggacaga cagaatcagg ttcgacttct 120
gattctaaac cacaagccga gacgctaaaa cataaagtaa gtaatgattc tattcgaata 180
gcactaaccg atccggataa tcctcgatga attagtgctc aaaaagatat tatttcttat 240
gttgatgaaa cagaggcagc aacttcaaca attacaaaaa accaggatgc acagaataac 300
tgactcactc agcaagctaa tttaagccca gcaccaaaag gatttattat tgcccctgaa 360

-continued

```
aatggaagtg gagttggaac tgctgttaat acaattgctg ataaaggaat tccgattgtt    420

gcctatgatc gactaattac tggatctgat aaatatgatt ggtatgtttc ttttgataat    480

gaaaaagttg gcgaattaca aggtctttca cttgcagcgg gtctattagg aaaagaagat    540

ggtgcttttg attcaattga tcaaatgaat gaatatctaa aatcacatat gccccaagag    600

acaatttctt tttatacaat cgcgggttcc caagatgata ataactccca atatttttat    660

aatggtgcaa tgaaagtact taaagaatta atgaaaaatt cgggaaataa gataattgat    720

ttatctcctg aaggcgaaaa tgctgtttat gtcccaggat gaaattatgg aactgccggt    780

caaagaatcc aatcttttct aacaattaac aaagatccag caggtggtaa taaaatcaaa    840

gctgttggtt caaaaccagc ttctattttc aaaggatttc ttgccccaaa tgatggaatg    900

gccgarcaag caatcaccaa attaaaactt gaaggatttg atacccaaaa aatctttgta    960

actggtcaag attataatga taaagccaaa acttttatca aagacggcga tcaaaatatg   1020

acaatttata aacctgataa agttttagga aaagttgctg ttgaagttct tcgggtttta   1080

attgcaaaga aaaataaagc atccagatca gaagtcgaaa acgaactaaa agcaaaacta   1140

ccaaatattt catttaaata tgataatcaa acatataaag tgcaaggtaa aaatattaat   1200

acaattttag taagtccagt aattgttaca aaagctaatg ttgataatcc tgatgcctaa   1260


<210> SEQ ID NO 2
<211> LENGTH: 419
<212> TYPE: PRT
<213> ORGANISM: Mycoplasma hyopneumoniae

<400> SEQUENCE: 2

Met Lys Lys Met Leu Arg Lys Lys Phe Leu Tyr Ser Ser Ala Ile Tyr
1               5                   10                  15

Ala Thr Ser Leu Ala Ser Ile Ile Ala Phe Val Ala Ala Gly Cys Gly
            20                  25                  30

Gln Thr Glu Ser Gly Ser Thr Ser Asp Ser Lys Pro Gln Ala Glu Thr
        35                  40                  45

Leu Lys His Lys Val Ser Asn Asp Ser Ile Arg Ile Ala Leu Thr Asp
    50                  55                  60

Pro Asp Asn Pro Arg Trp Ile Ser Ala Gln Lys Asp Ile Ile Ser Tyr
65                  70                  75                  80

Val Asp Glu Thr Glu Ala Ala Thr Ser Thr Ile Thr Lys Asn Gln Asp
                85                  90                  95

Ala Gln Asn Asn Trp Leu Thr Gln Gln Ala Asn Leu Ser Pro Ala Pro
            100                 105                 110

Lys Gly Phe Ile Ile Ala Pro Glu Asn Gly Ser Gly Val Gly Thr Ala
        115                 120                 125

Val Asn Thr Ile Ala Asp Lys Gly Ile Pro Ile Val Ala Tyr Asp Arg
    130                 135                 140

Leu Ile Thr Gly Ser Asp Lys Tyr Asp Trp Tyr Val Ser Phe Asp Asn
145                 150                 155                 160

Glu Lys Val Gly Glu Leu Gln Gly Leu Ser Leu Ala Ala Gly Leu Leu
                165                 170                 175

Gly Lys Glu Asp Gly Ala Phe Asp Ser Ile Asp Gln Met Asn Glu Tyr
            180                 185                 190

Leu Lys Ser His Met Pro Gln Glu Thr Ile Ser Phe Tyr Thr Ile Ala
        195                 200                 205

Gly Ser Gln Asp Asp Asn Asn Ser Gln Tyr Phe Tyr Asn Gly Ala Met
    210                 215                 220
```

-continued

Lys Val Leu Lys Glu Leu Met Lys Asn Ser Gly Asn Lys Ile Ile Asp
225 230 235 240

Leu Ser Pro Glu Gly Glu Asn Ala Val Tyr Val Pro Gly Trp Asn Tyr
245 250 255

Gly Thr Ala Gly Gln Arg Ile Gln Ser Phe Leu Thr Ile Asn Lys Asp
260 265 270

Pro Ala Gly Gly Asn Lys Ile Lys Ala Val Gly Ser Lys Pro Ala Ser
275 280 285

Ile Phe Lys Gly Phe Leu Ala Pro Asn Asp Gly Met Ala Glu Gln Ala
290 295 300

Ile Thr Lys Leu Lys Leu Glu Gly Phe Asp Thr Gln Lys Ile Phe Val
305 310 315 320

Thr Gly Gln Asp Tyr Asn Asp Lys Ala Lys Thr Phe Ile Lys Asp Gly
325 330 335

Asp Gln Asn Met Thr Ile Tyr Lys Pro Asp Lys Val Leu Gly Lys Val
340 345 350

Ala Val Glu Val Leu Arg Val Leu Ile Ala Lys Lys Asn Lys Ala Ser
355 360 365

Arg Ser Glu Val Glu Asn Glu Leu Lys Ala Lys Leu Pro Asn Ile Ser
370 375 380

Phe Lys Tyr Asp Asn Gln Thr Tyr Lys Val Gln Gly Lys Asn Ile Asn
385 390 395 400

Thr Ile Leu Val Ser Pro Val Ile Val Thr Lys Ala Asn Val Asp Asn
405 410 415

Pro Asp Ala

<210> SEQ ID NO 3
<211> LENGTH: 3324
<212> TYPE: DNA
<213> ORGANISM: Mycoplasma hyopneumoniae

<400> SEQUENCE: 3
atgagtaaaa aatcaaaaac atttaaaatt ggtttgactg ccggaattgt tggtcttgga 60
gtttttggtc taactgtcgg acttagcagc ttggcaaaat acagatcaga aagtccacga 120
aagattgcaa atgattttgc cgcaaaagtt tcaacattag cttttagtcc ttatgctttt 180
gagactgatt ctgattataa aatagtcaaa aggtgactag ttgattctaa taacaatatt 240
agaaataaag aaaaagttat tgattccttt tcctttttta ctaaaaacgg tgatcagtta 300
gaaaaaatta attttcaaga tcctgaatat accaaggcga agataacttt tgagattctt 360
gaaattatcc ctgatgatgt caatcaaaat tttaaggtaa aatttcaggc attacaaaaa 420
cttcataatg gtgatattgc caaatctgat atttatgagc aaacagttgc ttttgccaaa 480
cagtcaaatc ttttagttgc cgaatttaat ttttcgctta aaaaaattac cgaaaaatta 540
aatcaacaaa ttgaaaattt atcaacaaaa attacaaatt ttgctgatga aaaaacaagc 600
agccaaaaag atccctcaac tctaagagct attgacttcc aatacgattt aaatacagcg 660
cgaaatcctg aggatttaga tataaagctt gctaattatt ttccagtact taaaaattta 720
ataaacagac taaataatgc tcctgagaat aaattaccta ataatttggg taatattttt 780
gaatttagct ttgcaaaaga tagttcaact aatcaatatg taagtatcca gaaccaaatt 840
ccttcgctgt ttttaaaagc agatcttagt caaagtgccc gtgaaatttt agctagccca 900
gatgaagttc agccagttat taacatttta agattaatga aaaaagataa ttcttcttat 960

-continued

```
tttctaaatt ttgaggattt tgttaataat ttaacactga aaaatatgca aaaagaagat   1020
ttaaatgcaa agggtcaaaa tctttctgcc tatgaatttc tagcagatat taaatctgga   1080
tttttccctg gagacaagag atccagtcat accaaggcag aaattagtaa tcttttaaat   1140
aaaaaagaaa atatttatga ctttggtaaa tacaatggaa aattcaacga ccgtcttaac   1200
tcgccaaatt tagaatatag cctagatgca gcaagcgcaa gtcttgataa aaaagataaa   1260
tcaatagttt taattcccta ccgccttgaa attaaagata aatttttgc cgatgattta   1320
tatccagata caaaagataa tattctcgta aaagaaggga ttcttaaatt aactggattt   1380
aaaaaaggct caaaaattga tctccctaat atcaatcagc aaatttttaa aaccgaatat   1440
ttaccatttt ttgaaaaagg taaagaagaa caagcaaaat tagactatgg taatatctta   1500
aatccatata atactcaact tgccaaagtt gaagttgaag ctctttttaa agggaataaa   1560
aaccaagaaa tctatcaagc acttgatgga aattatgcct atgaattcgg ggcctttaaa   1620
tccgtgctta attcctgaac aggaaaaatt cagcatcctg aaaaagctga tatccaaaga   1680
tttacaagac atttagaaca agttaaaatt ggttctaatt cagttttaaa tcaaccacaa   1740
acaacaaaag aacaagtaat ttcaagtctt aaaagtaata actttttaa aaatggacat   1800
caagttgcaa gttatttcca ggatttactc accaaggaca aattaacaat tttagagact   1860
ctttatgatc tagcaaaaaa atggggacta gaaactaaca gagcacaatt cccaaaaggg   1920
gttttccaat atacaaaaga tatttttgca gaagcagata aattaaaatt tttggaattg   1980
aagaaaaagg atccttacaa tcagataaaa gaaattcacc aactttcctt taatatttta   2040
gcccgtaacg atgtaataaa atctgatgga ttttacggag ttttattatt gccccaaagt   2100
gtaaaaactg aattagaagg caaaaatgag gcgcaaattt ttgaagcgct taaaaagtat   2160
tctttaattg agaactcggc ttttaaaact actattttag ataaaaattt acttgaaggg   2220
actgatttta aaaccttcgg tgattttta aaagcatttt tccttaaagc agcccaattt   2280
aataattttg ctccttgagc aaaattagac gataatcttc agtattcatt tgaagctatc   2340
aaaaaagggg aaactacaaa agaaggtaaa agagaagaag tagataaaaa agttaaggaa   2400
ttggataata aaataaaagg tatattgcct cagcccccag cagcaaaacc agaagcagca   2460
aaaccagtag cggctaaacc agaaacaaca aaaccagtag cagctaaacc tgaagcagct   2520
aaacctgaag cagcaaaacc agtagcggct aaaccagaag cagcaaaacc agtagcggct   2580
aaaccagaag cagcaaaacc agtagcggct aaaccagaag cagcaaaacc agtagcggct   2640
aaaccagaag cagcaaaacc agttgctact aatactggct tttcacttac aaataaacca   2700
aaagaagact atttcccaat ggcttttagt tataaattag aatatactga cgaaaataaa   2760
ttaagcctaa aaacaccgga aattaatgta tttttagaac tagttcatca aagcgagtat   2820
gaagaacaag aaataataaa ggaactagat aaaactgttt taaatcttca atatcaattc   2880
caggaagtca aggtaactag tgaccaatat cagaaactta gccacccaat gatgaccgaa   2940
ggatcttcaa atcaaggtaa aaaaagcgaa ggaactccta accaaggtaa aaaagcagaa   3000
ggcgcgccta accaaggtaa aaaagccgaa ggaactccta accaagggaa aaaagcagag   3060
ggagcaccta gtcaacaaag cccaactacc gaattaacta attaccttcc tgacttaggt   3120
aaaaaaattg acgaaatcat taaaaaacaa ggtaaaaatt gaaaaacaga ggttgaacta   3180
atcgaggata atatcgctgg agatgctaaa ttgctatact ttatcctaag ggatgattca   3240
aaatccggtg atcctaaaaa atcaagtcta aaagttaaaa taacagtaaa acaaagtaat   3300
aataatcagg aaccagaatc taaa                                          3324
```

<210> SEQ ID NO 4
<211> LENGTH: 1108
<212> TYPE: PRT
<213> ORGANISM: Mycoplasma hyopneumoniae

<400> SEQUENCE: 4

Met Ser Lys Lys Ser Lys Thr Phe Lys Ile Gly Leu Thr Ala Gly Ile
1 5 10 15

Val Gly Leu Gly Val Phe Gly Leu Thr Val Gly Leu Ser Ser Leu Ala
20 25 30

Lys Tyr Arg Ser Glu Ser Pro Arg Lys Ile Ala Asn Asp Phe Ala Ala
35 40 45

Lys Val Ser Thr Leu Ala Phe Ser Pro Tyr Ala Phe Glu Thr Asp Ser
50 55 60

Asp Tyr Lys Ile Val Lys Arg Trp Leu Val Asp Ser Asn Asn Asn Ile
65 70 75 80

Arg Asn Lys Glu Lys Val Ile Asp Ser Phe Ser Phe Phe Thr Lys Asn
85 90 95

Gly Asp Gln Leu Glu Lys Ile Asn Phe Gln Asp Pro Glu Tyr Thr Lys
100 105 110

Ala Lys Ile Thr Phe Glu Ile Leu Glu Ile Ile Pro Asp Asp Val Asn
115 120 125

Gln Asn Phe Lys Val Lys Phe Gln Ala Leu Gln Lys Leu His Asn Gly
130 135 140

Asp Ile Ala Lys Ser Asp Ile Tyr Glu Gln Thr Val Ala Phe Ala Lys
145 150 155 160

Gln Ser Asn Leu Leu Val Ala Glu Phe Asn Phe Ser Leu Lys Lys Ile
165 170 175

Thr Glu Lys Leu Asn Gln Gln Ile Glu Asn Leu Ser Thr Lys Ile Thr
180 185 190

Asn Phe Ala Asp Glu Lys Thr Ser Ser Gln Lys Asp Pro Ser Thr Leu
195 200 205

Arg Ala Ile Asp Phe Gln Tyr Asp Leu Asn Thr Ala Arg Asn Pro Glu
210 215 220

Asp Leu Asp Ile Lys Leu Ala Asn Tyr Phe Pro Val Leu Lys Asn Leu
225 230 235 240

Ile Asn Arg Leu Asn Asn Ala Pro Glu Asn Lys Leu Pro Asn Asn Leu
245 250 255

Gly Asn Ile Phe Glu Phe Ser Phe Ala Lys Asp Ser Ser Thr Asn Gln
260 265 270

Tyr Val Ser Ile Gln Asn Gln Ile Pro Ser Leu Phe Leu Lys Ala Asp
275 280 285

Leu Ser Gln Ser Ala Arg Glu Ile Leu Ala Ser Pro Asp Glu Val Gln
290 295 300

Pro Val Ile Asn Ile Leu Arg Leu Met Lys Lys Asp Asn Ser Ser Tyr
305 310 315 320

Phe Leu Asn Phe Glu Asp Phe Val Asn Asn Leu Thr Leu Lys Asn Met
325 330 335

Gln Lys Glu Asp Leu Asn Ala Lys Gly Gln Asn Leu Ser Ala Tyr Glu
340 345 350

Phe Leu Ala Asp Ile Lys Ser Gly Phe Phe Pro Gly Asp Lys Arg Ser
355 360 365

Ser His Thr Lys Ala Glu Ile Ser Asn Leu Leu Asn Lys Lys Glu Asn

```
    370                 375                 380

Ile Tyr Asp Phe Gly Lys Tyr Asn Gly Lys Phe Asn Asp Arg Leu Asn
385                 390                 395                 400

Ser Pro Asn Leu Glu Tyr Ser Leu Asp Ala Ala Ser Ala Ser Leu Asp
                405                 410                 415

Lys Lys Asp Lys Ser Ile Val Leu Ile Pro Tyr Arg Leu Glu Ile Lys
            420                 425                 430

Asp Lys Phe Phe Ala Asp Asp Leu Tyr Pro Asp Thr Lys Asp Asn Ile
        435                 440                 445

Leu Val Lys Glu Gly Ile Leu Lys Leu Thr Gly Phe Lys Lys Gly Ser
    450                 455                 460

Lys Ile Asp Leu Pro Asn Ile Asn Gln Gln Ile Phe Lys Thr Glu Tyr
465                 470                 475                 480

Leu Pro Phe Phe Glu Lys Gly Lys Glu Glu Gln Ala Lys Leu Asp Tyr
                485                 490                 495

Gly Asn Ile Leu Asn Pro Tyr Asn Thr Gln Leu Ala Lys Val Glu Val
            500                 505                 510

Glu Ala Leu Phe Lys Gly Asn Lys Asn Gln Glu Ile Tyr Gln Ala Leu
        515                 520                 525

Asp Gly Asn Tyr Ala Tyr Glu Phe Gly Ala Phe Lys Ser Val Leu Asn
    530                 535                 540

Ser Trp Thr Gly Lys Ile Gln His Pro Glu Lys Ala Asp Ile Gln Arg
545                 550                 555                 560

Phe Thr Arg His Leu Glu Gln Val Lys Ile Gly Ser Asn Ser Val Leu
                565                 570                 575

Asn Gln Pro Gln Thr Thr Lys Glu Gln Val Ile Ser Ser Leu Lys Ser
            580                 585                 590

Asn Asn Phe Phe Lys Asn Gly His Gln Val Ala Ser Tyr Phe Gln Asp
        595                 600                 605

Leu Leu Thr Lys Asp Lys Leu Thr Ile Leu Glu Thr Leu Tyr Asp Leu
    610                 615                 620

Ala Lys Lys Trp Gly Leu Glu Thr Asn Arg Ala Gln Phe Pro Lys Gly
625                 630                 635                 640

Val Phe Gln Tyr Thr Lys Asp Ile Phe Ala Glu Ala Asp Lys Leu Lys
                645                 650                 655

Phe Leu Glu Leu Lys Lys Lys Asp Pro Tyr Asn Gln Ile Lys Glu Ile
            660                 665                 670

His Gln Leu Ser Phe Asn Ile Leu Ala Arg Asn Asp Val Ile Lys Ser
        675                 680                 685

Asp Gly Phe Tyr Gly Val Leu Leu Leu Pro Gln Ser Val Lys Thr Glu
    690                 695                 700

Leu Glu Gly Lys Asn Glu Ala Gln Ile Phe Glu Ala Leu Lys Lys Tyr
705                 710                 715                 720

Ser Leu Ile Glu Asn Ser Ala Phe Lys Thr Thr Ile Leu Asp Lys Asn
                725                 730                 735

Leu Leu Glu Gly Thr Asp Phe Lys Thr Phe Gly Asp Phe Leu Lys Ala
            740                 745                 750

Phe Phe Leu Lys Ala Ala Gln Phe Asn Asn Phe Ala Pro Trp Ala Lys
        755                 760                 765

Leu Asp Asp Asn Leu Gln Tyr Ser Phe Glu Ala Ile Lys Lys Gly Glu
    770                 775                 780

Thr Thr Lys Glu Gly Lys Arg Glu Glu Val Asp Lys Lys Val Lys Glu
785                 790                 795                 800
```

-continued

```
Leu Asp Asn Lys Ile Lys Gly Ile Leu Pro Gln Pro Pro Ala Ala Lys
                805                 810                 815

Pro Glu Ala Ala Lys Pro Val Ala Ala Lys Pro Glu Thr Thr Lys Pro
            820                 825                 830

Val Ala Ala Lys Pro Glu Ala Ala Lys Pro Glu Ala Ala Lys Pro Val
        835                 840                 845

Ala Ala Lys Pro Glu Ala Ala Lys Pro Val Ala Ala Lys Pro Glu Ala
    850                 855                 860

Ala Lys Pro Val Ala Ala Lys Pro Glu Ala Ala Lys Pro Val Ala Ala
865                 870                 875                 880

Lys Pro Glu Ala Ala Lys Pro Val Ala Thr Asn Thr Gly Phe Ser Leu
                885                 890                 895

Thr Asn Lys Pro Lys Glu Asp Tyr Phe Pro Met Ala Phe Ser Tyr Lys
            900                 905                 910

Leu Glu Tyr Thr Asp Glu Asn Lys Leu Ser Leu Lys Thr Pro Glu Ile
        915                 920                 925

Asn Val Phe Leu Glu Leu Val His Gln Ser Glu Tyr Glu Glu Gln Glu
    930                 935                 940

Ile Ile Lys Glu Leu Asp Lys Thr Val Leu Asn Leu Gln Tyr Gln Phe
945                 950                 955                 960

Gln Glu Val Lys Val Thr Ser Asp Gln Tyr Gln Lys Leu Ser His Pro
                965                 970                 975

Met Met Thr Glu Gly Ser Ser Asn Gln Gly Lys Lys Ser Glu Gly Thr
            980                 985                 990

Pro Asn Gln Gly Lys Lys Ala Glu  Gly Ala Pro Asn Gln  Gly Lys Lys
        995                 1000                 1005

Ala Glu  Gly Thr Pro Asn Gln  Gly Lys Lys Ala Glu  Gly Ala Pro
    1010                 1015                 1020

Ser Gln  Gln Ser Pro Thr Thr  Glu Leu Thr Asn Tyr  Leu Pro Asp
    1025                 1030                 1035

Leu Gly  Lys Lys Ile Asp Glu  Ile Ile Lys Lys Gln  Gly Lys Asn
    1040                 1045                 1050

Trp Lys  Thr Glu Val Glu Leu  Ile Glu Asp Asn Ile  Ala Gly Asp
    1055                 1060                 1065

Ala Lys  Leu Leu Tyr Phe Ile  Leu Arg Asp Asp Ser  Lys Ser Gly
    1070                 1075                 1080

Asp Pro  Lys Lys Ser Ser Leu  Lys Val Lys Ile Thr  Val Lys Gln
    1085                 1090                 1095

Ser Asn  Asn Asn Gln Glu Pro  Glu Ser Lys
    1100                 1105
```

<210> SEQ ID NO 5
<211> LENGTH: 1773
<212> TYPE: DNA
<213> ORGANISM: Porcine circovirus

<400> SEQUENCE: 5

```
ggtacctccg tggattgttc tccagcagtc ttccaaaatt gcaaagtagt aatcctccga      60

tagagagctt ctacagctgg gacagcagtt gaggagtacc attcctgggg ggcctgattg     120

ctggtaatca aaatactgcg ggccaaaaaa ggaacagtac cccctttagt ctctacagtc     180

aatggatacc ggtcacacag tctcagtaga tcatcccaag gtaaccagcc ataaaaatca     240

tccaaaacaa caacttcttc tccatgatat ccatcccacc acttatttct actaggcttc     300
```

-continued cagtaggtgt ccctaggctc agcaaaatta cgggcccact ggctcttccc acaaccgggc 360
gggcccacta tgacgtgtac agctgtcttc caatcacgct gctgcatctt cccgctcact 420
ttcaaaagtt cagccagccc gcggaaattt ctcacatacg ttacaggaaa ctgctcggct 480
acagtcacca aagaccccgt ctccaaaagg gtactcacag cagtagacag gtcgctgcgc 540
ttcccctggt tccgcggagc tccacactcg ataagtatgt ggccttcttt actgcagtat 600
tctttattct gctggtcggt tcctttcgct ttctcgatgt ggcagcgggc accaaaatac 660
cacttcacct tgttaaaagt ctgcttctta gcaaaattcg caaacccctg gaggtgagga 720
gttctaccct cttccaaacc ttcctcgcca caaacaaaat aatcaaaaag ggagattgga 780
agctcccgta ttttgttttt ctcctcctcg gaaggattat taagggtgaa cacccacctc 840
ttatggggtt gcgggccgct ttcttgcttg gcattttca ctgacgctgc cgaggtgctg 900
ccgctgccga agtgcgctgg taatactaca gcagcgcact tctttcactt ttataggatg 960
acgtatccaa ggaggcgtta ccgcagaaga agacaccgcc cccgcagcca tcttggccag 1020
atcctccgcc gccgcccctg gctcgtccac ccccgccacc gctaccgttg gagaaggaaa 1080
aatggcatct tcaacacccg cctctcccgc accttcggat atactgtcaa ggctaccaca 1140
gtcagaacgc cctcctgggc ggtggacatg atgagattta atattgacga ctttgttccc 1200
ccgggagggg ggaccaacaa aatctctata ccctttgaat actacagaat aagaaaggtt 1260
aaggttgaat tctggccctg ctcccccatc acccagggtg ataggggagt gggctccact 1320
gctgttattc tagatgataa ctttgtaaca aaggccacag ccctaaccta tgacccatat 1380
gtaaactact cctcccgcca tacaatcccc caacccttct cctaccactc ccgttacttc 1440
acacccaaac ctgttcttga ctccaccatt gattacttcc aaccaaataa caaaaggaat 1500
cagctttgga tgaggctaca aacctctaga aatgtggacc acgtaggcct cggcactgcg 1560
ttcgaaaaca gtatatacga ccaggactac aatatccgtg taaccatgta tgtacaattc 1620
agagaattta atcttaaaga ccccccactt aaaccctaaa tgaataaaaa taaaaaccat 1680
tacgatgtga taacaaaaaa gactcagtaa tttattttat atgggaaaag ggcacagggt 1740
gggtccactg cttcaaatcg gccttcgggt acc 1773

<210> SEQ ID NO 6
<211> LENGTH: 702
<212> TYPE: DNA
<213> ORGANISM: Porcine circovirus

<400> SEQUENCE: 6
atgacgtatc caaggaggcg ttaccgcaga agaagacacc gcccccgcag ccatcttggc 60
cagatcctcc gccgccgccc ctggctcgtc cacccccgcc accgctaccg ttggagaagg 120
aaaaatggca tcttcaacac ccgcctctcc cgcaccttcg gatatactgt caaggctacc 180
acagtcagaa cgccctcctg ggcggtggac atgatgagat ttaatattga cgactttgtt 240
cccccgggag gggggaccaa caaaatctct ataccctttg aatactacag aataagaaag 300
gttaaggttg aattctggcc ctgctccccc atcacccagg gtgatagggg agtgggctcc 360
actgctgtta ttctagatga taactttgta acaaaggcca cagccctaac ctatgaccca 420
tatgtaaact actcctcccg ccatacaatc cccccaaccct tctcctacca ctcccgttac 480
ttcacaccca aacctgttct tgactccacc attgattact tccaaccaaa taacaaaagg 540
aatcagcttt ggatgaggct acaaacctct agaaatgtgg accacgtagg cctcggcact 600
gcgttcgaaa acagtatata cgaccaggac tacaatatcc gtgtaaccat gtatgtacaa 660
ttcagagaat ttaatcttaa agaccccca cttaaaccct aa 702

<210> SEQ ID NO 7
<211> LENGTH: 233
<212> TYPE: PRT
<213> ORGANISM: Porcine circovirus

<400> SEQUENCE: 7

```
Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 8
<211> LENGTH: 1767
<212> TYPE: DNA
<213> ORGANISM: Porcine circovirus

<400> SEQUENCE: 8

```
ggtacctccg tggattgttc tccagcagtc ttccaaaatt gcaaagtagt aatcctccga     60

tagagagctt ctacagctgg gacagcagtt gaggagtacc attcctgggg ggcctgattg    120

ctggtaatca aaatactgcg ggccaaaaaa ggaacagtac cccctttagt ctctacagtc    180

aatggatacc ggtcacacag tctcagtaga tcatcccaag gtaaccagcc ataaaaatca    240

tccaaaacaa caacttcttc tccatgatat ccatcccacc acttatttct actaggcttc    300

cagtaggtgt cgctaggctc agcaaaatta cgggcccact ggctcttccc acaaccgggc    360

gggcccacta tgacgtgtac agctgtcttc caatcacgct gctgcatctt cccgctcact    420

ttcaaaagtt cagccagccc gcggaaattt ctcacatacg ttacagggaa ctgctcggct    480
```

```
acagtcacca aagaccccgt ctccaaaagg gtactcacag cagtagacag gtcgctgcgc    540
ttcccctggt tccgcggagc tccacactcg ataagtatgt ggccttcttt actgcagtat    600
tctttattct gctggtcggt tcctttcgct ttctcgatgt ggcagcgggc accaaaatac    660
cacttcacct tgttaaaagt ctgcttctta gcaaaattcg caaacccctg gaggtgagga    720
gttctaccct cttccaaacc ttcctctccg caaacaaaat aatcaaaaag ggagattgga    780
agctcccgta ttttgttttt ctcctcctcg gaaggattat taagggtgaa cacccacctc    840
ttatggggtt gcgggccgct ttcctgcttg gcattttca ctgacgctgc cgaggtgctg     900
ccgctgccga agtgcgctgg taatactaca gcagcgcact tctttcactt ttataggatg    960
acgtatccaa ggaggcgtta ccgcagaaga agacaccgcc cccgcagcca tcttggccag   1020
atcctccgcc gccgcccctg gctcgtccac ccccgccacc gctaccgttg gagaaggaaa   1080
aatggcatct tcaacacccg cctctcccgc accttcggat atactgtcaa ggctaccaca   1140
gtcagaacgc cctcctgggc ggtggacatg atgagattta atattgacga ctttgttccc   1200
ccgggagggg ggaccaacaa aatctctata ccctttgaat actacagaat aagaaaggtt   1260
aaggttgaat tctggccctg ctcccccatc acccagggtg ataggggagt gggctccact   1320
gctgttattc tagatgataa ctttgtaaca aaggccacag ccctaaccta tgacccatat   1380
gtaaactact cctcccgcca tacaatcgcc caacccttct cctaccactc ccgttacttc   1440
acacccaaac ctgttcttga ctccaccatt gattacttcc aaccaaataa caaaaggaat   1500
cagctttgga tgaggctaca aacctctaga aatgtggacc acgtaggcct cggcactgcg   1560
ttcgaaaaca gtatatacga ccaggactac aatatccgtg taaccatgta tgtacaattc   1620
agagaattta atcttaaaga ccccccactt aaaccctaaa tgaataaaaa taaaaaccat   1680
tacgatgtga taacaaaaaa gactcagtaa tttattttat atgggaaaag ggcacagggt   1740
gggtccactg cttcaaatcg gccttcg                                       1767
```

<210> SEQ ID NO 9
<211> LENGTH: 702
<212> TYPE: DNA
<213> ORGANISM: Porcine circovirus

<400> SEQUENCE: 9

```
atgacgtatc caaggaggcg ttaccgcaga agaagacacc gcccccgcag ccatcttggc     60
cagatcctcc gccgccgccc ctggctcgtc cacccccgcc accgctaccg ttggagaagg    120
aaaaatggca tcttcaacac ccgcctctcc cgcaccttcg gatatactgt caaggctacc    180
acagtcagaa cgccctcctg ggcggtggac atgatgagat ttaatattga cgactttgtt    240
cccccgggag gggggaccaa caaaatctct ataccctttg aatactacag aataagaaag    300
gttaaggttg aattctggcc ctgctccccc atcacccagg gtgatagggg agtgggctcc    360
actgctgtta ttctagatga taactttgta acaaaggcca cagccctaac ctatgaccca    420
tatgtaaact actcctcccg ccatacaatc gcccaaccct tctcctacca ctcccgttac    480
ttcacaccca aacctgttct tgactccacc attgattact tccaaccaaa taacaaaagg    540
aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
ttcagagaat ttaatcttaa agacccccca cttaaaccct aa                       702
```

<210> SEQ ID NO 10

<211> LENGTH: 233
<212> TYPE: PRT
<213> ORGANISM: Porcine circovirus

<400> SEQUENCE: 10

```
Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Ala Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 11
<211> LENGTH: 233
<212> TYPE: PRT
<213> ORGANISM: Porcine circovirus

<400> SEQUENCE: 11

```
Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110
```

-continued

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230

<210> SEQ ID NO 12
<211> LENGTH: 713
<212> TYPE: DNA
<213> ORGANISM: Porcine circovirus

<400> SEQUENCE: 12
cagctatgac gtatccaagg aggcgttacc gcagaagaag acaccgcccc cgcagccatc 60
ttggccagat cctccgccgc cgcccctggc tcgtccaccc ccgccaccgc taccgttgga 120
gaaggaaaaa tggcatcttc aacacccgcc tctcccgcac cttcggatat actgtggaga 180
aggaaaaatg gcatcttcaa cacccgcctc tcccgcacct tcggatatac tgtgacgact 240
ttgttccccc gggagggggg accaacaaaa tctctatacc ctttgaatac tacagaataa 300
gaaaggttaa ggttgaattc tggccctgct cccccatcac ccagggtgat aggggagtgg 360
gctccactgc tgttattcta gatgataact ttgtaacaaa ggccacagcc ctaacctatg 420
acccatatgt aaactactcc tcccgccata caatccccca acccttctcc taccactccc 480
gttacttcac acccaaacct gttcttgact ccactattga ttacttccaa ccaaataaca 540
aaaggaatca gctttggctg aggctacaaa cctctagaaa tgtggaccac gtaggcctcg 600
gcactgcgtt cgaaaacagt aaatacgacc aggactacaa tatccgtgta accatgtatg 660
tacaattcag agaatttaat cttaaagacc ccccacttaa accctaaatg aat 713

<210> SEQ ID NO 13
<211> LENGTH: 233
<212> TYPE: PRT
<213> ORGANISM: Porcine circovirus

<400> SEQUENCE: 13

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

-continued

```
Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230


<210> SEQ ID NO 14
<211> LENGTH: 713
<212> TYPE: DNA
<213> ORGANISM: Porcine circovirus

<400> SEQUENCE: 14

ccgccatgac gtatccaagg aggcgttacc gcagaagaag acaccgcccc cgcagccatc      60

ttggccagat cctccgccgc cgcccctggc tcgtccaccc ccgccaccgc taccgttgga     120

gaaggaaaaa tggcatcttc aacacccgcc tctcccgcac cttcggatat actgtcaagg     180

ctaccacagt cacaacgccc tcctgggcgg tggacatgat gagatttaat attgacgact     240

ttgttccccc gggagggggg accaacaaaa tctctatacc ctttgaatac tacagaataa     300

gaaaggttaa ggttgaattc tggccctgct cccccatcac ccagggtgat aggggagtgg     360

gctccactgc tgttattcta gatgataact ttgtaacaaa ggccacagcc ctaacctatg     420

acccatatgt aaactactcc tcccgccata caatccccca acccttctcc taccactccc     480

gttacttcac acccaaacct gttcttgact ccactattga ttacttccaa ccaaataaca     540

aaaggaatca gctttggctg aggctacaaa cctctagaaa tgtggaccac gtaggcctcg     600

gcactgcgtt cgaaaacagt aaatacgacc aggactacaa tatccgtgta accatgtatg     660

tacaattcag agaatttaat cttaaagacc ccccacttga accctaagaa ttc             713


<210> SEQ ID NO 15
<211> LENGTH: 233
<212> TYPE: PRT
<213> ORGANISM: Porcine circovirus

<400> SEQUENCE: 15

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45
```

```
Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 16
<211> LENGTH: 15450
<212> TYPE: DNA
<213> ORGANISM: Porcine reproductive and respiratory syndrome virus

<400> SEQUENCE: 16

```
atgacgtata ggtgttggct ctatgccacg gcatttgtat tgtcaggagc tgtggccatt     60

ggcacagccc aaaacttgct gcacggaaaa cgcccttctg tgacagcctt cttcagggga    120

gcttaggggt ctgtccctag caccttgctt ctggagttgc actgctttac ggtctctcca    180

cccctttaac catgtctggg atacttgatc ggtgcacgtg cacccccaat gccagggtgt    240

ttatggcgga gggccaagtc tactgcacac gatgtctcag tgcacggtct ctccttcctc    300

tgaatctcca agttcctgag cttggggtgc tgggcctatt ttataggccc gaagagccac    360

tccggtggac gttgccacgt gcattcccca ctgtcgagtg ctcccctgcc ggggcctgct    420

ggctttctgc gatctttcca attgcacgaa tgaccagtgg aaacctgaac tttcaacaaa    480

gaatggtgcg ggttgcagct gagatttaca gagccggcca actcacccct gcagttttga    540

aggctctaca agtttatgaa cggggttgtc gctggtaccc cattgtcgga cctgtccctg    600

gagtggccgt ttacgccaac tccctacatg tgagtgacaa acctttcccg ggagcaactc    660

atgtgttaac caacctaccg ctcccgcaga ggcccaagcc tgaagacttt tgccctttttg   720

agtgtgctat ggctaacgtc tatgacattg gccataacgc cgtcatgtat gtggccagag    780

ggaaagtctc ctgggcccct cgtggcgggg atgaagtgaa atttgaaacc gtccccgaag    840

agttgaagtt gattgcgaac cgactccaca tctccttccc gccccaccac gcagtggaca    900

tgtctgagtt tgccttcata gcccctggga gtggtgtctc cttgcgggtc gagcaccaac    960

acggctgcct tcccgctgat actgtccctg atgggaactg ctggtggtac ttgtttgact   1020
```

-continued

```
tgctcccacc ggaagttcag aataaagaaa ttcgccgtgc taaccaattt ggctatcaaa   1080
ccaagcatgg tgtccatggc aagtacctac agcggaggct gcaagttaat ggtctccgag   1140
cagtgactga tacagatgga cctattgtcg tacagtactt ctctgttagg gagagttgga   1200
tccgccactt cagactggcg gaagaaccta gcctccctgg gtttgaagac ctcctcagaa   1260
taagggtaga gcctaatacg tcgccaatgg gtggcaaggg tgaaaaaatc ttccggtttg   1320
gcagtcacaa gtggtacggt gctggaaaga gagcaaggag agcacgctct ggtgcgactg   1380
ccacggtcgc tcaccgcgct ttgcccgctc gcgaagccca gcaggccaag aagctcgagg   1440
ttgccagcgc caacagggct gagcatctca agtactattc cccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgacccct gggatgaccc   1740
cttctttgct ccccccttgaa tgtgttcagg gttgttgtga gcataagagc ggtcttggtt   1800
tcccagacgt ggtcgaagtt tccggatttg accctgcctg tcttgaccga cttgctgaga   1860
taatgcactt gcctagcagt gtcatcccag ctgctctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaacctt tgtcaggtga   2040
ttgaggaatg ctgctgttcc cggaacaaag ccaaccgggc taccccggaa gaggttgcgg   2100
caaaagttga ccagtacctc cgtggtgcag caagccttgg agaatgcttg gccaagcttg   2160
agagggctcg cccgccgagc gcgacggaca cctcctttga ttggaatgtt gtgcttcctg   2220
gggttgagac ggcgaatcag acaaccaaac agctccatgt caaccagtgc cgcgctctgg   2280
ttcctgtcgt gactcaagag cctttggaca gagactcggt ccctctgacc gccttctcgc   2340
tgtccaattg ctactaccct gcacaaggtg acgaggtccg tcaccgtgag aggctaaact   2400
ccttgctctc taagttggag gggggttgttc gtgaggaata tgggctcacg ccaactggac   2460
ctggcccgcg acccgcactg ccgaacgggc tcgacgagct taaagaccag atggaggagg   2520
atctgctgaa attagtcaac gcccaggcaa cttcagaaat gatggcctgg gcagccgagc   2580
aggttgatct aaaagcttgg gtcaaaaatt acccacggtg gacaccgcca ccccctccac   2640
caagagttca gcctcgaaaa acgaagtctg tcaagagctt gctagagaac aagcctgtcc   2700
ctgctccgcg caggaaggtc agatctgatt gtggcagccc gattttgatg ggcgacaatg   2760
ttcctaacgg ttgggaagat tcgactgttg gtggtcccct tgatctttcg gcaccatccg   2820
agccgatgac acctctgagt gagcctgtac ttatttccag gccagtgaca tctttgagtg   2880
tgccggcccc agttcctgca ccgcgtagag ctgtgtcccg accgatgacg ccctcgagtg   2940
agccaatttt tgtgtctgca ctgcgacaca aatttcagca ggtggaaaaa gcaaatctgg   3000
cggcagcagc gccgatgtgc caggacgaac ccttagattt gtctgcatcc tcacagactg   3060
aatatgaggc ttccccccta acaccaccgc agaacgtggg cattctggag gtaagggggc   3120
aagaagctga ggaagttctg agtgaaatct cggatattct gaatgatacc aaccctgcac   3180
ctgtgtcatc aagcagctcc ctgtcaagtg ttaagatcac acgcccaaaa tactcagctc   3240
aagccattat cgactcgggc gggccctgca gtgggcacct ccaaagggaa aaagaagcat   3300
gcctccgcat catgcgtgaa gcttgtgatg cggccaagct tagtgaccct gccacgcagg   3360
aatggctttc tcgcatgtgg gatagggtgg acatgctgac ttggcgcaac acgtctgctt   3420
```

accaggcgtt tcgcacctta gatggcaggt ttgggtttct cccaaagatg atactcgaga 3480
cgccgccgcc ctacccgtgt gggtttgtga tgttgcctca cacccctgca ccttccgtga 3540
gtgcagagag cgaccttacc attggttcag tcgccactga agatattcca cgcatcctcg 3600
ggaaaataga aaataccggt gagatgatca accagggacc cttggcatcc tctgaggaag 3660
aaccggtata caaccaacct gccaaagact cccggatatc gtcgcggggg tctgacgaga 3720
gcacagcagc tccgtccgcg ggtacaggtg gcgccggctt atttactgat ttgccacctt 3780
cagacggcgt agatgcggac ggtggggggc cgttgcagac ggtaagaaag aaagctgaaa 3840
ggctcttcga ccaattgagc cgtcaggttt ttaacctcgt ctcccatctc cctgttttct 3900
tctcacacct cttcaaatct gacagtggtt attctccggg tgattggggt tttgcagctt 3960
ttactctatt ttgcctcttt ttgtgttaca gctacccatt cttcggtttc gttcccctct 4020
tgggtgtatt ttctgggtct tctcggcgtg tgcgcatggg ggtttttggc tgctggctgg 4080
cttttgctgt tggcctgttc aagcctgtgt ccgacccagt cggcactgct tgtgagtttg 4140
actcgccaga gtgcaggaac gtccttcatt cttttgagct tctcaaacct tgggaccctg 4200
ttcgcagcct tgttgtgggc cccgtcggtc tcggtcttgc cattcttggc aagttactgg 4260
gcggggcacg ctacatctgg catttttttgc ttaggcttgg cattgttgca gattgtatct 4320
tggctggagc ttatgtgctt tctcaaggta ggtgtaaaaa gtgctgggga tcttgtataa 4380
gaactgctcc taatgaaatc gccttcaacg tgttcccttt tacacgtgcg accaggtcgt 4440
cactcatcga cctgtgcgat cggttttgtg cgccaacagg catggacccc atttcctcg 4500 ccactgggtg gcgtgggtgc tggaccggcc gaagtcccat tgagcaaccc tctgaaaaac 4560
ccatcgcgtt cgcccagttg gatgaaaaga ggattacggc tagaactgtg gtcgctcagc 4620
cttatgatcc taatcaagcc gtgaagtgct tgcgggtgtt acaggcgggt ggggcgatgg 4680
tggccgaggc agtcccaaaa gtggccaaag tttctgctat tccattccga gccccttttt 4740
ttcccaccgg agtgaaagtt gatcccgagt gcaggatcgt ggttgacccc gatactttta 4800
ctacagccct ccggtctggt tactctacca caaacctcgt ccttggtgtg ggggactttg 4860
cccagctgaa tggactaaag atcaggcaaa tttccaagcc ttcgggagga ggcccacacc 4920
tcattgctgc cctgcatgtt gcctgctcga tggcgttgca catgcttgct ggggtttatg 4980
taacttcagt ggggtcttgc ggtgccggca ccaacgatcc atggtgcact aatccgtttg 5040
ccgttcctgg ctacggacca ggctctctct gcacgtccag attgtgcatc tcccaacatg 5100
gccttaccct gcccttgaca gcacttgtgg cgggattcgg tcttcaggaa atcgccttgg 5160
tcgttttgat tttcgtttcc atcggaggca tggctcatag gttgagttgt aaggctgata 5220
tgctgtgcat tttacttgca atcgccagct atgtttgggt acccttacc tggttgcttt 5280 gtgtgtttcc ttgttggttg cgctggttct ctttgcaccc ccttaccatc ctatggttgg 5340
tgtttttctt gatttctgta aatatgcctt cgggaatctt ggccgtggtg ttattggttt 5400
ctctttggct tttgggacgt tatactaaca ttgctggtct tgtcaccccc tatgatattc 5460
atcattacac cagtggcccc cgcggtgttg ccgccttggc taccgcacca gatggaacct 5520
acttggctgc cgtccgccgc gctgcgttga ctggtcgcac catgctgttc accccgtctc 5580
agcttgggtc ccttcttgag ggcgctttca gaactcgaaa gccctcactg aacaccgtca 5640
atgtggttgg gtcctccatg ggctctggtg gagtgttcac catcgacggg aaaattaggt 5700
gcgtgactgc cgcacatgtc cttacgggta attcggctag ggtttccgga gtcggcttca 5760

-continued

```
atcaaatgct tgactttgat gtgaaagggg acttcgccat agctgattgc ccgaattggc   5820
aaggagctgc tcccaagacc caattctgcg aggacggatg gactggccgt gcctattggc   5880
tgacatcctc tggcgtcgaa cccggtgtta ttgggaatgg attcgccttc tgcttcaccg   5940
cgtgcggcga ttccgggtcc ccagtgatca ccgaagctgg tgagattgtc ggcgttcaca   6000
caggatcaaa taaacaagga ggtggcatcg tcacgcgccc ttcaggccag ttttgtaacg   6060
tggcacccat caagctgagc gaattaagtg aattctttgc tggacccaag gtcccgctcg   6120
gtgatgtgaa ggttggcagc cacataatta aagacacgtg cgaagtacct tcagatcttt   6180
gcgccttgct tgctgccaaa cctgaactgg agggaggcct ctccaccgtc caacttctgt   6240
gtgtgttttt cctactgtgg agaatgatgg gacatgcctg gacgcccttg gttgctgtgg   6300
ggtttttcat tctgaatgag gttctcccag ctgtcctggt tcggagtgtt ttctcctttg   6360
ggatgtttgt gctatcttgg ctcacaccat ggtctgcgca agttctgatg atcaggcttc   6420
taacagcagc tcttaacagg aacagatggt cacttgcctt ttacagcctt ggtgcggtga   6480
ccggttttgt cgcagatctt gcggtaactc aagggcaccc gttgcaggca gtaatgaatt   6540
tgagcaccta tgccttcctg cctcggatga tggttgtgac ctcaccagtc ccagtgattg   6600
cgtgtggtgt tgtgcaccta cttgccatca ttttgtactt gttcaagtac cgcggcctgc   6660
acaatgttct tgttggtgat ggagcgtttt ctgcagcttt cttcttgcga tactttgccg   6720
agggaaagtt gagggaaggg gtgtcgcaat cctgcggaat gaatcatgag tcattgactg   6780
gtgccctcgc tatgagactc aatgacgagg acttggactt ccttacgaaa tggactgatt   6840
ttaagtgctt tgtttctgcg tccaacatga ggaatgcagc aggccaattc atcgaggctg   6900
cctatgcaaa agcacttaga attgaacttg cccagttggt gcaggttgat aaggttcgag   6960
gtactttggc caagcttgag gcttttgctg ataccgtggc accccaactc tcgcccggtg   7020
acattgttgt tgctcttggc catacgcctg ttggcagcat cttcgaccta aaggttggtg   7080
gtaccaagca tactctccaa gtcattgaga ccagagtcct tgccgggtcc aaaatgaccg   7140
tggcgcgcgt cgttgaccca acccccacgc ccccacccgc acccgtgccc atccccctcc   7200
caccgaaagt tctagagaat ggtcccaacg cctgggggga tggggaccgt ttgaataaga   7260
agaagaggcg taggatggaa accgtcggca tctttgtcat gggtgggaag aagtaccaga   7320
aattttggga caagaattcc ggtgatgtgt tttacgagga ggtccatgac aacacagatg   7380
cgtgggagtg cctcagagtt ggtgaccctg ccgactttaa ccctgagaag ggaactctgt   7440
gtgggcatac tactattgaa gataaggatt acaaagtcta cgcctcccca tctggcaaga   7500
agttcctggt ccccgtcaac ccagagagcg gaagagccca atgggaagct gcaaagcttt   7560
ccgtggagca ggcccttggc atgatgaatg tcgacggtga actgacggcc aaagaagtgg   7620
agaaactgaa aagaataatt gacaaacttc agggccttac taaggagcag tgtttaaact   7680
gctagccgcc agcggcttga cccgctgtgg tcgcggcggc ttggttgtta ctgagacagc   7740
ggtaaaaata gtcaaatttc acaaccggac tttcacccta gggcctgtga atttaaaagt   7800
ggccagtgag gttgagctga aagacgcggt cgagcacaac caacacccgg ttgcaagacc   7860
ggttgacggt ggtgttgtgc tcctgcgttc cgcagttcct tcgcttatag atgtcctgat   7920
ctccggtgct gacgcatctc ctaagttact cgctcgtcac gggccgggga acactgggat   7980
cgatggcacg ctttgggact ttgaggccga ggccaccaaa gaggaaattg cgctcagtgc   8040
gcaaataata caggcttgtg acattaggcg cggtgacgca cctgaaattg gtctccctta   8100
caagctgtac cctgttaggg gcaaccctga gcgggtaaaa ggagttttac agaatacaag   8160
```

-continued

```
gtttggagac ataccttaca aaacccccag tgacactggg agcccagtgc acgcggctgc   8220
ctgcctcacg cccaatgcca ctccggtgac tgatgggcgc tccgtcttgg ctactaccat   8280
gccctccggt tttgaattgt atgtaccgac cattccagcg tctgtccttg attatcttga   8340
ctctaggcct gactgcccca aacagttgac agagcacggc tgtgaggatg ccgcattgag   8400
agacctctcc aagtatgact tgtccaccca aggctttgtt ttacctgggg ttcttcgcct   8460
tgtgcgtaag tacctgtttg cccacgtggg taagtgcccg cccgttcatc ggccttccac   8520
ttaccctgcc aagaattcta tggctggaat aaatgggaac aggtttccaa ccaaggacat   8580
tcagagcgtc cccgaaatcg acgttctgtg cgcacaggcc gtgcgagaaa actggcaaac   8640
tgttacccct tgtaccctca agaaacagta ttgtgggaag aagaagacta ggacaatact   8700
cggcaccaat aatttcattg cgttggccca ccgggcagcg ttgagtggtg tcacccaggg   8760
cttcatgaaa aaggcgttta actcgcccat cgccctcggg aaaaacaaat ttaaggagct   8820
acagactccg atcttaggca ggtgccttga agctgatctt gcatcctgtg atcgatccac   8880
acctgcaatt gtccgctggt ttgccgccaa ccttctttat gaacttgcct gtgctgaaga   8940
gcacctaccg tcgtacgtgc tgaactgctg ccatgaccta ttggtcacgc agtccggcgc   9000
agtgactaag aggggtggcc tgtcgtctgg cgacccgatc acttctgtgt ctaacaccat   9060
ttacagcttg gtgatatatg cacagcacat ggtgcttagt tactttaaaa gtggtcaccc   9120
tcatggcctt ctgttcctac aagaccagct gaagttcgag gacatgctca aagtccaacc   9180
cctgatcgtc tattcggacg acctcgtgct gtatgccgaa tctcccacca tgccgaacta   9240
ccactggtgg gtcgaacatc tgaatttgat gctgggtttt cagacggacc caaagaagac   9300
agccataacg gactcgccat catttctagg ctgtaggata ataaatggac gccagctagt   9360
ccccaaccgt gacaggatcc tcgcggccct cgcttaccat atgaaggcaa acaatgtttc   9420
tgaatactac gccgcggcgg ctgcaatact catggacagc tgtgcttgtt tagagtatga   9480
tcctgaatgg tttgaagagc ttgtggttgg gatagcgcat tgcgcccgca aggacggcta   9540
cagctttccc ggcccgccgt tcttcttgtc catgtgggaa aaactcagat ccaatcatga   9600
ggggaagaag tccagaatgt gcgggtattg cggggccctg gctccgtacg ccactgcctg   9660
tggcctcgac gtctgtattt accacaccca cttccaccag cattgtccag tcacaatctg   9720
gtgtggccac ccggctggtt ctggttcttg tagtgagtgc aaaccccccc tagggaaagg   9780
cacaagccct ctagatgagg tgttagaaca agtcccgtat aagcctccac ggactgtaat   9840
catgcatgtg gagcagggtc tcacccctct tgacccaggc agataccaga ctcgccgcgg   9900
attagtctcc gttaggcgtg gcatcagagg aaatgaagtt gacctaccag acggtgatta   9960
tgctagcacc gccctactcc ccacttgtaa agagatcaac atggtcgctg tcgcctctaa  10020
tgtgttgcgc agcaggttca tcatcggtcc gcccggtgct gggaaaacat actggctcct  10080
tcagcaggtc caggatggtg atgtcattta cacaccgact caccagacca tgctcgacat  10140
gattagggct ttggggacgt gccggttcaa cgtcccagca ggtgcaacgc tgcaattccc  10200
tgccccctcc cgtaccggcc cgtgggttcg catcctagcc ggcggttggt gtcctggtaa  10260
gaattccttc ttggatgaag cagcgtattg taatcacctt gatgtcttga ggctccttag  10320
caaaaccacc ctcacctgtc tgggagactt caaacaactc cacccagtgg gttttgattc  10380
tcattgctat gtttttgaca tcatgcctca gacccagttg aagaccatct ggagattcgg  10440
acagaacatc tgtgatgcca tccaaccaga ttacagggac aaacttgtgt ccatggtcaa  10500
```

-continued

```
cacaacccgt gtaacccacg tggaaaaacc tgtcaagtat gggcaagtcc tcacccctta  10560
ccacagggac cgagaggacg gcgccatcac aattgactcc agtcaaggcg ccacatttga  10620
tgtggtcaca ctgcatttgc ccactaaaga ttcactcaac aggcaaagag cccttgttgc  10680
tatcaccagg gcaagacatg ctatctttgt gtatgaccca cacaggcaat tgcagagcat  10740
gtttgatctt cctgcgaagg gcacacccgt caacctcgca gtgcaccgtg atgagcagct  10800
gatcgtactg gatagaaata ataaagaatg cacagttgct caggctctag gcaacggaga  10860
taaatttagg gccaccgaca agcgcgttgt agattctctc cgcgccattt gtgctgatct  10920
ggaagggtcg agctctccgc tccccaaggt cgcacacaac ttgggatttt atttctcacc  10980
tgatttgaca cagtttgcta aactcccggt agaccttgca ccccactggc ccgtggtgac  11040
aacccagaac aatgaaaagt ggccggatcg gctggttgcc agccttcgcc ctgtccataa  11100
gtatagccgt gcgtgcattg gtgccggcta tatggtgggc ccctcggtgt ttctaggcac  11160
ccctggggtc gtgtcatact acctcacaaa atttgtcaag ggcgaggctc aagtgcttcc  11220
ggagacagtc ttcagcaccg gccgaattga ggtggattgc cgggagtatc ttgatgacag  11280
ggagcgagaa gttgctgagt ccctcccaca tgccttcatt ggcgacgtca aaggcaccac  11340
cgttgggggga tgtcatcatg tcacctccaa ataccttccg cgcttccttc ccaaggaatc  11400
agtcgcggta gtcggggttt cgagccccgg gaaagccgca aaagcagtgt gcacattgac  11460
ggatgtgtac ctcccagacc ttgaggccta cctccaccca gagactcagt ccaagtgctg  11520
gaaagttatg ttggacttca aggaagttcg actgatggtc tggaaagaca agacggccta  11580
tttccaactt gaaggccgct atttcacctg gtatcagctt gcaagctacg cctcgtacat  11640
ccgtgttcct gtcaactcca cggtgtatct ggacccctgc atgggccctg ccctttgcaa  11700
cagaagagtt gtcgggtcca cccattgggg agctgacctc gcagtcaccc cttatgatta  11760
cggtgctaaa atcatcttgt ctagcgctta ccatggtgaa atgcctcctg gatacaagat  11820
tctggcgtgc gcggagttct cgctcgacga cccagtcaag tacaaacaca cctggggttt  11880
tgaatcggat acagcgtatc tgtatgagtt caccggaaac ggtgaggact gggaggatta  11940
caatgatgcg tttcgtgcgc gccagaaagg gaaaatttat aaggccactg ctaccagcat  12000
gaagttttat tttccccccgg gccccgtcat tgaaccaact ttaggcctga attgaaatga  12060
aatggggtct atacaaagcc tcttcgacaa aattggccag ctttttgtgg atgctttcac  12120
ggaatttttg gtgtccattg ttgatatcat catatttttg gccattttgt ttggcttcac  12180
catcgccggt tggctggtgg tcttttgcat cagattggtt tgctccgcgg tattccgtgc  12240
gcgccctgcc attcaccctg agcaattaca gaagatccta tgaggccttt ctttctcagt  12300
gccgggtgga cattcccacc tggggggtaa aacacccttt ggggatgttt tggcaccata  12360
aggtgtcaac cctgattgat gaaatggtgt cgcgtcgaat gtaccgcgtc atggataaag  12420
cagggcaagc tgcctggaaa caggtggtga gcgaggctac gctgtctcgc attagtagtc  12480
tggatgtggt ggctcatttt caacatcttg ccgccattga agccgagacc tgtaaatatt  12540
tggcttctcg actgcccatg ctacacaacc tgcgcatgac agggtcaaat gtaaccatag  12600
tgtataatag cactttaaat caggtgtttg ctatttttcc aacccctggt tcccggccaa  12660
agcttcatga ttttcagcaa tggctaatag ctgtacattc ctccatattt tcctctgttg  12720
cagcttcttg tactcttttt gttgtgctgt ggttgcgggt tccaatgcta cgtactgttt  12780
ttggtttccg ctggttaggg gcaatttttc tttcgaactc atggtgaatt acacggtgtg  12840
tccaccttgc ctcacccgac aagcagccgc tgaggtcctt gaacccggta ggtctctttg  12900
```

-continued gtgcaggata gggcatgacc gatgtgggga ggacgatcac gacgaactgg ggttcatggt 12960
tccgcctggc ctctccagcg aaagccactt gaccagtgtt tacgcctggt tggcgttcct 13020
gtccttcagc tacacggccc agttccatcc cgagatattt gggataggga acgtgagtga 13080
agtttatgtt gacatcaagc accaattcat ctgcgccgtt catgacgggc agaacaccac 13140
cttgcctcgc catgacaata tttcagccgt atttcagacc tactatcaac atcaggtcga 13200
cggcggcaat tggtttcacc tagaatggct gcgtcccttc ttttcctctt ggttggtttt 13260
aaatgtttcg tggtttctca ggcgttcgcc tgcaagccat gtttcagttc gagtctttca 13320
gacatcaaaa ccaacactac cgcagcatca ggctttgttg tcctccagga catcagctgc 13380
cttaggcatg gcgactcgtc ctttccgacg attcgcaaaa gctctcaatg ccgcacggcg 13440
atagggacac ctgtgtatat caccatcaca gccaatgtga cagatgagaa ttacttacat 13500
tcttctgatc tcctcatgct ttcttcttgc cttttctatg cttctgagat gagtgaaaag 13560
ggattcaagg tggtatttgg caatgtgtca ggcatcgtgg ctgtgtgtgt caactttacc 13620
agctacgtcc aacatgtcaa agagtttact caacgctcct tggtggtcga tcatgtgcgg 13680
ctgcttcatt tcatgacacc tgagaccatg aggtgggcaa ccgttttagc ctgtcttttt 13740
gccatcctac tggcaatttg aatgttcaag tatgttgggg aaatgcttga ccgcgggctg 13800
ttgctcgcga ttgctttctt tgtggtgtat cgtgccgttc tggtttgctg tgctcggcaa 13860
cgccaacagc agcagcagct ctcatttcca gttgatttat aacttgacgc tatgtgagct 13920
gaatggcaca gattggctgg cagaaaaatt tgattgggcg gtggagactt ttgtcatctt 13980
tcccgtgttg actcacattg tttcctattg tgcactcacc accagccatt tccttgacac 14040
agttggtctg gttactgtgt ccaccgccgg gttttatcac gggcggtatg tcttgagtag 14100
catctacgcg gtctgtgctc tggctgcgtt gatttgcttc gttattaggc ttgcgaagaa 14160
ctgcatgtcc tggcgctact cttgtaccag atataccaac ttccttctgg acactaaggg 14220
cagactctat cgttggcggt cgcccgttat catagaaaaa aggggtaagg ttgaggtcga 14280
aggtcatctg atcgacctca aaagagttgt gcttgatggt tccgtggcaa cccctttaac 14340
cagagtttca gcggaacaat ggggtcgtct ctagacgact tttgccatga tagcactgct 14400
ccacaaaagg tgcttttggc gttttccatt acctacacgc cagtaatgat atatgctcta 14460
aaggtaagtc gcggccgact gctagggctt ctgcaccttt tgatctttct gaattgtgct 14520
tttaccttcg ggtacatgac attcgcgcac tttcagagca caaatagggt cgcgctcgct 14580
atgggagcag tagttgcact tctttggggg gtgtactcag ccatagaaac ctggaaattc 14640
atcacctcca gatgccgttt gtgcttgcta ggccgcaagt acattctggc ccctgcccac 14700
cacgtcgaaa gtgccgcggg ctttcatccg attgcggcaa atgataacca cgcatttgtc 14760
gtccggcgtc ccggctccat tacggttaac ggcacattgg tgcccgggtt gaaaagcctc 14820
gtgttgggtg gcagaaaagc tgttaaacag ggagtggtaa accttgtcaa atatgccaaa 14880
taacaacggc aagcagcaaa agaaaaagaa ggggaatggc cagccagtca accagctgtg 14940
ccagatgctg ggtaaaatca tcgcccagca aaaccagtcc agaggcaagg gaccgggcaa 15000
gaaaagtaag aagaaaaacc cggagaagcc ccattttcct ctagcgaccg aagatgacgt 15060
caggcatcac ttcacccctg gtgagcggca attgtgtctg tcgtcgatcc agactgcctt 15120
taaccagggc gctggaactt gtaccctgtc agattcaggg aggataagtt acactgtgga 15180
gtttagtttg ccgacgcatc atactgtgcg cctgatccgc gtcacagcat caccctcagc 15240

-continued

```
atgatgggct ggcattcttt aggcacctca gtgtcagaat tggaagaatg tgtggtggat  15300

ggcactgatt gacattgtgc ctctaagtca cctattcaat tagggcgacc gtgtgggggt  15360

aaaatttaat tggcgagaac catgcggccg caattaaaaa aaaaaaaaaa aaaaaaaaaa  15420

aaaaaaaaaa aaaaaaaaaa aaaaaaaaaa                                   15450
```

<210> SEQ ID NO 17
<211> LENGTH: 2352
<212> TYPE: DNA
<213> ORGANISM: Porcine reproductive and respiratory syndrome virus

<400> SEQUENCE: 17

```
cctatcattg aaccaacttt aggcctgaat tgaaatgaaa tggggtctat gcaaagcctt     60

tttgacaaaa ttggccaact tttcgtggat gctttcacgg agttcttggt gtccattgtt    120

gatatcatta tatttttggc cattttgttt ggcttcacca tcgccggttg gctggtggtc    180

ttttgcatca gattggtttg ctccgcgata ctccgtgcgc gccctgccat tcactctgag    240

caattacaga agatcctatg aggcctttct ttctcagtgc caggtggaca ttcccacctg    300

gggaattaaa catcctttgg ggatgctttg gcaccataag gtgtcaaccc tgattgatga    360

aatggtgtcg cgtcgaatgt accgcatcat ggaaaaagca ggacaggctg cctggaaaca    420

ggtggtgagc gaggctacgc tgtctcgcat tagtagtttg gatgtggtgg ctcactttca    480

gcatcttgcc gccattgaag ccgagacctg taaatatttg gcctctcggc tgcccatgct    540

acacaacctg cgcatgacag ggtcaaatgt aaccatagtg tataatagta ctttgaatca    600

ggtgcttgct attttcccaa cccctggttc ccggccaaag cttcatgatt ttcagcaatg    660

gctaatagct gtacattcct ctatattttc ctctgttgca gcttcttgta ctctttttgt    720

tgtgctgtgg ttgcgggttc caatgctacg tattgctttt ggtttccgct ggttaggggc    780

aatttttctt tcgaactcac agtgaactac acggtgtgtc caccttgcct cacccggcaa    840

gcagccacag aggcctacga acctggcagg tctctttggt gcaggatagg gtatgatcgc    900

tgtggggagg acgatcatga tgaactaggg tttgtggtgc cgtctggcct ctccagcgaa    960

ggccacttga ccagtgttta cgcctggttg gcgttcctgt ctttcagtta cacagcccag   1020

ttccatcctg agatattcgg gatagggaat gtgagtcaag tttatgttga catcaggcat   1080

caattcattt gcgccgttca cgacgggcag aacgccactt tgcctcgcca tgacaatatt   1140

tcagccgtgt tccagactta ttaccaacat caagtcgacg gcggcaattg gtttcaccta   1200

gaatggctgc gtcccttctt ttcctcttgg ttggttttaa atgtctcttg gtttctcagg   1260

cgttcgcctg caagccatgt ttcagttcga gtcttgcaga cattaagacc aacaccaccg   1320

cagcggcagg ctttgctgtc ctccaagaca tcagttgcct taggtatcgc aactcggcct   1380

ctgaggcgtt tcgcaaaatc cctcagtgtc gtacggcgat agggacaccc atgtatatta   1440

ctgtcacagc caatgtaacc gatgagaatt atttgcattc ctctgacctt ctcatgcttt   1500

cttcttgcct tttctacgct tctgagatga gtgaaaaggg atttaaagtg gtatttggca   1560

atgtgtcagg catcgtggct gtgtgcgtca actttaccag ctacgtccaa catgtcaagg   1620

aatttaccca acgctccttg gtagtcgacc atgtgcggct gctccatttc atgacacctg   1680

agaccatgag gtgggcaact gttttagcct gtctttttgc cattctgttg gccatttgaa   1740

tgtttaagta tgttggggaa atgcttgacc gcgggctatt gctcgtcatt gctttttttg   1800

tggtgtatcg tgccgtcttg gtttgttgcg ctcgccagcg ccaacagcag caacagctct   1860

catttacagt tgatttataa cttgacgcta tgtgagctga atggcacaga ttggttagct   1920
```

-continued

```
ggtgaatttg actgggcagt ggagtgtttt gtcatttttc ctgtgttgac tcacattgtc   1980

tcctatggtg ccctcaccac cagccatttc cttgacacag tcggtctggt cactgtgtct   2040

accgccggct tttcccacgg gcggtatgtt ctgagtagca tctacgcggt ctgtgccctg   2100

gctgcgttga tttgcttcgt cattaggttt acgaagaatt gcatgtcctg gcgctactca   2160

tgtaccagat ataccaactt tcttctggac actaagggca gactctatcg ttggcggtcg   2220

cctgtcatca tagagaaaag gggtaaagtt gaggtcgaag gtcatctgat cgacctcaag   2280

agagttgtgc ttgatggttc cgcggcaacc cctataacca aagtttcagc ggagcaatgg   2340

ggtcgtcctt ag                                                       2352


<210> SEQ ID NO 18
<211> LENGTH: 886
<212> TYPE: DNA
<213> ORGANISM: Porcine reproductive and respiratory syndrome virus

<400> SEQUENCE: 18

atggggtcgt ccttagatga cttctgccat gatagcacgg ctccacaaaa ggtgcttttg     60

gcgttctcta ttacctacac gccagtgatg atatatgccc taaaagtaag tcgcggccga    120

ctgctagggc ttctgcacct tttgatcttc ctaaattgtg ctttcacctt cgggtacatg    180

acattcgtgc actttcagag cacaaacaag gtcgcgctca ctatgggagc agtagttgca    240

ctcctttggg gggtgtactc agccatagaa acctggaaat tcatcacctc cagatgccgt    300

ttgtgcttgc taggccgcaa gtacattttg gcccctgccc accacgttga aagtgccgca    360

ggctttcatc cgatagcggc aaatgataac cacgcatttg tcgtccggcg tcccggctcc    420

actacggtta acggcacatt ggtgcccggg ttgaaaagcc tcgtgttggg tggcagaaaa    480

gctgtcaaac agggagtggt aaaccttgtt aaatatgcca aataacaacg gcaagcagca    540

gaagaaaaag aagggggatg gccagccagt caatcagctg tgccagatgc tgggtaagat    600

catcgctcag caaaaccagt ccagaggcaa gggaccggga aagaaaaaca agaagaaaaa    660

cccggagaag ccccattttc ctctagcgac tgaagatgat gtcagacatc acttcacctc    720

tggtgagcgg caattgtgtc tgtcgtcaat ccagacagcc tttaatcaag gcgctggaac    780

ttgtaccctg tcagattcag ggaggataag ttacactgtg gagtttagtt tgccgacgca    840

tcatactgtg cgcctgatcc gcgtcacagc gtcaccctca gcatga                  886
```